US011628208B2

United States Patent
D'Souza

(10) Patent No.: US 11,628,208 B2
(45) Date of Patent: Apr. 18, 2023

(54) SYSTEM AND METHOD FOR MICRONEEDLE DELIVERY OF MICROENCAPSULATED VACCINE AND BIOACTIVE PROTEINS

(71) Applicant: THE CORPORATION OF MERCER UNIVERSITY, Macon, GA (US)

(72) Inventor: Martin J. D'Souza, Duluth, GA (US)

(73) Assignee: THE CORPORATION OF MERCER UNIVERSITY, Macon, GA (US)

( * ) Notice: Subject to any disclaimer, the term of this patent is extended or adjusted under 35 U.S.C. 154(b) by 229 days.

(21) Appl. No.: 17/107,468

(22) Filed: Nov. 30, 2020

(65) Prior Publication Data

US 2021/0100880 A1 Apr. 8, 2021

Related U.S. Application Data

(63) Continuation-in-part of application No. 16/171,465, filed on Oct. 26, 2018, now Pat. No. 10,849,962, which is a continuation of application No. 16/017,542, filed on Jun. 25, 2018, now Pat. No. 10,786,558, which is a continuation of application No. 14/874,978, filed on Oct. 5, 2015, now Pat. No. 10,004,790.

(51) Int. Cl.

| | |
|---|---|
| *A61K 39/00* | (2006.01) |
| *C12N 7/00* | (2006.01) |
| *A61K 39/165* | (2006.01) |
| *A61K 39/095* | (2006.01) |
| *A61K 9/00* | (2006.01) |
| *A61K 9/51* | (2006.01) |
| *A61K 31/245* | (2006.01) |
| *A61K 31/46* | (2006.01) |
| *A61K 31/5383* | (2006.01) |
| *A61K 31/7036* | (2006.01) |
| *A61K 31/7048* | (2006.01) |
| *A61K 31/7088* | (2006.01) |
| *A61K 31/727* | (2006.01) |
| *C12N 15/88* | (2006.01) |
| *A61K 9/16* | (2006.01) |
| *C12N 5/071* | (2010.01) |
| *A61K 39/155* | (2006.01) |
| *A61K 48/00* | (2006.01) |

(52) U.S. Cl.
CPC ............ *A61K 39/00* (2013.01); *A61K 9/0021* (2013.01); *A61K 9/1652* (2013.01); *A61K 9/5161* (2013.01); *A61K 9/5169* (2013.01); *A61K 9/5192* (2013.01); *A61K 31/245* (2013.01); *A61K 31/46* (2013.01); *A61K 31/5383* (2013.01); *A61K 31/7036* (2013.01); *A61K 31/7048* (2013.01); *A61K 31/7088* (2013.01); *A61K 31/727* (2013.01); *A61K 39/0008* (2013.01); *A61K 39/0011* (2013.01); *A61K 39/095* (2013.01); *A61K 39/155* (2013.01); *A61K 39/165* (2013.01); *C12N 5/0677* (2013.01); *C12N 7/00* (2013.01); *C12N 15/88* (2013.01); *A61K 48/00* (2013.01); *A61K 2039/52* (2013.01); *A61K 2039/54* (2013.01); *A61K 2039/55555* (2013.01); *A61K 2039/55594* (2013.01); *A61K 2039/57* (2013.01); *C12N 2533/72* (2013.01); *C12N 2533/74* (2013.01); *C12N 2760/18434* (2013.01); *C12N 2760/18534* (2013.01)

(58) Field of Classification Search
None
See application file for complete search history.

(56) References Cited

U.S. PATENT DOCUMENTS

| | | |
|---|---|---|
| 3,137,631 A | 6/1964 | Soloway |
| 3,202,731 A | 8/1965 | Grevenstuk et al. |
| 3,429,827 A | 2/1969 | Ruus |

(Continued)

FOREIGN PATENT DOCUMENTS

| | | |
|---|---|---|
| JP | H09506109 A | 6/1997 |
| JP | H10506406 A | 6/1998 |

(Continued)

OTHER PUBLICATIONS

Office Action for European Patent Application No. 17869270.3; dated Apr. 22, 2021.
Modi et al., The oxytocin system in drug discovery for autism: animal models and novel therapeutic strategies, Horm Behav, 2012, pp. 340-350, vol. 61.
Montesano et al., Increased proteolytic activity is responsible for the aberrant morphogenetic behavior of endothelial cells expressing the middle T oncogene. Cell, 1990, pp. 435-445, vol. 62.

(Continued)

*Primary Examiner* — Anand U Desai
(74) *Attorney, Agent, or Firm* — Barnes & Thornburg LLP; Jason A. Bernstein

(57) ABSTRACT

A method for producing at least one microneedle containing a vaccine for transdermal delivery of the vaccine to a patient includes preparing microparticles or nanoparticles of encapsulated vaccine by preparing a solution comprising a vaccine antigen and a biocompatible polymer matrix; and spray drying the solution to form the microparticles or nanoparticles. The method includes the further steps of preparing a film composition including at least one pre-polymer solution; preparing a suspension comprising the microparticles or nanoparticles and the film composition; loading the suspension into a 3D printer; printing, via the 3D printer, at least one microneedle made from the suspension; and, converting the pre-polymer solution into a cross-linked biopolymer by exposing the at least one microneedle to UV light. Also disclosed are microneedles containing a vaccine for transdermal delivery.

21 Claims, 36 Drawing Sheets

(56) References Cited

U.S. PATENT DOCUMENTS

| | | | |
|---|---|---|---|
| 3,663,685 | A | 5/1972 | Evans |
| 3,663,686 | A | 5/1972 | Grotenhuis et al. |
| 3,663,687 | A | 5/1972 | Evans |
| 3,758,678 | A | 9/1973 | Lindsay et al. |
| 3,937,668 | A | 2/1976 | Zolle |
| 3,962,414 | A | 6/1976 | Michaels |
| 4,147,767 | A | 4/1979 | Yapel, Jr. |
| 4,169,804 | A | 10/1979 | Yapel, Jr. |
| 4,186,183 | A | 1/1980 | Steck et al. |
| 4,230,687 | A | 10/1980 | Sair et al. |
| 4,349,530 | A | 9/1982 | Royer |
| 4,356,259 | A | 10/1982 | Banba |
| 4,671,954 | A | 6/1987 | Goldberg et al. |
| 4,674,480 | A | 6/1987 | Lemelson |
| 4,680,174 | A | 7/1987 | Jarvis, Jr. et al. |
| 4,764,359 | A | 8/1988 | Lemelson |
| 4,925,661 | A | 5/1990 | Huang |
| 4,963,367 | A | 10/1990 | Ecanow |
| 5,017,379 | A | 5/1991 | Lemelson |
| 5,069,936 | A | 12/1991 | Yen |
| 5,129,877 | A | 7/1992 | Gallo et al. |
| 5,690,954 | A | 11/1997 | Illum |
| 6,117,454 | A | 9/2000 | Kreuter et al. |
| 6,498,147 | B2 | 12/2002 | Nerenberg et al. |
| 6,555,110 | B1 | 4/2003 | D'Souza |
| 7,105,158 | B1 | 9/2006 | D'Souza et al. |
| 8,053,000 | B2 | 11/2011 | Srinivas et al. |
| 2002/0081336 | A1 | 6/2002 | Jonsson et al. |
| 2002/0177568 | A1 | 11/2002 | Stinchomb et al. |
| 2004/0005569 | A1 | 1/2004 | Baker et al. |
| 2004/0043079 | A1 | 3/2004 | D'Souza |
| 2005/0089576 | A1 | 4/2005 | Moreau |
| 2007/0078414 | A1 | 4/2007 | McAllister et al. |
| 2008/0166414 | A1 | 7/2008 | Hanes et al. |
| 2008/0269666 | A1 | 10/2008 | Wang et al. |
| 2009/0081306 | A1 | 3/2009 | D'Souza |
| 2009/0155330 | A1 | 6/2009 | Ghartey-Tagoe et al. |
| 2010/0111984 | A1 | 5/2010 | D'Souza |
| 2011/0121486 | A1 | 5/2011 | Oh et al. |
| 2013/0224245 | A1* | 8/2013 | Kommareddy .......... C12N 7/00 424/210.1 |
| 2015/0112250 | A1 | 4/2015 | Kwon |
| 2016/0058992 | A1 | 3/2016 | Chen |
| 2016/0287668 | A1 | 10/2016 | Tankovich |

FOREIGN PATENT DOCUMENTS

| | | | |
|---|---|---|---|
| JP | 2005513098 | A | 5/2005 |
| JP | 2006511461 | A | 4/2006 |
| WO | 9410980 | A1 | 5/1994 |
| WO | 9522963 | A1 | 8/1995 |
| WO | 9609814 | A1 | 4/1996 |
| WO | 0002574 | A1 | 1/2000 |
| WO | 03053413 | A2 | 7/2003 |
| WO | 2008053481 | A1 | 5/2008 |
| WO | 2009094394 | A1 | 7/2009 |
| WO | 2012153266 | A2 | 11/2012 |
| WO | 2016163753 | A1 | 10/2016 |

OTHER PUBLICATIONS

Morley et al., Serotonin (1A) receptor involvement in acute 3,4-methylenedioxymethamphetamine (MDMA) facilitation of social interaction in the rat, Prog Neuropsychopharmacol Biol Psychiatry, 2005, pp. 648-657, vol. 29.

Murnane et al., Endocrine and neurochemical effects of 3,4-methylenedioxymethamphetamine and its stereoisomers in rhesus monkeys, J Pharmacol Exp Ther, 2010, pp. 642-650, vol. 334.

Murnane et al., The neuropharmacology of prolactin secretion elicited by 3,4-methylenedioxymethamphetamine ("ecstasy"): a concurrent microdialysis and plasma analysis study, Horm Behav, 2012, pp. 181-60, vol. 61.

Nagahara et al., Neuroprotective effects of brain-derived neurotrophic factor in rodent and primate models of Alzheimer's disease, Nature medicine, 2009, pp. 331-337, vol. 15.

Nasatto et al., Methylcellulose, a cellulose derivative with original physical properties and extended applications, Polymers, Apr. 24, 2015, vol. 7, pp. 777-803.

Notification of Reasons for Refusal Translation, dated Dec. 24, 2013, JP Patent Application No. 2011-529378.

O'Brien et al., Amyloid precursor protein processing and Alzheimer's disease, Annu Rev Neurosci, 2011, pp. 185-204, vol. 34.

Oettinger et al., Pro-inflammatory cytokine inhibition in the primate using microencapsulated antisense oligomers to NF-kappaB, J Microencapsul, 2007, pp. 337-348, vol. 24.

Opal et al., Anti-inflammatory cytokines, Chest, 2000, pp. 1162-1172, vol. 117.

Pan et al., Cationic lipid-coated magnetic nanoparticles associated with transferrin for gene delivery, International journal of pharmaceutics, 2008, pp. 263-270, vol. 358.

Pang et al., Enhanced intracellular delivery and chemotherapy for glioma rats by transferrin-conjugated biodegradable polymersomes loaded with doxorubicin, Bioconjugate chemistry, 2011, pp. 1171-1180, vol. 22.

Pardridge, Blood-brain barrier delivery, Drug discovery today, 2007, pp. 54-61, vol. 12.

Pardridge, Blood-brain barrier drug delivery of IgG fusion proteins with a transferrin receptor monoclonal antibody, Expert opinion on drug delivery, 2014, pp. 1-16.

Prego et al., Chitosan-PEG nanocapsules as new carriers for oral peptide delivery: Effect of chitosan pegylation degree, Journal of Controlled Release, 2006, 111:299-308.

Pulicherla et al., Targeting therapeutics across the blood brain barrier (BBB), prerequisite towards thrombolytic therapy for cerebrovascular disorders—an overview and advancements, AAPS PharmSciTech, 2015, pp. 223-233, vol. 16.

Qian et al., Targeted drug delivery via the transferrin receptor-mediated endocytosis pathway, Pharmacol Rev, 2002, pp. 561-587, vol. 54.

Reibel et al., Neuropeptide Y and epilepsy: varying effects according to seizure type and receptor activation, Peptides, 2001, pp. 529-539, vol. 22.

Robertson et al., Immunoassay of plasma vasopressin, Man. Proc Natl Acad Sci USA, 1970, pp. 1298-1305; vol. 66.

Sahoo et al., Enhanced antiproliferative activity of transferrin-conjugated paclitaxel-loaded nanoparticles is mediated via sustained intracellular drug retention, Molecular pharmaceutics, 2005, pp. 373-383, vol. 2.

Saraiva et al., Nanoparticle-mediated brain drug delivery: Overcoming blood-brain barrier to treat neurodegenerative diseases, Journal of controlled release : official journal of the Controlled Release Society, 2016, pp. 34-47, vol. 235.

Sean P. Sullivan et al: "Dissolving polymer microneedle patches for influenza vaccination", Nature Medicine, vol. 16, No. 8, Aug. 1, 2010 (Aug. 1, 2010), pp. 915-920, XP055568344, New York ISSN: 1078-8956, DOI: 10.1038/nm.2182 * p. 915, col. 2, paragraph 4—p. 916, col. 1, paragraph 1 *.

Search Report and Written Opinion from International Application No. PCT/US2016/55515; dated Jan. 24, 2017.

Search Report for European Patent Application No. 17869270.3; dated Apr. 29, 2020.

Search Report for International Patent Application No. PCT/US2017/061353; dated Jan. 29, 2018.

Shastri et al., Implementation of mixture design for formulation of albumin containing enteric-coated spray-dried microparticles, Drug development and industrial pharmacy, 2013, pp. 164-175, vol. 39.

Sikorski et al., The Peyer's patch high endothelial receptor for lymphocytes, the mucosal vascular addressin, is induced on a murine endothelial cell line by tumor necrosis factor-alpha and IL-1, Journal of immunology, 1993, pp. 5239-5250; vol. 151, Baltimore, Maryland.

Sloane et al., Anti-inflammatory cytokine gene therapy decreases sensory and motor dysfunction in experimental Multiple Sclerosis:

(56) References Cited

OTHER PUBLICATIONS

MOG-EAE behavioral and anatomical symptom treatment with cytokine gene therapy, Brain, behavior, and immunity, 2009, pp. 92-100, vol. 23.
Soderquist et al., Central nervous system delivery of large molecules: challenges and new frontiers for intrathecally administered therapeutics, Expert opinion on drug delivery, 2010, pp. 285-293, vol. 7.
Son et al., RVG peptide tethered bioreducible polyethylenimine for gene delivery to brain, Journal of controlled release : official journal of the Controlled Release Society, 2011, pp. 18-25, vol. 155.
Sonavane et al., Biodistribution of colloidal gold nanoparticles after intravenous administration: effect of particle size, Colloids and surfaces B, Biointerfaces, 2008, pp. 274-280, vol. 66.
Srinivasan et al., TEER measurement techniques for in vitro barrier model systems, Journal of laboratory automation, 2015, pp. 107-126, vol. 20.
Strecker et al., Parkinson's disease: emerging pharmacotherapy, Expert opinion on emerging drugs, 2008, pp. 573-591, vol. 13.
Striepens et al., Elevated cerebrospinal fluid and blood concentrations of oxytocin following its intranasal administration in humans, Scientific reports, 2013, p. 3440, vol. 3.
Sundaram et al., Surface-functionalized nanoparticles for targeted gene delivery across nasal respiratory epithelium, Faseb j, 2009, pp. 3752-3765, vol. 23.
Supplementary European Search Report for European Patent Application No. EP 09 81 7062, filed Sep. 29, 2009, dated Mar. 20, 2013.
Tan et al., The influence of size, shape and vessel geometry on nanoparticle distribution, Microfluidics and nanofluidics, 2013, pp. 77-87; vol. 14.
Terryn et al., Protective effect of different anti-rabies virus VHH constructs against rabies disease in mice, PLoS One, 2014, e109367, vol. 9, No. 10.
Thompson et al., A role for oxytocin and 5-HT(1A) receptors in the prosocial effects of 3,4 methylenedioxymethamphetamine ("ecstasy"), Neuroscience, 2007, pp. 509-514, vol. 146.
Tong et al. Evaluation of PLGA microspheres as delivery system for antitumor agent-camptothecin, Drug development and industrial pharmacy, 2003, pp. 745-756, vol. 29.
Truong et al., The importance of nanoparticle shape in cancer drug delivery, Expert opinion on drug delivery, 2015, pp. 129-142, vol. 12.
Ulbrich et al., Transferrin- and transferrin-receptor-antibody-modified nanoparticles enable drug delivery across the blood-brain barrier (BBB), European journal of pharmaceutics and biopharmaceutics : official journal of Arbeitsgemeinschaft fur Pharmazeutische Verfahrenstechnik eV, 2009, pp. 251-256, vol. 71.
Walker et al., Anti-inflammatory and immune therapy for Alzheimer's disease: current status and future directions, Current neuropharmacology, 2007, pp. 232-243, vol. 5.
Watanabe et al., Paracellular barrier and tight junction protein expression in the immortalized brain endothelial cell lines bEND.3, bEND.5 and mouse brain endothelial cell 4, Biological & pharmaceutical bulletin, 2013, pp. 492-495, vol. 36.
Wiley et al., Transcytosis and brain uptake of transferrin-containing nanoparticles by tuning avidity to transferrin receptor, Proc Natl Acad Sci USA, 2013, pp. 8662-8667, vol. 110.
Williams et al., Embryonic lethalities and endothelial tumors in chimeric mice expressing polyoma virus middle T oncogene. Cell, 1988, pp. 121-131, vol. 52.
Woldbye, Antiepileptic effects of NPY on pentylenetetrazole seizures, Regulatory peptides, 1998, pp. 279-282, vol. 75-76.
Wuest et al., Membrane configuration optimization for a murine in vitro blood-brain barrier model, J Neurosci Methods, 2013, pp. 211-221, vol. 212.
Kan et al., Transferrin-conjugated, fluorescein-loaded magnetic nanoparticles for targeted delivery across the blood-brain barrier, Journal of materials science Materials in medicine, 2013, pp. 2371-2379, vol. 24.

Abbott et al., Structure and function of the blood-brain barrier, Neurobiology of disease, 2010, pp. 13-25, vol. 37.
Alimohammadi et al., Evidence for nicotinic acetylcholine receptors on nasal trigeminal nerve endings of the rat, chemical senses, 2000, pp. 61-66, vol. 25.
Anand et al., Drug transporters in the nasal epithelium: an overview of strategies in targeted drug delivery, Future medicinal chemistry, 2014, pp. 1381-1397, vol. 6.
Ballabh et al., The blood-brain barrier: an overview: structure, regulation, and clinical implications, Neurobiology of disease, 2004, pp. 1-13, vol. 16.
Bhowmik et al., A novel microparticulate vaccine for melanoma cancer using transdermal delivery, J Microencapsul., May 17, 2011, vol. 28, No. 4, pp. 294-300.
Blesch et al., Transient growth factor delivery sustains regenerated axons after spinal cord injury, J Neurosci, 2007, pp. 10535-10545, vol. 27.
Bogdan et al., The role of nitric oxide in innate immunity, Immunological reviews, 2000, pp. 17-26, vol. 27.
Born et al., Sniffing neuropeptides: a transnasal approach to the human brain, Nat Neurosci, 2002, pp. 514-516, vol. 5.
Broadwell et al., Transcytosis of protein through the mammalian cerebral epithelium and endothelium. III. Receptor-mediated transcytosis through the blood-brain barrier of blood-borne transferrin and antibody against the transferrin receptor, Experimental neurology, 1996, pp. 47-65, vol. 142.
Broderick et al., Vascular risk factors and dementia: how to move forward?, Neurology, 2009, pp. 1934-1935, vol. 73.
Carson et al., A brief history of oxytocin and its role in modulating psychostimulant effects, Journal of psychophanmacology, 2013, pp. 231-247, vol. 27, Oxford, England.
Ceseracciu et al., Robust and biodegradable elastomers based on com starch and polydimethylsiloxane (PDMS), ACS Appl Mater Interfaces, Jan. 26, 2015, vol. 7, No. 6, pp. 3742-3753.
Chablani et al., Spray-dried microparticles: a potential vehicle for oral delivery of vaccines, J Microencapsul, 2012, pp. 388-397, vol. 29.
Crcarevska et al., Chitosan coated Ca-alginate microparticles loaded with budesonide for delivery to the inflamed colonic mucosa, European Journal of Pharmaceutics 2008, 68:565-578, Available online Jun. 14, 2007.
Dal Monte et al., CSF and blood oxytocin concentration changes following intranasal delivery in macaque, PLoS One, 2014, e103677, vol. 9, No. 8.
Dawbarn et al., Neurotrophins and neurodegeneration, Neuropathology and applied neurobiology, 2003, pp. 211-230, vol. 29.
Donaldson et al., Oxytocin, vasopressin, and the neurogenetics of sociality, Science, 2008, pp. 900-904, vol. 322, New York, New York.
Dumont et al., Increased oxytocin concentrations and prosocial feelings in humans after ecstasy (3,4-methylenedioxymethamphetamine) administration, Soc Neurosci, 2009, pp. 359-366, vol. 4.
Engelmann et al., Behavioral consequences of intracerebral vasopressin and oxytocin: focus on learning and memory, Neurosci Biobehav Rev, 1996, pp. 341-358, vol. 20.
Etame et al., Design and potential application of PEGylated gold nanoparticles with size-dependent permeation through brain microvasculature, Nanomedicine : nanotechnology, biology, and medicine, 2011, pp. 992-1000, vol. 7.
Gan et al., Transferrin-conjugated nanoparticles of poly(lactide)-D-alpha-tocopheryl polyethylene glycol succinate diblock copolymer for targeted drug delivery across the blood-brain barrier, Biomaterials, 2010, pp. 7748-7757, vol. 31.
Gatter et al., Transferrin receptors in human tissues: their distribution and possible clinical relevance, Journal of Clinical pathology, 1983, pp. 539-545, vol. 36.
Golde et al., A rapid, simple, and humane method for submandibular bleeding of mice using a lancet, Lab animal, J005, pp. 39-43, vol. 34.
Gooding et al., Synthesis and characterization of rabies virus glycoprotein-tagged amphiphilic cyclodextrins for siRNA delivery in human glioblastoma cells: in vitro analysis, European journal of

(56) References Cited

OTHER PUBLICATIONS pharmaceutical sciences: official journal of the European Federation for Pharmaceutical Sciences, 2015, pp. 80-92, vol. 71.

Hanada et al., Cell-based in vitro blood-brain barrier model can rapidly evaluate nanoparticles' brain permeability in association with particle size and surface modification, International journal of molecular sciences, 2014, pp. 1812-1825, vol. 15.

Harris et al., Subjective and hormonal effects of 3,4-methylenedioxymethamphetamine (MDMA) in humans, Psychopharmacology, 2002, pp. 396-405, vol. 162.

Haswani et al., Formulation, Characterization and Pharmacokinetic Evaluation of Gentamicin Sulphate Loaded Albumin Microspheres; Journal of Microencapsulation, Dec. 2006; vol. 23, No. 8; pp. 875-886.

He et al., Immortalized mouse brain endothelial cell line Bend.3 displays the comparative barrier characteristics as the primary brain microvascular endothelial cells, Zhongguo dang dai er ke za zhi (Chinese journal of contemporary pediatrics), 2010, pp. 474-478, vol. 12.

Herrmann et al., Current and emerging drug treatment options for Alzheimer's disease: a systematic review, Drugs, 2011, pp. 2031-2065, vol. 71.

Huang et al., The Characteristics of Betamethasone-Loaded Chitosan Microparticles by Spray-Drying Method, Journal of Microencapsulation, vol. 20, No. 4, Jul./Aug. 2003, pp. 459-472.

International Preliminary Report on Patentability for International Patent Application No. PCT/US2017/061353; dated May 14, 2019.

Jones et al., Spray-dried doxorubicin-albumin microparticulate systems for treatment of multidrug resistant melanomas, Journal of drug targeting, 2011, pp. 427-433, vol. 19.

Keech et al., Intranasal oxytocin, social cognition and neurodevelopmental disorders: A meta-analysis, Psychoneuroendocrinology, 2018, pp. 9-19, vol. 87.

Keiger et al. Nicotinic cholinergic receptor expression in the human nasal mucosa, The Annals of otology, rhinology, and laryngology, 2003, pp. 77-84, vol. 112.

Kim et al., Brain-targeted delivery of protein using chitosan- and RVG peptide-conjugated, pluronic-based nano-carrier, Biomaterials, 2013, pp. 1170-1178, vol. 34.

Klemp et al., Repeated inhibitory effects of NPY on hippocampal CA3 seizures and wet dog shakes, Peptides, 2001, pp. 523-527, vol. 22.

Kolluru et al., Formulation development of albumin based theragnostic nanoparticles as a potential delivery system tor tumor targeting, Journal of drug targeting, 2013, pp. 77-86, vol. 21.

Kou et al., The endocytosis and intracellular fate of nanomedicines: Implication for rational design, Asian Journal of Pharmaceutical Sciences, 2013, pp. 1-10, vol. 8.

Kulkarni et al. Effects of particle size and surface modification on cellular uptake and biodistribution of polymeric nanoparticles for drug delivery, Pharmaceutical research, 2013, pp. 2512-2522, vol. 30.

Kumar et al., Transvascular delivery of small interfering RNA to the central nervous system, Nature, 2007, pp. 39-43, vol. 448.

Lafay et al., Spread of the CVS strain of rabies virus and of the avirulent mutant AvO1 along the olfactory pathways of the mouse after intranasal inoculation, Virology, 1991, pp. 320-330, vol. 183.

Leng et al., Intranasal Oxytocin: Myths and Delusions, Biol Psychiatry, 2016, pp. 243-250, vol. 79.

Li et al., Nanoparticles bearing polyethyleneglycol-coupled transferrin as gene carriers: preparation and in vitro evaluation. International journal of pharmaceutics, 2003, pp. 93-101, vol. 259.

Li et al., Transepithelial electrical measurements with the Ussing chamber, Journal of cystic fibrosis: official journal of the European Cystic Fibrosis Society, 2004, pp. 123-126, vol. 3, Suppl. 2.

Liu et al., A technique for serial collection of cerebrospinal fluid from the cisterna magna in mouse, Journal of visualized experiments (JoVE), 2008; p. 960, vol. 21.

Liu et al., Brain-targeted co-delivery of therapeutic gene and peptide by multifunctional nanoparticles in Alzheimer's disease mice, Biomaterials, 2016, pp. 33-45, vol. 80.

Makadia et al., Poly Lactic-co-Glycolic Acid (PLGA) as Biodegradable Controlled Drug Delivery Carrier, Polymers, 2011, pp. 1377-1397, vol. 3.

Mann et al., Transferrin conjugation confers mucosal molecular targeting to a model HIV-1 trimeric gp140 vaccine antigen, Journal of controlled release : official journal of the Controlled Release Society, 2012, pp. 240-249, vol. 158.

Misra et al., Drug delivery to the central nervous system: a review, Journal of pharmacy & pharmaceutical sciences : a publication of the Canadian Society for Pharmaceutical Sciences (Societe canadienne des sciences pharmaceutiques), 2003, pp. 252-273, vol. 6.

Modi et al. Aerosolized oxytocin increases cerebrospinal fluid oxytocin in rhesus macaques, Psychoneuroendocrinology, 2014, pp. 49-57, vol. 45.

Yeung et al.. Membrane phosphatidylserine regulates surface charge and protein localization, Science, 2008, pp. 210-213, vol. 319, New York, New York.

King et al., Dual-targeting daunorubicin liposomes improve the therapeutic efficacy of brain glioma in animals, Journal of controlled release : official journal of the Controlled Release Society, 2010, pp. 183-192; vol. 141.

Zhang et al., Transferrin receptor targeted lipopolyplexes for delivery of antisense oligonucleotide g3139 in a murine K562 xenograft model, Pharmaceutical research, 2009, pp. 1516-1524, vol. 26.

Zughaier et al., Antimicrobial peptides and endotoxin inhibit cytokine and nitric oxide release but amplify respiratory burst response in human and murine macrophages, Cellular microbiology, 2005, pp. 1251-1262; vol. 7.

* cited by examiner

SYSTEM AND METHOD FOR MICRONEEDLE DELIVERY OF MICROENCAPSULATED VACCINE AND BIOACTIVE PROTEINS

CROSS-REFERENCE TO RELATED APPLICATIONS

This application is a continuation-in-part of U.S. patent application Ser. No. 16/171,465, filed Oct. 26, 2018, entitled METHOD AND APPARATUS FOR MICRONEEDLE TRANSDERMAL DELIVERY, which is a continuation of U.S. patent application Ser. No. 16/017,542, filed Jun. 25, 2018, entitled METHOD AND APPARATUS FOR MICRONEEDLE TRANSDERMAL DELIVERY OF MICROENCAPSULATED BIOACTIVE MATERIALS, now U.S. Pat. No. 10,786,558, which is a continuation of U.S. patent application Ser. No. 14/874,978, filed Oct. 5, 2015, entitled METHOD AND APPARATUS FOR MICRONEEDLE TRANSDERMAL DELIVERY OF MICROENCAPSULATED BIOACTIVE MATERIALS, now U.S. Pat. No. 10,004,790, commonly assigned to the assignee of the present application, the disclosures of which are incorporated by reference in their entirety herein.

FIELD

The present disclosure relates in exemplary embodiments to:
1) Transdermal delivery of microparticulate-based vaccines against
   a. Cancer (such as, but not limited to): melanoma, breast, ovarian cancer vaccines)
   b. Infectious diseases (such as, but not limited to: influenza, HPV, measles, meningitis, gonorrhea, RSV);
2) Potentiation of vaccine efficacy using probiotic microparticles;
3) Encapsulation of pancreatic beta cells for treatment of insulin dependent Diabetes Mellitus; and
4) Systems and methods for printing microneedles containing microencapsulated vaccines, drugs, or other bioactive materials using an automated 3D printer.

BRIEF DESCRIPTION OF THE DRAWINGS

The drawings disclose exemplary embodiments in which like reference characters designate the same or similar parts throughout the figures of which:

FIG. 45E shows release kinetics of the Spike S-1 protein from microparticles.

FIG. 45F shows release kinetics of the Spike protein from microneedles.

Figure 1:
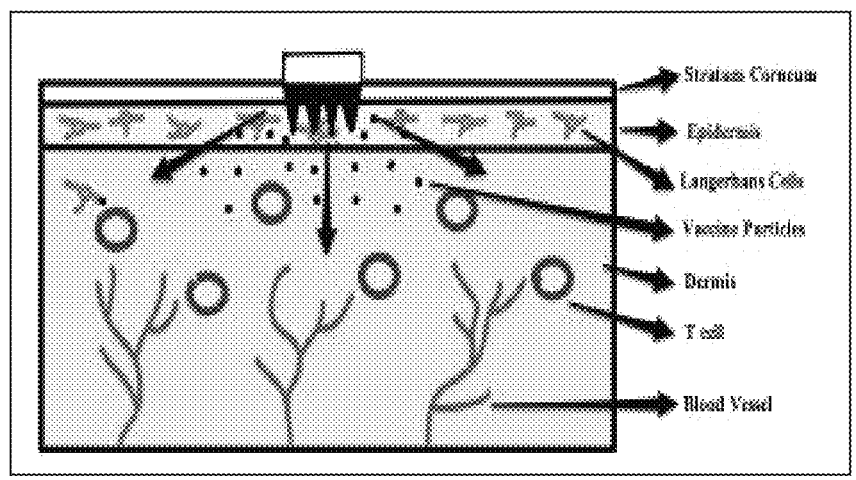
FIG. 1 illustrates a schematic of microneedle-mediated vaccination with microparticulate breast cancer vaccine.

The 67NR antigen loaded vaccine particles were formulated as follows. Briefly, HPMCAS and Eudragit® FS 30 D (1:1) were dissolved in an alkaline solution of pH above 7.0, followed by addition of 5% chitosan glycol. Bovine serum albumin in a ratio of 1:2 to enteric polymers was added to the polymeric solution at pH 7.0. Trehalose 5% and 0.25% AAL were also added to this solution (D'Souza et al., 2011). The 67NR antigen (WCL) was added at a 5% w/w loading. The aqueous feed mixture was gently stirred to result homogeneous feed solution. This aqueous feed solution was spray dried using Buchi B-191 Mini Spray Dryer (Buchi Corporation, DE) at inlet temperature 125° C., outlet temperature 80° C., 500 Nl/h, and 2% spray flow feed rate (10 ml per 30 min) of peristaltic pump, and nozzle diameter 0.7 mm (Do et al., 2010). The microparticles thus obtained were stored in desiccators at 4° C. till further use (Ref. No(s). (40)).

Characterization of Size, Shape and Charge of Microparticles

Spray dried microparticles were analyzed for their size and surface charge (zeta potential). Antigen loaded microparticles were suspended in citrate buffer (10 mM, pH 4.0) and particle size was measured using Spectrex laser particle counter (Spectrex Corp. CA). Zeta potential of these microparticles was measured using Malvern Zetasizer Nano ZS (Malvern Instruments, Worcs, UK). For morphology studies, vaccine microparticles were visualized by using scanning electron microscope. Specifically, particles were coated with gold. The coated samples were viewed under a scanning electron microscope (JEOL JSM 5800LV, JEOL USA, Peabody, Mass.) to reveal the surface quality and porosity of microparticles.

Content Analysis

To determine the total WCL protein content 5 mg of vaccine particles were dissolved in 1 mL of DPBS. The total WCL protein content of this solution was calculated using Bio-Rad DC protein assay. For the assay a standard curve was obtained using BSA standard from Bio-Rad and the protein content was analyzed as per the assay protocol.

Particle Cytotoxicity

Particles were tested for their cytotoxic properties using MTS assay (Promega), which determines cell viability in culture. RAW 264.7 cells (mouse leukemic monocyte macrophage cell line) were grown in DMEM medium, supplemented with 10% fetal bovine serum and 1% antibiotic in a cell culture flask. The cell culture media was then removed and cells were treated with 2 mL trypsin-EDTA. Thus, cells were detached from the cell culture flask and suspended in 1 mL complete DMEM media. Cell count of the resulting suspension was determined by trypan blue dye exclusion method using Bio-Rad counter (TC10™ Automated cell counter, Bio-Rad, CA). Cell suspension equivalent to 10,000 cells was plated in a 96 well cell culture plate and complete DMEM media was added to attain a volume of 100 μL per well. Plate was incubated for 24 h and various concentrations (2, 1, 0.5, 0.25, 0.125, 0.0625 mg/mL) of 4T07 antigen loaded particles were added to wells (n=3 for each concentration) and again incubated for 24 h. Cells treated with DMEM media alone were used as a negative control and cells treated with benzalkonium chloride (10 mg/ml) were chosen as a positive control (n=3 each). After 24 h, media was aspirated and 20 μL of MTS and phenazine methosulfate (PMS) solution was added (2 mL MTS sterile solution in PBS+100 μL of PMS sterile solution in PBS). The plate was incubated for 4 h at 37° C. in a humidified, 5% $CO_2$ chamber and absorbance was recorded at 490 nm using a UV plate reader (BioTek instruments Inc., VT).

In Vivo Evaluation

For in vivo studies, four to six week old Balb/c female mice were obtained from Charles River Laboratories (Wilmington, Mass., USA). The studies were conducted according to protocol approved by Mercer University's Institutional Animal Care and Use Committee (IACUC). For each vaccination study (4T07 and 67NR particulate vaccine), animals were divided in following seven groups: (a) animals receiving placebo microparticles via transdermal route, (b) animals administered with vaccine microparticles via transdermal route, (c) animals receiving placebo microparticles via subcutaneous route, (d) animals administered with vaccine microparticles via subcutaneous route, and (e) naïve animals (n=6 per group). All animals were pre-bled via tail vein to obtain basal antibody levels. Further, animals (except naïve animal group) were primed with 5 mg of either blank or vaccine microparticles (equivalent to 250 μg antigen) suspension in 200 μL of citrate buffer (10 mM, pH 4.0) using Dermaroller for transdermal route. One week after the prime dose, blood samples were collected from all the animals to analyze serum IgG, IgG1 and IgG2a antibody titers using ELISA. Six (4T07 vaccine) or nine (67NR vaccine) booster doses of same strength were given at an interval of two weeks from the prior dose and blood samples were collected a week after each dose to detect serum IgG levels. To perform antigen specific ELISA, whole cell lysate was used as capture antigen coated on a 96 well plate at a concentration of 50 μg/mL/well. For detection of (a) IgG: Serum samples from the study were used to detect the IgG levels at given time point. HRP (horseradish peroxidase) labeled secondary anti-mouse antibodies (Sigma Aldrich, MO) were used along with TMB (tetramethylbenzidine) substrate (BD Pharmingen, CA), reaction was stopped by adding 4N sulfuric acid and colored product was measured at 450 nm using a UV plate reader (BioTek instruments Inc., VT). (b) IgG1 and IgG2a: Serum samples after the last boosters were used to determine IgG subtypes titers (IgG1 and IgG2a). Serial dilutions (1:25, 1:50, 1:100 and 1:200) of the serum samples were prepared to detect IgG1 and IgG2a. Rabbit anti-mouse isotype specific antibodies (Sigma Aldrich, MO) were added to detect IgG1 and IgG2a respectively. Further goat anti-rabbit secondary antibody labeled with HRP was used along with TMB substrate. Reaction was stopped with 4N sulfuric acid and colored product was measured at 450 nm using UV plate reader.

Tumor Challenge

After the final booster, animals were challenged with $1 \times 10^6$ live 4T07/67NR cells subcutaneously to determine the efficacy of microparticulate vaccine. Briefly, cells were suspended in 100 μL of serum free DMEM media and injected subcutaneously using a 25-gauge needle at the back and between the ears of each animal. Each animal was monitored for tumor growth weekly. Tumor growth was measured using Vernier calipers and tumor volume was calculated according to the equation given below. Animals were observed for any signs of discomfort and tumor volumes were monitored for four weeks after challenge. Animals were sacrificed according to protocol approved by Mercer University IACUC.

$$\text{TumorVolume} = \frac{1}{2}\{\text{Length} \times (\text{Width})^2\}$$

Flow Cytometry Analysis to Elucidate Role of Immune Cells

After the final booster, animals were euthanized as per Mercer University IACUC protocol. Animals' abdominal cavities were excised open and spleens of these animals were isolated aseptically. Spleen samples from animals in the same group were pooled and processed. Briefly, the spleens were gently passed through a fine mesh resulting in a single cell suspension in RPMI-1640 media. Erythrocytes in this cell suspension were lysed by addition of ACK (ammonium chloride and potassium bi-carbonate) lysis buffer. Cell suspension was centrifuged to pellet the splenocytes and lysed erythrocytes in the supernatant were removed. Cell pellet was re-suspended in complete RPMI-1640 media and stored in −80° C. till further use. Splenocytes were cultured in complete RPMI-1640 media containing IL-2 (10 U/mL) for 1 day.

To identify the role of immune cells in 4T07 vaccine study, the murine breast cancer cells (4T07) were cultured in complete DMEM media separately and treated with mitomycin C (25 ug/mL for $10^7$ cancer cells) for 30 min and then washed thrice by centrifuging the cell suspension at 1000 rpm for 10 min each. Cultured splenocytes were then added to mitomycin C treated cancer cells having IL-2 (10 U/mL) enriched RPMI-1640 and DMEM media in 1:1 ratio. The co-culture was incubated at 37° C., 5% $CO_2$ for 3 days and then the stimulated splenocytes (non-adherent) were removed and centrifuged at 1000 rpm for 10 min. Splenocyte pellet was re-constituted in 1 mL Hanks balanced salt solution and total cell count was determined by trypan blue dye exclusion method using a Bio-Rad TC2 cell counter. This cell suspension was divided in following equal parts based on the total viable cell count: a) No markers were added to first part, this serves as the negative control for various cell populations to be analyzed. b) Anti-CD4+PE (for T-helper cell) and anti-CD8+FITC (for T-cytotoxic cell) markers, c) anti-CD45R (B220) marker (for B cells) and d) anti-CD161 marker (for NK cells). All the markers were added as per manufacturer's protocol. All the samples were incubated on ice for 30 min and subjected to analysis using BD Accuri® C6 flow cytometer (BD Accuri Cytometers, MI) to analyze various cell populations in vaccinated and control groups. To elucidate the role of immune cells in the 67NR vaccination study, macrophage-splenocyte overlay assay was performed. The assay involved priming murine RAW 264.7 macrophages with 67NR whole cell lysate for 24 h and then co-culturing with splenocytes in IL-2 rich RPMI and DMEM (1:1) medium for 5 days at 37° C. and 5% $CO_2$ in the incubator. The primed splenocytes were processed as mentioned before and were subjected to analysis using BD Accuri® C6 flow cytometer.

Statistical Analysis

The data was analyzed using either one-way ANOVA or student t-test to assess statistical significance. A p-value of less than 0.05 was considered to be statistically significant.

Results

Quantification of Lysate

Total protein concentration of WCL as obtained from $7\text{-}10 \times 10^6$ 4T07/67NR cells using total protein DC Bio-Rad assay was found to range from 10-14 mg/5 mL with a concentration of 2.0-3.0 mg/mL. This concentration was further utilized to quantify the volume of lysate required for 5% w/w antigen loading in microparticle matrix and 50 μg/mL/well for ELISA studies.

Characterization of Size, Shape and Charge of Microparticles

Figure 2:
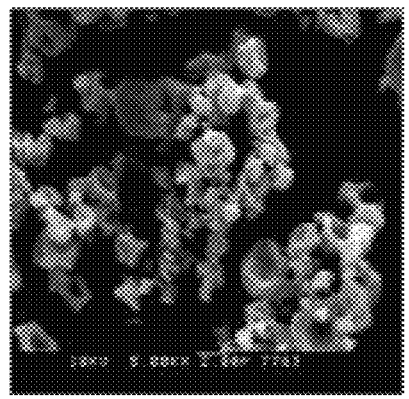
FIG. 2 illustrates a scanning electron microscopy image of 4T07 and 67NR vaccine microparticles, respectively.

The yield of spray drying process was within a range of 72-80% w/w. The surface morphology of the 4T07 vaccine particles was rough and of irregular shape, while the 67NR vaccine particles were doughnut shaped with smooth edges as seen in the scanning electron micrograph in FIG. 2. Particle size analysis using Spectrex laser counter indicated an average particle size of 1.5 μm with particles of size range of 1-4 μm as shown in FIG. 2. The zeta potential was neutral, ranging from +4 to +7 mV for the 4T07 vaccine particles while it was +14 to +17 mV for 67NR particles.

FIG. 2 shows a scanning electron microscopy image of 4T07 and 67NR vaccine microparticles, respectively.

Figure 3:
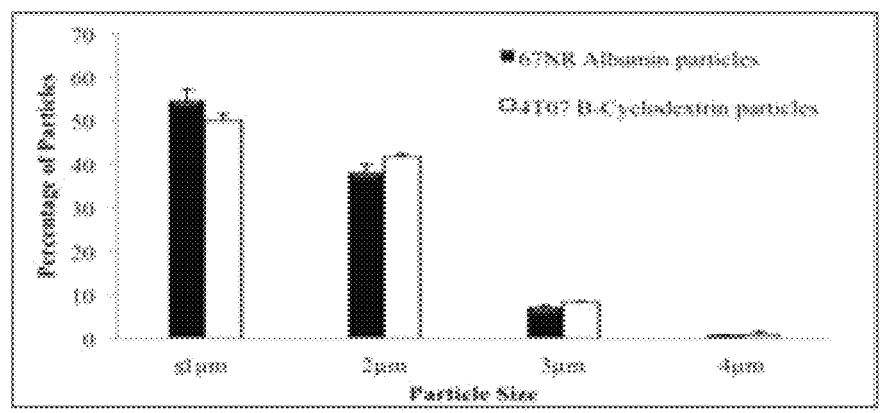
FIG. 3 illustrates a particle size distribution of vaccine microparticles as measured by Spectrex laser counter in triplicates. Results are expressed as mean±SE.

FIG. 3 shows particle size distribution of vaccine microparticles as measured by Spectrex laser counter in triplicates. Results are expressed as mean±SE.

Content Analysis

The antigen content of the 4T07 antigen particles was 86±2.5% w/w. The antigen content of 67NR particles was 88±6.0% w/w. Content analysis was performed in triplicates; reported result includes the standard error values.

Cytotoxicity Study

Figure 4:
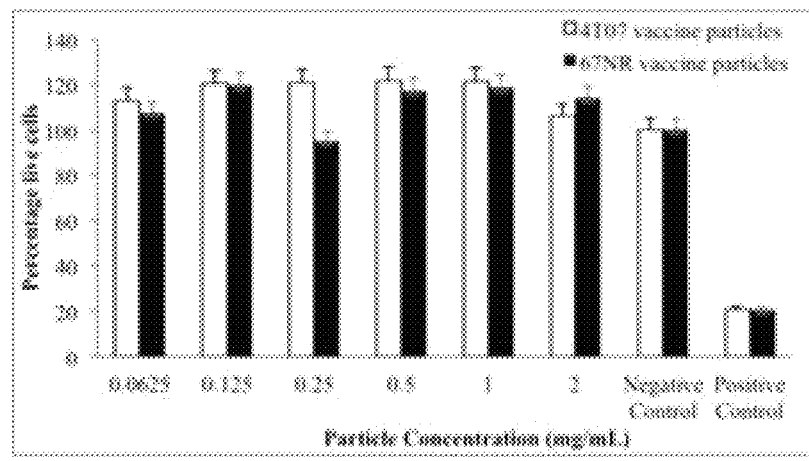
FIG. 4 illustrates a MTS cell cytotoxicity assay performed with various concentrations of both vaccine microparticles, cells alone as negative control and benzalkonium chloride (10 mg/mL) treated cells as positive control tested in triplicates. Vaccine particles were non-cytotoxic for tested concentrations. Results are expressed as mean±SE.

Cytotoxic effect of particles at given concentrations is depicted in FIG. 4. Particles were non-cytotoxic within the tested concentration range (0.0625-2 mg/mL). Percentage cytotoxicity is relative to negative controls of cells treated with DMEM media only. Positive control of benzalkonium chloride was cytotoxic with 21% cell viability. Thus, the combination of formulation polymers in the given ratio at tested concentrations was not cytotoxic and thus was used for further studies.

FIG. 4 shows MTS cell cytotoxicity assay performed with various concentrations of both vaccine microparticles, cells alone as negative control and benzalkonium chloride (10 mg/mL) treated cells as positive control tested in triplicates. Vaccine particles were non-cytotoxic for tested concentrations. Results are expressed as mean±SE.

Figure 5:
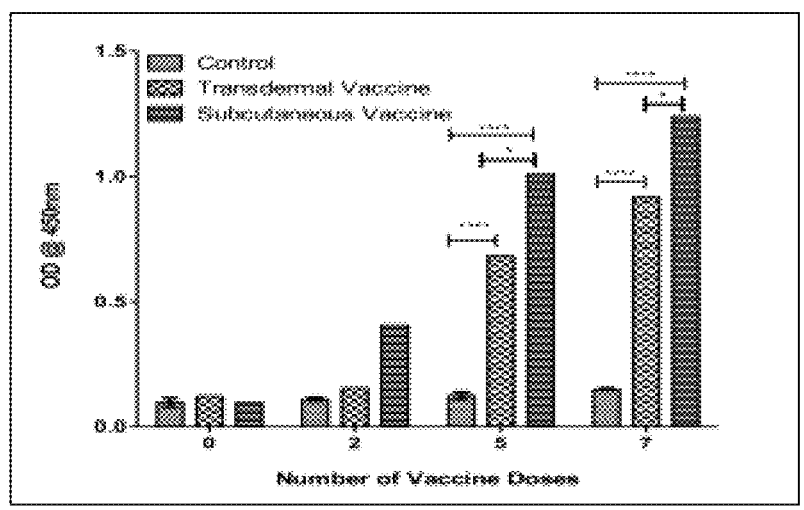
FIG. 5 illustrates a flowchart diagram combining the content based filtering techniques with the collaborative filtering techniques to return a list of customized purchase recommendations.

FIG. 5 shows serum IgG titres of vaccinated and control animals after different number of booster doses.

Figure 6:
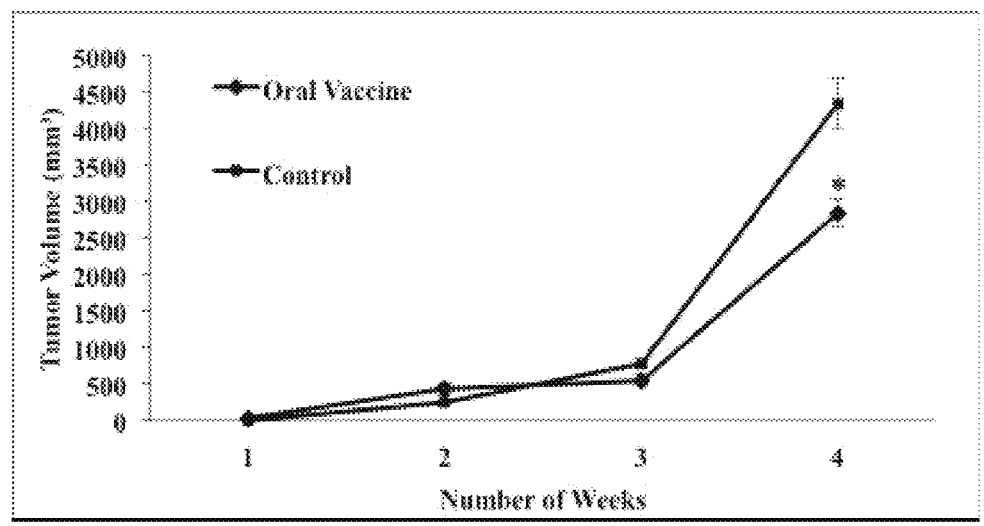
FIG. 6 illustrates a tumor volumes of vaccinated and control animals as measured post challenge with live 4T07 cancer cells. Vaccinated animals had significantly smaller tumor volumes than controls *($p<0.05$) (n=6). Results are expressed as mean±SE.

FIG. 6 shows tumor volumes of vaccinated and control animals as measured post challenge with live 4T07 cancer cells. Vaccinated animals had significantly smaller tumor volumes than controls *($p<0.05$) (n=6). Results are expressed as mean±SE.

Figure 7:
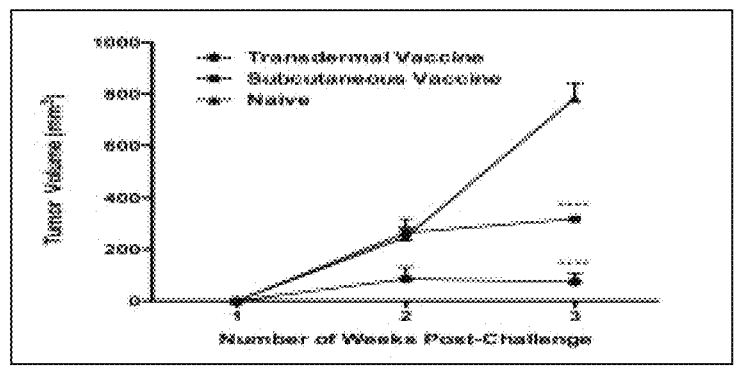
FIG. 7 illustrates a tumor volumes in vaccinated and control animal's weeks after challenge.

FIG. 7 shows tumor volumes in vaccinated and control animal's weeks after challenge.

Figure 8:
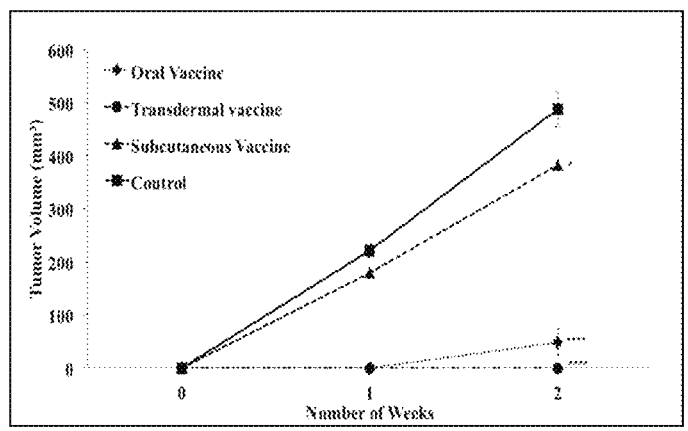
FIG. 8 illustrates a 67NR vaccinated animals via oral and transdermal routes showed protection from the tumor challenge for two weeks compared to controls. *$p<0.05$, ****$p<0.0001$.

FIG. 8 shows 67NR vaccinated animals via oral and transdermal routes showed protection from the tumor challenge for two weeks compared to controls. *$p<0.05$, ****$p<0.0001$.

REFERENCES FOR EXAMPLE 1

1. Finn O J, Forni G. Prophylactic cancer vaccines. Current opinion in immunology. 2002 April; 14(2):172-7.
2. Arlen P M, Madan R A, Hodge J W, Schlom J, Gulley J L. Combining Vaccines with Conventional Therapies for Cancer. Update on cancer therapeutics. 2007 March; 2(1): 33-9.
3. Tartaglia J, Bonnet M C, Berinstein N, Barber B, Klein M, Moingeon P. Therapeutic vaccines against melanoma and colorectal cancer. Vaccine. 2001 Mar. 21; 19(17-19):2571-5.
4. Anderson R J, Schneider J. Plasmid DNA and viral vector-based vaccines for the treatment of cancer. Vaccine. 2007 Sep. 27; 25 Suppl 2:B24-34.
5. Sheng W Y, Huang L. Cancer Immunotherapy and Nanomedicine. Pharmaceutical research. September 4.
6. O'Hagan D T, Singh M. Microparticles as vaccine adjuvants and delivery systems. Expert Rev Vaccines. 2003 April; 2(2):269-83.
7. Malik B, Goyal A K, Markandeywar T S, Rath G, Zakir F, Vyas S P. Microfold-cell targeted surface engineered polymeric nanoparticles for oral immunization. J Drug Target. 2012 January; 20(1):76-84.
8. Mittendorf E A, Alatrash G, Xiao H, Clifton G T, Murray J L, Peoples G E. Breast cancer vaccines: ongoing National Cancer Institute-registered clinical trials. Expert Rev Vaccines. 2011 June; 10(6):755-74.
9. Curigliano G, Locatelli M, Fumagalli L, Goldhirsch A. Immunizing against breast cancer: a new swing for an old sword. Breast. 2009 October; 18 Suppl 3:S51-4.
10. Patil R, Clifton G T, Holmes J P, Amin A, Carmichael M G, Gates J D, et al. Clinical and immunologic responses of HLA-A3+ breast cancer patients vaccinated with the HER2/neu-derived peptide vaccine, E75, in a phase I/II clinical trial. J Am Coll Surg. 2010 February; 210(2): 140-7.
11. Park J W, Melisko M E, Esserman L J, Jones L A, Wollan J B, Sims R. Treatment with autologous antigen-presenting cells activated with the HER-2 based antigen Lapuleucel-T: results of a phase I study in immunologic and clinical activity in HER-2 overexpressing breast cancer. J Clin Oncol. 2007 Aug. 20; 25(24):3680-7.
12. Peethambaram P P, Melisko M E, Rinn K J, Alberts S R, Provost N M, Jones L A, et al. A phase I trial of immunotherapy with lapuleucel-T (APC8024) in patients with refractory metastatic tumors that express HER-2/neu. Clin Cancer Res. 2009 Sep. 15; 15(18):5937-44.
13. Mittendorf E, Holmes J, Ponniah S, Peoples G. The E75 HER2/neu peptide vaccine. Cancer Immunol Immunother. 2008 October; 57(10):1511-21.
14. Pulendran B, Banchereau J, Maraskovsky E, Maliszewski C. Modulating the immune response with dendritic cells and their growth factors. Trends Immunol. 2001 Jan. 22(1):41-7.
15. Akande J, Yeboah K G, Addo R T, Siddig A, Oettinger C W, D'Souza M J. Targeted delivery of antigens to the gut-associated lymphoid tissues: 2. Ex vivo evaluation of lectin-labeled albumin microspheres for targeted delivery of antigens to the M-cells of the Peyer's patches. J Microencapsul. 2010; 27(4):325-36.
16. Lai Y H, D'Souza M J. Microparticle transport in the human intestinal M cell model. Journal of drug targeting. 2008 January; 16(1):36-42.
17. Andrianov A K, Payne L G. Polymeric carriers for oral uptake of microparticulates. Adv Drug Deliv Rev. 1998 Dec. 1; 34(2-3):155-70.
18. Vyas S P, Gupta P N. Implication of nanoparticles/microparticles in mucosal vaccine delivery. Expert Rev Vaccines. 2007 June; 6(3):401-18.
19. Xiang S D, Scholzen A, Minigo G, David C, Apostolopoulos V, Mottram P L, et al. Pathogen recognition and development of particulate vaccines: does size matter? Methods (San Diego, Calif. 2006 September; 40(1):1-9.
20. Men Y, Audran R, Thomasin C, Eberl G, Demotz S, Merkle H P, et al. MHC class I- and class II-restricted processing and presentation of microencapsulated antigens. Vaccine. 1999 Mar. 5; 17(9-10):1047-56.
21. Shen H, Ackerman A L, Cody V, Giodini A, Hinson E R, Cresswell P, et al. Enhanced and prolonged cross-presentation following endosomal escape of exogenous antigens encapsulated in biodegradable nanoparticles. Immunology. 2006 January; 117(1):78-88.
22. Hori M, Onishi H, Machida Y. Evaluation of Eudragit-coated chitosan microparticles as an oral immune delivery system. Int J Pharm. 2005 Jun. 13; 297(1-2):223-34.
23. Lai Y H, D'Souza M J. Formulation and evaluation of an oral melanoma vaccine. J Microencapsul. 2007 May; 24(3):235-52.
24. Bodmeier R, Chen H G, Paeratakul O. A novel approach to the oral delivery of micro- or nanoparticles. Pharmaceutical research. 1989 May; 6(5):413-7.
25. Delgado A, Lavelle E C, Hartshorne M, Davis S S. PLG microparticles stabilised using enteric coating polymers as oral vaccine delivery systems. Vaccine. 1999 Jul. 16; 17(22):2927-38.
26. Haddadi A, Farboud E S, Erfan M, Aboofazeli R. Preparation and characterization of biodegradable urea-loaded microparticles as an approach for transdermal delivery. J Microencapsul. 2006 September; 23(6):698-712.
27. Jain D, Panda A K, Majumdar D K. Eudragit S100 entrapped insulin microspheres for oral delivery. AAPS PharmSciTech. 2005; 6(1):E100-7.
28. O'Hagan D T. Microparticles and polymers for the mucosal delivery of vaccines. Adv Drug Deliv Rev. 1998 Dec. 1; 34(2-3):305-20.
29. Nellore R V, Pande P G, Young D, Bhagat H R. Evaluation of biodegradable microspheres as vaccine adjuvant for hepatitis B surface antigen. J Parenter Sci Technol. 1992 September-October; 46(5): 176-80.
30. Bhowmik T, D'Souza B, Uddin M N, D'Souza M J. Oral delivery of microparticles containing plasmid DNA encoding hepatitis-B surface antigen. J Drug Target Epub DOI: 103109/1061186X2012662686. 2012 Feb. 18.
31. D'Souza B, Bhowmik T, Shashidharamurthy R, Oettinger C, Selvaraj P, D'Souza M. Oral microparticulate vaccine for melanoma using M-cell targeting. J Drug Target. 2011 Oct. 10; 20(2):166-73.
32. Chablani L, Tawde S A, D'Souza M J. Spray-dried microparticles: a potential vehicle for oral delivery of vaccines. J Microencapsul Epub DOI: 103109/026520482011651503. 2012 Jan. 27.
33. Baras B, Benoit M, Poulain-Godefroy O, Schacht A, Capron A, Gillard J, et al. Vaccine properties of antigens entrapped in microparticles produced by spray-drying technique and using various polyester polymers. Vaccine. 2000 Feb. 14; 18(15):1495-505.
34. Bhowmik T, D'Souza B, Shashidharamurthy R, Oettinger C, Selvaraj P, D'Souza M J. A novel microparticulate vaccine for melanoma cancer using transdermal delivery. J Microencapsul. 2011; 28(4):294-300.
35. Millqvist-Fureby A, Malmsten M, Bergenstahl B. Spray-drying of trypsin-surface characterisation and activity preservation. Int J Pharm. 1999 Oct. 25; 188(2):243-53.

36. Pickard J M, Chervonsky A V. Sampling of the intestinal microbiota by epithelial M cells. Curr Gastroenterol Rep. 2010 October; 12(5):331-9.

37. Malik B, Goyal A K, Mangal S, Zakir F, Vyas S P. Implication of gut immunology in the design of oral vaccines. Curr Mol Med. 2010 February; 10(1):47-70.

38. Mahmoud S M, Lee A H, Paish E C, Macmillan R D, Ellis I O, Green A R. The prognostic significance of B lymphocytes in invasive carcinoma of the breast. Breast Cancer Res Treat. 2012 April; 132(2):545-53.

39. Roth-Walter F, Bohle B, Scholl I, Untersmayr E, Scheiner O, Boltz-Nitulescu G, et al. Targeting antigens to murine and human M-cells with *Aleuria aurantia* lectin-functionalized microparticles. Immunol Lett. 2005 Sep. 15; 100(2):182-8.

40. Morello M, Krone C L, Dickerson S, Howerth E, Germishuizen W A, Wong Y L, et al. Dry-powder pulmonary insufflation in the mouse for application to vaccine or drug studies. Tuberculosis (Edinb). 2009 September; 89(5):371-7.

41. Esposito E, Menegatti E, Cortesi R. Hyaluronan-based microspheres as tools for drug delivery: a comparative study. Int J Pharm. 2005 Jan. 6; 288(1):35-49.

42. Zolnik B S, Raton J L, Burgess D J. Application of USP Apparatus 4 and In Situ Fiber Optic Analysis to Microsphere, Special Edition on Flow Through Cell, USP Apparatus 4. Dissolution Technologies. 2005; 12:11-4.

43. Wright A, Mowrey-McKee M. Comparative cytotoxicity potential of soft contact lens care products. Cutan Ocul Toxicol. 2005; 24(1):53-64.

44. Primard C, Rochereau N, Luciani E, Genin C, Delair T, Paul S, et al. Traffic of poly(lactic acid) nanoparticulate vaccine vehicle from intestinal mucus to sub-epithelial immune competent cells. Biomaterials. 2010 August; 31(23):6060-8.

45. Lamprecht A, Yamamoto H, Takeuchi H, Kawashima Y. Microsphere design for the colonic delivery of 5-fluorouracil. J Control Release. 2003 Jul. 31; 90(3):313-22.

46. Kaushik J K, Bhat R. Why is trehalose an exceptional protein stabilizer? An analysis of the thermal stability of proteins in the presence of the compatible osmolyte trehalose. J Biol Chem. 2003 Jul. 18; 278(29):26458-65.

47. Do D P, Pai S B, Rizvi S A, D'Souza M J. Development of sulforaphane-encapsulated microspheres for cancer epigenetic therapy. Int J Pharm. 2010 Feb. 15; 386(1-2):114-21.

48. Shakweh M, Besnard M, Nicolas V, Fattal E. Poly(lactide-co-glycolide) particles of different physicochemical properties and their uptake by peyer's patches in mice. Eur J Pharm Biopharm. 2005 September; 61(1-2):1-13.

49. Chin C S, Bear H D. Sentinel node mapping identifies vaccine-draining lymph nodes with tumor-specific immunological activity. Ann Surg Oncol. 2002 January-February; 9(1):94-103.

50. Gravekamp C, Sypniewska R, Hoflack L. The usefulness of mouse breast tumor models for testing and optimization of breast cancer vaccines at old age. Mech Ageing Dev. 2004 February; 125(2):125-7.

51. Heppner G H, Miller F R, Shekhar P M. Nontransgenic models of breast cancer. Breast Cancer Res. 2000; 2(5):331-4.

52. Anode G, Hegde R, Mani A, Jin Y, Chebloune Y, Narayan O. Phenotypic and functional analysis of immune CD8+ T cell responses induced by a single injection of a HIV DNA vaccine in mice. J Immunol. 2007 Feb. 15; 178(4):2318-27.

53. Parviz M, Chin C S, Graham L J, Miller C, Lee C, George K, et al. Successful adoptive immunotherapy with vaccine-sensitized T cells, despite no effect with vaccination alone in a weakly immunogenic tumor model. Cancer Immunol Immunother. 2003 December; 52(12):739-50.

54. Chiang C L, Benencia F, Coukos G. Whole tumor antigen vaccines. Semin Immunol. 2010 June; 22(3):132-43.

55. Solbrig C M, Saucier-Sawyer J K, Cody V, Saltzman W M, Hanlon D J. Polymer nanoparticles for immunotherapy from encapsulated tumor-associated antigens and whole tumor cells. Mol Pharm. 2007 January-February; 4(1):47-57.

56. Estevan M, Irache J M, Grillo M J, Blasco J M, Gamazo C. Encapsulation of antigenic extracts of *Salmonella enterica* serovar. Abortusovis into polymeric systems and efficacy as vaccines in mice. Vet Microbiol. 2006 Nov. 26; 118(1-2):124-32.

57. Tuohy V K, Jaini R. Prophylactic cancer vaccination by targeting functional non-self. Ann Med. 2011 August; 43(5):356-65.

58. Tuohy V K. A prophylactic vaccine for breast cancer? Why not? Breast Cancer Res. 2010; 12(6):405.

59. Jaini R, Kesaraju P, Johnson J M, Altuntas C Z, Jane-Wit D, Tuohy V K. An autoimmune-mediated strategy for prophylactic breast cancer vaccination. Nat Med. 2010 July; 16(7):799-803.

60. Gayakwad S G, Bejugam N K, Akhavein N, Uddin N A, Oettinger C E, D'Souza M J. Formulation and in vitro characterization of spray-dried antisense oligonucleotide to NF-kappaB encapsulated albumin microspheres. J Microencapsul. 2009 December; 26(8):692-700.

61. Uddin A N, Bejugam N K, Gayakwad S G, Akther P, D'Souza M J. Oral delivery of gastro-resistant microencapsulated typhoid vaccine. J Drug Target. 2009 August; 17(7):553-60.

62. Uddin M N, Do D P, Pai S B, Gayakwad S, Oettinger C W, D'Souza M J. A methodology for quantitation and characterization of oligonucleotides in albumin microspheres. Analyst. 2009 July; 134(7):1483-9.

63. Yeboah K G, D'Souza M J. Evaluation of albumin microspheres as oral delivery system for Mycobacterium tuberculosis vaccines. J Microencapsul. 2009 March; 26(2):166-79.

64. Manmohan S. Vaccine adjuvants and delivery systems. Hoboken, N.J.: Wiley-Interscience; 2007.

65. Brayden D J. Oral vaccination in man using antigens in particles: current status. Eur J Pharm Sci. 2001 October; 14(3):183-9.

66. O'Hagan D T. Novel delivery systems for oral vaccines. Boca Raton: CRC Press; 1994.

67. Goldsby R A. Immunology. 5th ed. New York: W.H. Freeman; 2003.

68. Carcaboso A M, Hernandez R M, Igartua M, Rosas J E, Patarroyo M E, Pedraz J L. Potent, long lasting systemic antibody levels and mixed Th1/Th2 immune response after nasal immunization with malaria antigen loaded PLGA microparticles. Vaccine. 2004 Mar. 29; 22(11-12):1423-32.

69. Marzo A L, Lake R A, Robinson B W, Scott B. T-cell receptor transgenic analysis of tumor-specific CD8 and CD4 responses in the eradication of solid tumors. Cancer Res. 1999 Mar. 1; 59(5):1071-9.

70. Perez-Diez A, Joncker N T, Choi K, Chan W F, Anderson C C, Lantz O, et al. CD4 cells can be more efficient at tumor rejection than CD8 cells. Blood. 2007 Jun. 15; 109(12):5346-54.

Example 2

Ovarian Cancer Vaccine

Introduction

Ovarian cancer is the most lethal gynecological cancer and the fifth most leading cause of cancer related deaths in women in the US. The National Cancer Institute (NCI) reports 22,280 new cases and 15,500 deaths due to ovarian cancer in the US in 2012 (7). Since it is very difficult to detect an ovarian cancer, especially in the early stages, it is referred to as a 'silent killer'. Only about 10% of ovarian cancers are usually found in the early stages. Patients with epithelial tumors, which account for approximately 90% of ovarian cancer, generally have poor overall survival and the 5-year survival for stages III-IV of these tumors is about 29.1% (8). The first-line treatment for advanced ovarian cancer involves surgery to remove the tumor, followed by chemotherapy. However, the cancer relapses within relatively short periods of time even after treatment. It has been reported that up to 75% of patients responding well to the initial treatments face tumor relapse within 18-28 months (8, 9). Moreover, chemotherapeutic treatments for cancer are toxic and/or of minimal therapeutic value. Therefore, alternative approaches such as immunotherapy is being investigated to prevent relapse of cancer.

Several vaccines are underway in clinical trials and most of them have not progressed beyond phase I/II studies. It has been observed that even though antigen-specific response is obtained with different approaches of antigen specific immunization, there is no consistency in clinical benefit (9, 10). Therefore, there is no ovarian cancer vaccine commercially available to date. Recently a therapeutic prostate cancer (Provenge®) was introduced into the market in April 2010 by Dendreon Corporation (Seattle, Wash.), which involves isolating white blood cells from prostate cancer patients and stimulating them ex-vivo. The cells are activated with a prostate-specific fusion protein are then re-introduced into the patient. This procedure when carried out three times was found to result in marginal increase in median survival rate of prostate cancer patients by 4 months in clinical trials and the cost for the vaccine is $93,000. Our approach, addresses many of the problems associated with the current vaccine therapies such as time involved in vaccine preparation, specific antigen isolation/purification including the high vaccine costs. In the present study, we demonstrate the efficacy of the vaccine formulations which was evaluated in vivo in mouse tumor model, using the ID8 murine ovarian cancer cell line as a solid tumor model (32). A murine ovarian cancer cell line, ID8 was used as a source of antigens as it correlates closely to human ovarian cancer cell lines in signaling pathways and results in development of tumor in mice models similar to human ovarian cancer. Thus, ID8 cell line provides a unique and important new model to study the immune response developed by the vaccine against the initiation and progression of ovarian cancer in mice with an intact immune system (31, 32). Although specific antigen cancer vaccines are now commonly used due to advancement in recombinant technology and gene expression, the whole cell lysate vaccine still remains a very promising approach as it can overcome the demerits associated with a single antigen/epitope vaccine. Whole cell lysate provides a pool of tumor-associated antigens (TAAs) which can induce both CD8+ and CD4+ T cells. Necrotic whole cell lysate is widely used approach to prepare a pool of antigens which can be obtained by multiple freeze-thaw cycles (11). Therefore, we proceeded with a whole cell lysate of ID8 cells to prepare the vaccine for this study. Transdermal delivery was achieved using a Dermaroller comprised of an array of metallic microneedles In addition, we studied the vaccine efficacy via therapeutic approach, where the vaccine was administered after tumor induction in mice. For this study, we injected tumor via intraperitoneal route which allows development of tumor lesions, ascetic fluids and nodules in peritoneal cavity of mice as seen in human patients. This was done to mimic the real-time scenario, where patients with post-surgical residual tumors will receive such vaccine as a therapy.

Materials and Methods

Materials

Six to eight week-old C57BL/6 female mice were purchased from Charles River Laboratories, Wilmington, Mass. Dulbecco's Modified Eagle Medium (DMEM), fetal bovine serum (FBS), RPMI-1640 medium and Dulbecco's phosphate buffer saline (DPBS) were purchased from Atlanta Biologicals, Atlanta, Ga. Hydroxyl propyl methyl cellulose acetate succinate (HPMCAS) was purchased from AQOAT, FMC Biopolymers, Philadelphia, Pa. Eudragit® FS 30 D, Evonik industries, Parsippany, N.J. Mouse plasma was obtained from Biochemed, Winchester, Va. *Aleuria aurantia* lectin (AAL) was obtained from Vector Labs, Inc., Burlingame, Calif. Recombinant murine interleukins, IL-2 (specific activity of $\geq 5 \times 10^6$ units/mg) and IL-12 (specific activity of $\geq 1 \times 10^7$ units/mg) were purchased from Peprotech Inc., Rocky Hill, N.J. Chitosan glycol, trehalose and Insulin-transferrin-sodium selenite media supplement were obtained from Sigma, St. Louis, Mo. Flow cytometry cell markers, anti-mouse CD4 PE, anti-mouse CD8a FITC, anti-mouse NK and anti-mouse/human CD45R (B220) FITC were purchased from eBioscience, San Diego, Calif. The goat anti-mouse HRP-IgG and anti-IgG subtypes were purchased from Bethyl Laboratories, Montgomery, Tex. and Sigma, St. Louis, Mo. respectively.

Whole Cell Lysate of ID8 Ovarian Cancer Cell Line

Preparation of Whole Cell Lysate of ID8 Ovarian Cancer Cell Line

The murine ovarian cancer ID8 cells were cultured in Dulbecco's Modified Eagles Medium (DMEM) supplemented with 4% fetal bovine serum, penicillin/streptomycin solution (Sigma, St. Louis, Mo.), 5 μg/ml insulin, 5 μg/ml transferrin and 5 ng/ml sodium selenite (Insulin-transferrin-sodium selenite media supplement, Sigma, St. Louis, Mo.) (31, 32). They were maintained at 37° C. in a humidified incubator with 5% $CO_2$ atmosphere until they were 90% confluent. Whole cell lysate was prepared using hypotonic lysis buffer (10 mM Tris and 10 mM NaCl). Briefly, the cells were washed with cold phosphate buffered saline (PBS), pH 7.4 six times. The flasks were then treated with hypotonic buffer and subjected to five 15 min freeze-thaw cycles at temperatures of −80° C. and 37° C. respectively to obtain the cell lysate (11). The lysate obtained was stored at −80° C. until used.

Preparation and Characterization of Vaccine Microparticles

Preparation of Vaccine Microparticles

The vaccine formulation was prepared by using spray drying technique described elsewhere (33-42). Briefly, hydroxyl propyl methyl cellulose acetate succinate (HPMC-AS) and Eudragit® FS 30D were dissolved in an alkaline solution, followed by addition of chitosan glycol. Mouse plasma was added to the polymeric solution at pH 7.0 as a source of albumin. Trehalose, tween 20 and AAL were added to the solution. Whole cell lysate obtained from ID8 cells (5% w/w) was added to this feed mixture and temperature was maintained at 4° C. throughout the spraying. In case of vaccine with interleukins formulations, interleukins IL-2 and IL-12 (0.025% w/w each corresponding to specific activity of $4\times10^5$ U for IL-2 and $8\times10^5$ U for IL-2) were added to this feed mixture (42). This aqueous solution was spray dried using Buchi B-191 Mini Spray Dryer (Buchi Corporation, New Castle, Del.). The microparticles obtained were stored in desiccators at $-20°$ C. Each preparation was carried out in triplicates. Product yield was calculated as the weight percentage of the microparticles obtained as the final product in comparison to the total solid content of the materials sprayed.

Characterization of Vaccine Microparticles

Average Diameter and Particle Size Distribution

The particles were characterized for size and charge, using laser particle counter (Spectrex PC-2000) (n=3) and Malvern zeta sizer (ZEN 1600) (n=10) respectively. The particles were suspended in citrate buffer, pH 4.0 and the average diameter was reported as a volumetric mean diameter, (n=3), and the particle size distribution was evaluated by span value, defined as the following expression:

Span Value=$D$90%–$D$10%

D50% where, DN % means that the diameter of microparticles exhibited by N % of total microparticles, where N=10, 50 or 90. The lesser the span value, the narrower the particle size distribution (33).

Loading Efficiency

To determine loading efficiency, 5 mg of the microparticles were accurately weighed and added to 1 mL of 1×PBS, pH 7.4 at room temperature. Proteins were allowed to extract in PBS as the enteric particles dissolved at pH 7.0. The extracted solution was analyzed for total lysate protein content using Biorad DC™ protein assay (Biorad, Hercules, Calif.) in comparison to placebo particles.

Administration of Vaccine Microparticles

The immunogenicity of microparticulate vaccine was evaluated using C57BL/6 female mice model. Six to eight week-old C57BL/6 mice were purchased from Charles River Laboratories, Wilmington, Mass. and the animals were acclimatized for one week prior use. The animal experiments were carried out as per approved protocols by Mercer University's Institutional Committee for the care and Use of Laboratory animals (IACUC).

Animals (n=8) were administered with microparticles as one prime dose followed by one booster after one week and thereafter by 8 boosters with an interval of two weeks. Briefly, 5 mg of microparticles were suspended in 0.3 ml citrate buffer (pH 4.0) and administered orally using oral gavage. For delivering microparticles via transdermal route, mice skin was shaved two days prior to vaccination. Around 5 mg of microparticles were suspended in citrate buffer, pH 4.0 containing PEG 8000 as a viscosity modifier. These mice were vaccinated by delivering this microparticles using a Dermaroller. For subcutaneous route, 5 mg of microparticles were suspended in citrate buffer and administered using 26.5 G needle.

Three groups of animals (n=8 each) were administered with following three formulations:
 1. Vaccine microparticles
 2. Vaccine microparticles with interleukins, IL-2 and IL-12
 3. Placebo microparticles (control group)

Blood samples of these treated animals were collected prior to immunization and centrifuged at 14000 rpm for 15 mins. The serum was separated and stored at $-80°$ C. until further use.

Tumor Challenge and Tumor Volume Measurements

One week after the last vaccination, the mice were challenged s.c. with $1\times10^7$ live ID8 cells (32, 42). Live cell count was determined using trypan blue exclusion by TC10™ automated cell counter (Biorad, Hercules, Calif.). The cells were suspended in 200 µl of incomplete media and injected into the right back flank of C57BL/6 female mice using a 26 G needle. Tumor development was monitored using digital vernier calipers. Two perpendicular diameters were measured every week with vernier calipers to calculate tumor volume. The mice were euthanized whenever the tumor ulcerated or tumors exceeded a size of 15 mm in any of the perpendicular diameters or mice showed signs of discomfort. The tumor volume (V) was determined by using the formula, $V=\frac{1}{2}LW^2$, where L is the length and W is the width of tumor (42).

Therapeutic Vaccine Efficacy in Tumor Bearing Mice

Tumor Induction

To induce tumor, $2\times10^6$ of live tumor cells, ID8 were injected intraperitoneally (i.p.) to all animals. Live cell count was determined using trypan blue exclusion by TC10™ automated cell counter (Biorad, Hercules, Calif.). The cells were suspended in 200 µl of incomplete media and injected into the peritoneal cavity of C57BL/6 female mice using a 26 G needle.

Administration of Vaccine Microparticles and Tumor Measurements

The therapeutic efficacy of microparticulate vaccine was evaluated using C57BL/6 female mice model. Six to eight week-old C57BL/6 mice were purchased from Charles River Laboratories, Wilmington, Mass. and the animals were acclimatized for one week prior use. The animal experiments were carried out as per approved protocols by Mercer University's Institutional Committee for the care and Use of Laboratory animals (IACUC).

After one week of tumor induction, the mice (n=8) were vaccinated at an interval of two weeks with 5 mg of vaccine microparticles (equivalent to 250 µg ID8 lysate proteins) suspended in citrate buffer (10 mM, pH 4.0) using oral feeding needle, Dermaroller and 26 gauge needle for transdermal and subcutaneous respectively. The vaccination was continued until the tumor volume in terms of diameter of mice exceeds 40 mm. Tumor development was monitored by measuring dorsal diameter and recording the total body weight of mice. The mice were euthanized whenever the tumors exceeded a size of 40 mm in dorsal diameters or mice showed signs of discomfort.

Results

Preparation and Characterization of Lysate of ID8 Ovarian Cancer Cell Line

In order to obtain a source of antigens, the whole cell lysate provides a full array of tumor associated antigens (TAAs) without the need of characterizing all the antigens which minimizes the chance of tumor escape. In this study, we prepared a microparticulate vaccine using whole cell lysate obtained from ID8 murine ovarian cancer cells. In terms of translatability to human ovarian cancer, the mouse ID8 ovarian cancer cell line shows several similar markers of human ovarian cancer such as Src, FAK and Akt. The constitutive activation of Src, FAK, PI3-kinase (phosphatidylinositol-3-kinase), and Akt/PKB as seen in ID8 cells and human ovarian tumor cells, results in a series of signals causing irregular cell growth and inhibition of apoptosis. Therefore the ID8 mouse ovarian cancer cell line correlates with human ovarian cancer cell lines and provides a unique model to study ovarian cancer progression and pre-therapeutic trials in mice models with intact immune system (31).

To obtain the lysate, the ID8 cells were treated with hypotonic buffer and exposed to freeze-thaw cycles. The whole cell lysate obtained was a turbid extract, which was evaluated for protein content by Biorad DC protein assay. The total protein concentration of lysate was 1.56±0.5 mg/ml.

Preparation and Characterization of Vaccine Microparticles

One of the major challenges of oral vaccination is the avoidance of immune tolerance. However, this issue can be avoided by entrapping the vaccine antigen and transforming it into a particulate antigen (15, 16, 33). This can be due to the efficient and enhanced uptake of particulate antigen by M cells in the Peyer's patches by phagocytosis, when compared to minimal antigen uptake in solution form by pinocytosis. Moreover, protein antigens taken up as particles are more potent in activating antigen presenting cells (APCs) than soluble antigens. We formulated microparticles containing whole cell lysate using spray drying technique which can avoid use of organic solvents and damage to the proteins. The polymeric matrix was composed of enteric polymers such as HPMC-AS and Eudragit® FS30D to provide protection to the antigens after oral administration. Ano et al. have reported a formulation of an oral vaccine of inactivated Vibrio cholerae by spray drying using Eudragit® FS30D (46). This polymer was found to be a good candidate for controlled release of antigens required for oral delivery and resulted in vibriocidal antibody titers. We added chitosan glycol to the matrix to impart a positive charge to the microparticles (33). In addition, the formulation contained a M-cell targeting ligand, AAL, for better uptake of microparticles by the intestinal M-cells, and immuno-stimulatory molecules such as IL-2 and IL-12, which can activate APCs such as dendritic cells (42). Orally delivered vaccines, especially particulate antigens are sampled by M-cells in the Peyer's patches of the intestine. Further these antigens are processed by professional antigen presenting cells (APCs) such as dendritic cells and macrophages that reside in the Peyer's patches (25, 26). Moreover, higher anti-tumor effects were reported when IL-2 was delivered as an adjuvant in a slow-releasing depot form rather than a free form (42). Incorporation of IL-2 in particle addresses this issue seen with free IL-2.

The morphology of particles showed crumbled, collapsed and irregular shaped microparticles as shown in FIG. 3. Eudragit® FS30D microparticles have shown to result in such a shape upon spray drying (46). The production yield, particle size and charge along with particle size distribution are given in Table 1, which indicates there was no significant change in size and charge upon loading these particles with lysate.

Figure 9:
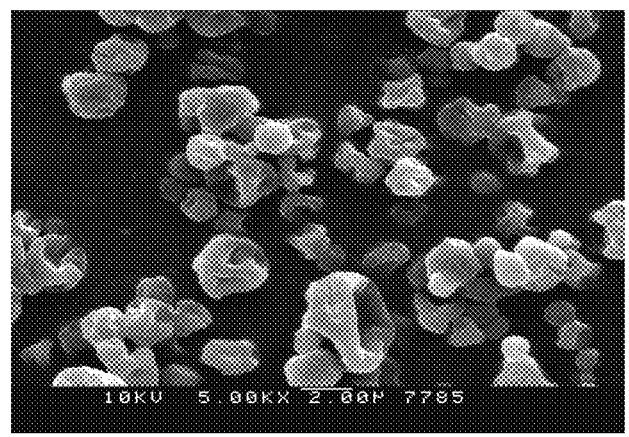
FIG. 9 illustrates a scanning electronic microscopy photograph of microparticles obtained by spray drying technology, showing crumbled, collapsed and irregular shaped microparticles.

FIG. 9 shows a scanning electronic microscopy photograph of microparticles obtained by spray drying technology, showing crumbled, collapsed and irregular shaped microparticles The size, charge and hydrophobicity of microparticles are important parameters controlling particle uptake via M-cells in Peyer's patches of small intestine upon oral administration. Microparticles of diameter less than 5 µm can get an access through M-cells, and therefore can trigger immune response against the antigens.

TABLE 1

In-vitro characterization of microparticles

| Formulation | Production yield % w/w | Mean particle size (µm) | Particle size distribution (µm) | | | Zeta potential mV |
|---|---|---|---|---|---|---|
| | | | D10 | D50 | D90 | |
| Placebo/Blank | 72.58 ± 3.41 | 1.61 ± 0.54 | 0.18 ± 0.03 | 0.88 ± 0.16 | 1.65 ± 0.46 | 11.75 ± 3.74 |
| Vaccine Microparticles | 74.68 ± 4.91 | 1.58 ± 0.62 | 0.22 ± 0.12 | 0.81 ± 0.03 | 1.58 ± 0.29 | 12.48 ± 2.32 |
| Vaccine Microparticles with interleukins | 69.98 ± 2.88 | 1.52 ± 0.63 | 0.19 ± 0.08 | 0.78 ± 0.15 | 1.60 ± 0.51 | 12.52 ± 2.11 |

Moreover, the polymers used such as HPMC-AS and Eudragit® FS30D are hydrophobic in nature. Thus, the microparticles formulated with these polymers and with size and charge suitable for M-cell uptake are likely to favor antigen targeting to immune cells in gut-associated lymphoid tissues (GALT) via M-cells after oral administration. In order to determine loading efficiency of these particles, we utilized pH dependent solubility property of polymers, which allows the particles to dissolve in alkaline pH above 7.0. The extracted proteins were quantified using Biorad DC protein assay. The loading efficiency of the particles was found to be 92.68±4.77% w/w.

Immunization with Vaccine Microparticles Suppresses Tumor Growth

Figure 10A:
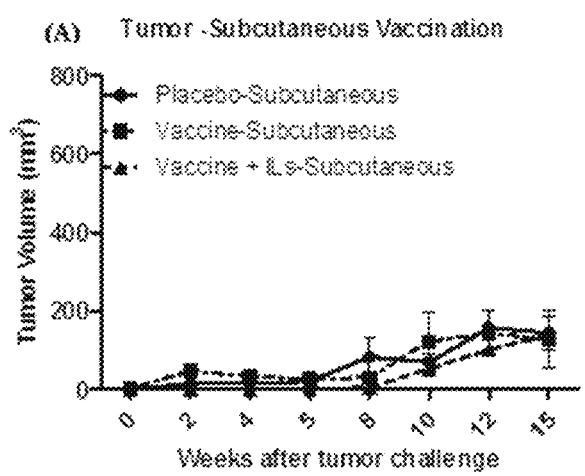
FIG. 10A illustrates a tumor growth monitored upon subcutaneous immunization with vaccine microparticles.
Figure 10B:
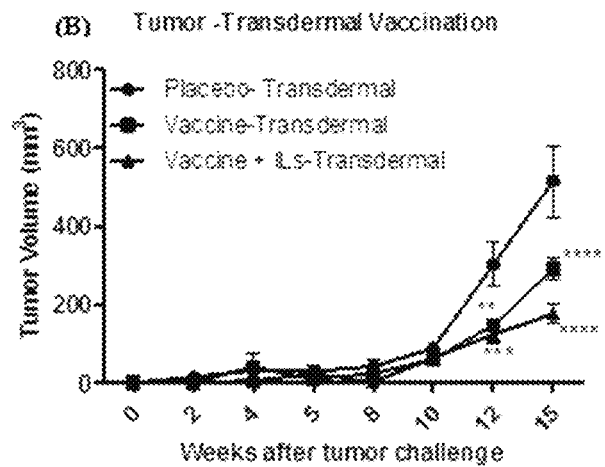
FIG. 10B illustrates a tumor growth monitored upon transdermal immunization with vaccine microparticles.
Figure 10C:
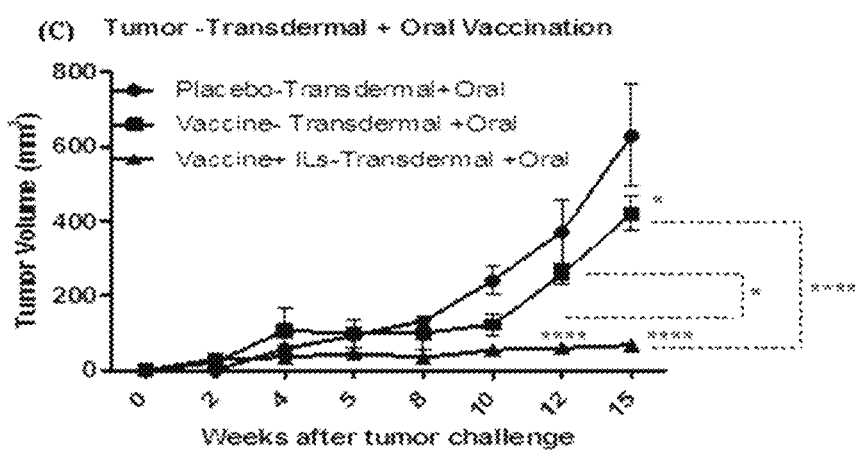
FIG. 10C illustrates a tumor growth monitored upon transdermal+ oral immunization with vaccine microparticles.

Transdermal, Subcutaneous and Transdermal +Oral Vaccination:

The tumor volume measurements obtained are shown in FIG. 10. In case of mice treated with placebo particles, the tumor developed rapidly. However, vaccinated mice showed tumor suppression when compared to non-vaccinated/placebo group. Vaccine alone resulted in around 1.5 times tumor suppression in case of transdermal and combination of routes at the end of $15^{th}$ week. In case of interleukins, transdermal route showed around 3 times of tumor suppression and combination of routes resulted in around 9 times of tumor suppression, when compared to non-vaccinated mice. The subcutaneous vaccination with and without interleukins showed initial retardation in tumor volume till the end of $8^{th}$ week; however the tumor volume increased to the level obtained in non-vaccinated mice at the end of $15^{th}$ week. Transdermally vaccinated mice showed significant retardation of tumor volume in comparison to non-vaccinated animals at 12th week after the tumor challenge ($p<0.05$), while mice vaccinated with combination of two routes showed significant retardation at $15^{th}$ week after tumor challenge. In subcutaneous vaccination study, there was no significant difference in tumor volumes of vaccinated and non-vaccinated mice at the end of $15^{th}$ week. The tumor volumes were found to be low for all three formulations when compared to other routes of vaccination. This might be due to subcutaneous administration of particles which made the immune system alert even against the components of particles. This might have resulted in low tumor volumes in case of mice treated with placebo particles.

FIG. 10 shows tumor growth monitored upon subcutaneous, transdermal and transdermal+oral immunization with vaccine microparticles: Mean tumor volumes for mice groups treated with vaccine microparticles with and without interleukins along with data with mice treated with placebo microparticles. The tumor volume was monitored with the aid of vernier calipers on a weekly basis. Subcutaneous vaccination did not show any tumor suppression. Vaccinated mice showed higher tumor suppression as compared to non-vaccinated/placebo treated mice in case of transdermal and transdermal+oral immunization. Interleukins showed even further tumor suppression in case of transdermal+oral immunization.

*$p<0.05$, $p<0.01$, *$p<0.001$, ****$p<0.0001$

In case of transdermal route, there was no significant difference between vaccine and vaccine with interleukin groups in terms of tumor volumes. This can be due to the interleukin concentration used in vaccine which was not high enough to retard tumor growth more than that seen with vaccine alone. Higher concentration of interleukins might be needed to show additional tumor suppression. However, in case of combination routes, a significant difference was seen in tumor volumes of vaccine with and without interleukins at $12^{th}$ week ($p<0.05$) and $15^{th}$ week ($p<0.0001$). The interleukins were found to contribute to even more tumor suppression when administered via oral as well as transdermal route.

Example 3

Vaccines for Infectious Diseases
Influenza Vaccines

Influenza viruses are responsible for causing highly infectious respiratory diseases in humans (1). Some common symptoms of influenza infection include sore throat, cough, fever, runny or stuffy nose, and muscle or body aches. Flu viruses can lead to severe illness resulting in hospitalization or in extreme cases, death. Seasonal influenza vaccines are recommended by the Center for Disease Control and Prevention (CDC) to protect against the flu which is known to be highly contagious and is easily transmitted (1). Commercial influenza vaccines consist of multiple influenza strains, which are alternated each year depending on various regions of the world and mutations in the flu virus (2). The extracellular domain of the M2 (M2e) consists of a small ion channel membrane protein common to all human influenza A virus strains; thus, it has been of great interest to researchers for its use as a potential antigen due to its ability to protect against all influenza type A viruses (3). However, the M2e is a small and non-antigenic protein, which is unable to stimulate the immune system in humans. Multiple M2e proteins are incorporated into a M2e5x protein (made of five M2e peptides) also known as M2e virus-like particles (VLPs) which are more immunogenic (4). Currently, influenza vaccines, such as, but not limited to, Fluzone (Sanofi Pasteur), Fluarix (GlaxoSmithKline), and Fluvirin (Novartis Vaccines and Diagnostics) are administered via the intramuscular route (1). Disadvantages of these injectable vaccines are antigen instability, cold-chain storage, and cost for vaccine administration (5). Developing a particulate influenza vaccine for non-parenteral deliveries will overcome these limitations and lead to increased amounts of vaccinations resulting from the ease of these routes of administration. (6).

Adjuvants have been studied and employed in vaccines for decades in order to improve, expedite, and prolong specific immune responses produced by vaccine antigens, such responses include, but are not limited to, increase in antibody responses, induction of cell mediated immunity, and reduction in dose of antigen and the number of doses required for vaccination (7). For a successful immune response to a vaccine, there are four classes of signals: (a) antigen, (b) co-stimulation of immune cells including antigen-presenting cells (APCs), (c) immune system modulation, and (d) activation of innate immune response (8)(9). Various adjuvants utilize their distinct effects via different mechanisms to stimulate the immune system, and hence it is essential to appoint appropriate adjuvants for a specific given antigen. Adjuvants can be classified into two types: delivery system and immune potentiator (10). Some adjuvants function as antigen delivery systems such as alum, calcium phosphate tyrosine liposomes, virosomes, emulsions micro/nano particles (MF59, ISCOMS), and virus-like particles, because these particulate adjuvants increase antigen stability and allow them to be presented for an extended period of time (prolonging the signal of the antigen) (11). Delivery system based adjuvants are often taken up by phagocytosis into antigen presenting cells (APCs), and they can also induce an immune response signaling and indirectly activating APCs. Immune potentiators are purified components of bacterial cells or viruses; thus, they are recognized as "danger signals" by receptors present on immune cells (APCs) (9). Immune potentiators directly stimulate all the necessary signals for an immune response to an antigen. A major category of immune potentiators is toll-like receptor (TLR) agonists, which activate signaling pathways to trigger innate immune responses. Some examples of adjuvants that act as TLR agonists include MPL and synthetic derivatives, muramyl dipeptide and derivatives, CpG oligonucleotides, alternative bacterial or viral components (flagellin), saponins, dsRNA, and resiquimod (12). Since delivery system based adjuvants elevate the amount of antigen that reach APCs and immune potentiators mainly activate these APCs; combinations of adjuvants from both classes can be used to maximize potency of a vaccine.

In this study, we formulated a microparticulate influenza vaccine using M2e5x protein (M2p) as a universal antigen for all influenza type A viruses. We also screened eight various adjuvants (alum, MF59, R848, flagellin, monophospholyl lipid A (MPL), cholera toxin (CT), P4 and CpG) for suitability with the M2p vaccine. The effects of these adjuvants were evaluated using an ex-vivo method to (i) compare expression levels of cluster differentiations (CDs) 80, 86, 40 and major histocompatibility complex class II (MHC II); and (ii) differentiate CD4+, CD8+ T lymphocyte populations.

Materials and Methods

Materials

Aqueous Dispersion (Aquacoat® CPD) and hydroxyl propyl methylcellulose acetate succinate (HPMCAS, AQOAT) and ethyl cellulose 30% (w/v) aqueous dispersion (AQOAT) were samples from FMC biopolymers, Philadelphia, Pa. Trehalose was purchased from Sigma Aldrich, St. Louis, Mo. Sodium thioglycolate and glycol chitosan were purchased from Sigma-Aldrich. A bicinchoninic Acid (BCA) protein assay kit was purchased from Thermo Scientific. Swiss Webster mice were obtained from Charles River. Anti-mouse CD86-FITC, CD80-PE, CD40-PE, MHC Class II (I-A) FITC markers were purchased from Affymetrix eBioscience.

MPL, R848, flagellin (from *Salmonella* typhimurium) and cholera toxin from Vibrio cholera were purchased from Sigma-Aldrich. AddaVax™ (similar to MF59), CpG oligodeoxynucleotides and Alhydrogel® 2% (aluminum hydroxide gel) were obtained from Infigen.

Methods i) Preparation of Microparticulate Vaccine

The M2p was incorporated into an enteric-coated polymer matrix in this formulation. This matrix consisted of 20% (w/w) CPD, 35% (w/w) ethyl cellulose (EC), 35% (w/w) HPMCAS, 4% (w/w) trehalose, 4% (w/w) chitosan and 2% (w/w) M2p. First, CPD dispersion (30% w/v) was diluted in deionized water with a concentration of five mg/ml under stirring. CPD and HPMCAS were dissolved separately using 1N NaOH to make final solutions at pH of 6.0 and 8.0, respectively. The mixture of CPD, HPMCAS, and EC was obtained as mentioned above, and the final solution pH was adjusted to be 7.0. Glycol chitosan was then added along with M2p and trehalose. In addition, 0.01% (v/v) of Tween-20 was added to enhance the smooth surface of the microparticles (MPs). The solution was stirred at 50 rpm during the spraying process using a Buchi B290 spray dryer to maintain its homogeneity. Microparticulate adjuvants were formulated using the same procedure as the vaccine microparticles.

ii) Characterization of Vaccine Microparticles

The percentage product yield was governed by the following formula:

$$\text{The Percentage yield}(\%) = \frac{M_{after\ the\ spray-drying\ process}}{M_{theoretical}} \times 100\%$$

where $M_{after\ spray\ drying\ process}$ is the total mass of the formulation after the spray-drying process, $M_{theoretical}$ is the total mass of the formulation before the spray-drying process. The MPs were characterized for size using Spectrex PC-2000 laser particle counter. In brief, the MPs were suspended in 100 mM citric acid buffer at pH 4.0 with a concentration of 1.0 mg/ml. Using the suspension, 3.0 mL were transferred to a disposable cuvette and read by the counter. The size distribution and the surface morphology were obtained using Phenom Pure Desktop® scanning electron microscopy (SEM). The MPs were positioned onto a metal holder, and the image was taken with ×20,000, a view angle of 28.7, and an accelerating voltage of 20 kV.

To investigate the potential of an oral delivery system for the M2p vaccine, a release of M2p from the vaccine MPs was performed based on mimicking the mouse gastric tract condition. Ten milligrams of the MPs were suspended in one ml of simulated gastric fluid (pH 3.0) for 30 minutes, followed by the one ml of simulated intestinal fluid (pH 5.0) for five hours. During the incubation time, samples were kept in 37° C. at 50 rpm. Sampling time points were 0.5, 1.5, 2.5, 3.5, 4.5 and 5.5 hours and the samples were analyzed for M2p content using the BCA protein assay kit.

iii) Antigen-Presenting Cells Collection

5 Sodium thioglycolate was injected into the intraperitoneal cavity of Swiss Webster (6-8 week old) with the amount of 40 mg per mouse to recruit the APCs (13)(14). After four days, these mice were euthanized and 5.0 mL of PBS was injected intraperitoneally into each mouse to harvest cells from the cavity. Collected cells were washed with PBS twice before adding the complete RPMI media. After these APCs adhered to the bottom of a T75 flask, the supernatant was removed and complete RPMI media was added in the presence of ConA (50 µl/ml).

iv) Nitric Oxide Assay

The harvested APCs ($5 \times 10^4$ cells/well) were seeded in Dulbecco's complete media in a 96 well plate. The soluble and particulate vaccines (with and without adjuvants) were introduced to the APCs with the same amount of antigen (2.5 µg) and adjuvant (2.5 µg). The induced APCs were incubated for 20 hours at 37° C. % $CO_2$. Supernatants were collected and the amount of nitric oxide released in each group was analyzed using the Greiss chemical method (equal volumes of 1% sulphanilamide and 0.1% N-(1-naphthylethylenediamine)). The plate was read at a wavelength of 540 nm (15).

vi) CD4/CD8 Population Analysis

The spleens were collected from the same mice that were harvested APCs from the intraperitoneal cavity, and the single-cell suspensions of the spleens were introduced into the stimulated APCs with a ratio of 1:1 (splenocytes:APCs). After a five-day incubation at 37° C. and 5% $CO_2$, the splenocytes were harvested from the supernatant, washed with Hank's balanced salt solution and labeled with anti-mouse CD4 PE and anti-mouse CD8a FITC. The cells were analyzed for $CD4^+$ and $CD8^+$ T cell populations using BD Accuri® C6 flow cytometer.

vii) Analytical Tests:

Statistical analyses were performed using the GraphPad Prism software. For more than two groups, one-way ANOVA was applied and p value was used as $p > 0.05$ (non-significant differences), $p < 0.05$ (*), $p < 0.01$ (), and $p < 0.001$ (*). Error bars represent standard error of the mean.

Results

Preparation and Characterization of Vaccine Microparticles

Figure 11:
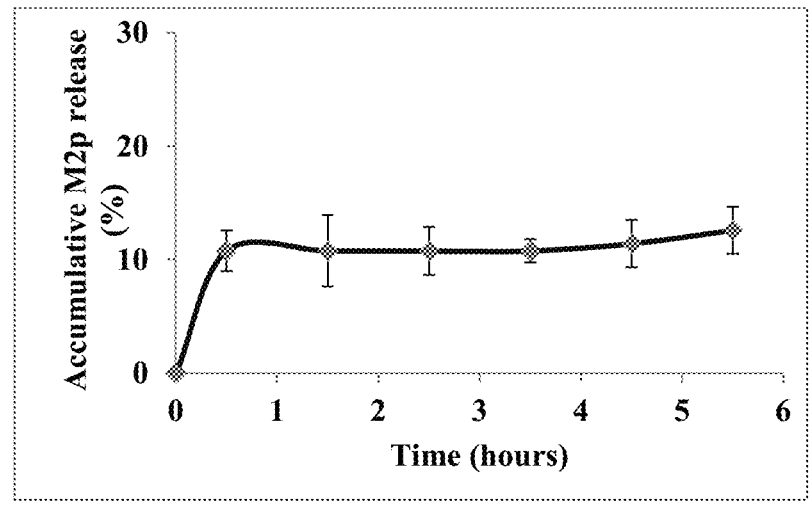
FIG. 11 illustrates a release profile of M2p protein. 10 mg of microparticles was suspended in 1 ml of simulated gastric fluid (pH 3.0) for 30 minutes, followed by 1 ml of the simulated intestinal fluid (pH 5.0) for 5 hours. 10.8% M2p released in the gastric condition for 30 minutes and 2.6% M2p released in the intestinal condition in 5 hours.

The average percent yield of the MPs was 90%±5.3% (w/w) after the spray drying process. The size of MPs ranged from 1.0 µm to 5.5 µm with an average size of 3.76±0.84 µm. The morphological characterization illustrated donut shaped MPs as shown in FIG. 11. All microparticulate vaccines and adjuvants had similar morphologies. The release study was conducted to measure the cumulative percentage of M2p released is graphically shown in FIG. 2. The graph confirmed that 10.8% of M2p released in the gastric condition for 30 minutes and 2.6% of M2p released in the intestinal condition in five hours.

Antigen Recognition

Figure 12:
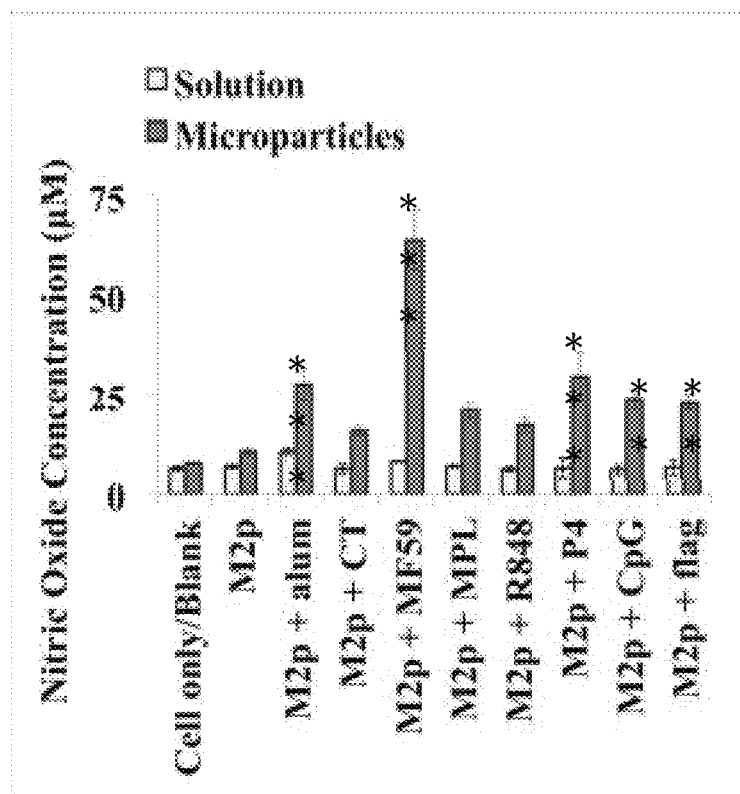
FIG. 12 illustrates a nitric oxide release from APCs following incubation with respective formulations for 20 hours. All adjuvant treated groups included 2.5 µg of adjuvant in microparticles (MP) and 2.5 µg of M2p in MP. There was no significant difference in nitric oxide levels between soluble and microparticulate M2p vaccines. Alum, MF59, P4, CpG and flagellin adjuvant treated groups showed significant increase in nitric oxide levels compared to M2p MP alone. (* $p<0.001$,  $p<0.01$, * $p<0.05$).

The nitric oxide assay was performed to investigate the recognition of vaccine and adjuvants by the APCs (16). Nitric oxide (NO) is released in the process of conversion of arginine to citrulline by nitric oxide synthase during the recognition and phagocytosis of antigen from APCs (17). A higher level of NO released indicates a stronger activation of APCs by the vaccines. In FIG. 12, the nitric oxide level of M2p MP was not significantly higher compared to the blank MP and M2p solution groups. However, the nitric oxide concentrations were highly elevated ($p < 0.001$) in alum, MF59 and P4 treated groups compared to the M2p MP group. Nitric oxide levels were also significantly higher ($p < 0.05$) in CpG and Flagellin treated groups.

All the soluble antigen and adjuvant treated groups served as controls and these groups showed minimal levels of nitric oxide, compared to the microparticulate vaccine and adjuvant treated groups.

Activation of CD4 and CD8 T Cells

T cells are divided into two main classes based on their effector functions and differentiated by the expression of cell-surface proteins: CD4+ and CD8+ (20). The T cell populations were investigated and they are graphically illustrated in FIGS. 14 and 13. CD4+ and CD8+ T cell populations were statistically higher (p<0.05) in Alum and MF59 treated groups, compared to the vaccine MP treated group. In addition, CD8+ T cell population was significantly higher in MPL treated group, compared to CD4+ T cell population as elicited in the flagellin treated group. In addition, the microparticulate vaccine increased both CD4+ and CD8+ T cell populations (p<0.001).

FIG. 11 Shows a release profile of M2p protein. 10 mg of microparticles was suspended in 1 ml of simulated gastric fluid (pH 3.0) for 30 minutes, followed by 1 ml of the simulated intestinal fluid (pH 5.0) for 5 hours. 10.8% M2p released in the gastric condition for 30 minutes and 2.6% M2p released in the intestinal condition in 5 hours.

FIG. 12 Shows nitric oxide release from APCs following incubation with respective formulations for 20 hours. All adjuvant treated groups included 2.5 m of adjuvant in microparticles (MP) and 2.5 µg of M2p in MP. There was no significant difference in nitric oxide levels between soluble and microparticulate M2p vaccines. Alum, MF59, P4, CpG and flagellin adjuvant treated groups showed significant increase in nitric oxide levels compared to M2p MP alone. (* p<0.001,  p<0.01, * p<0.05)

Figure 13:
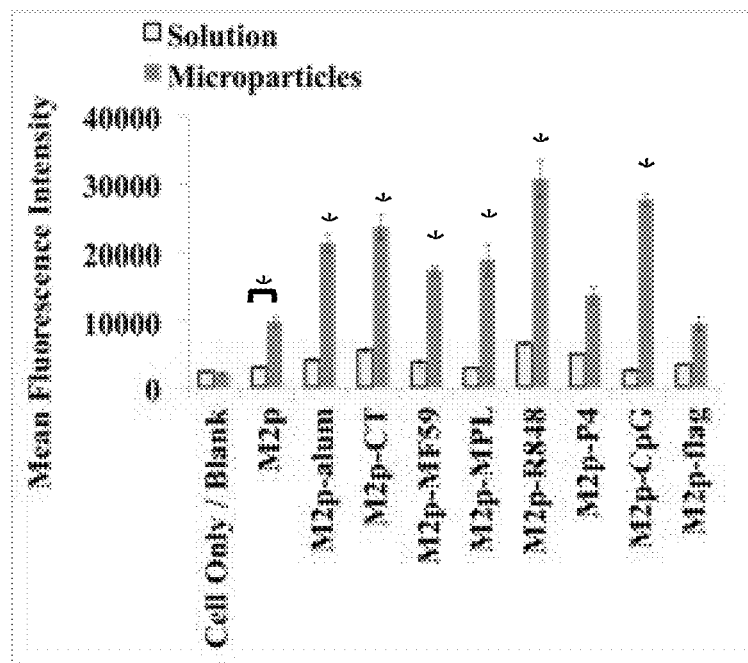
FIG. 13 illustrates an expression of MHC II on APCs following incubation of microparticle formulations for 20 hours. All adjuvant treated groups contained 2.5 µg of M2p and 2.5 µg of adjuvant in microparticles. M2p MP group showed statistically higher CD40 expression compared to M2p solution group ($p<0.0001$). Except for P4 and Flag, MHC II expression was elevated in all adjuvant treated group ($p<0.0001$) compared to M2p MP. Elevated MHC II expression will elicit a T-helper cell mediated response leading to antibody production against the antigen.

FIG. 13 Shows an expression of MHC II on APCs following incubation of microparticle formulations for 20 hours. All adjuvant treated groups contained 2.5 µg of M2p and 2.5 µg of adjuvant in microparticles. M2p MP group showed statistically higher CD40 expression compared to M2p solution group (p<0.0001). Except for P4 and Flag, MHC II expression was elevated in all adjuvant treated group (p<0.0001) compared to M2p MP. Elevated MHC II expression will elicit a T-helper cell mediated response leading to antibody production against the antigen.

Figure 14:
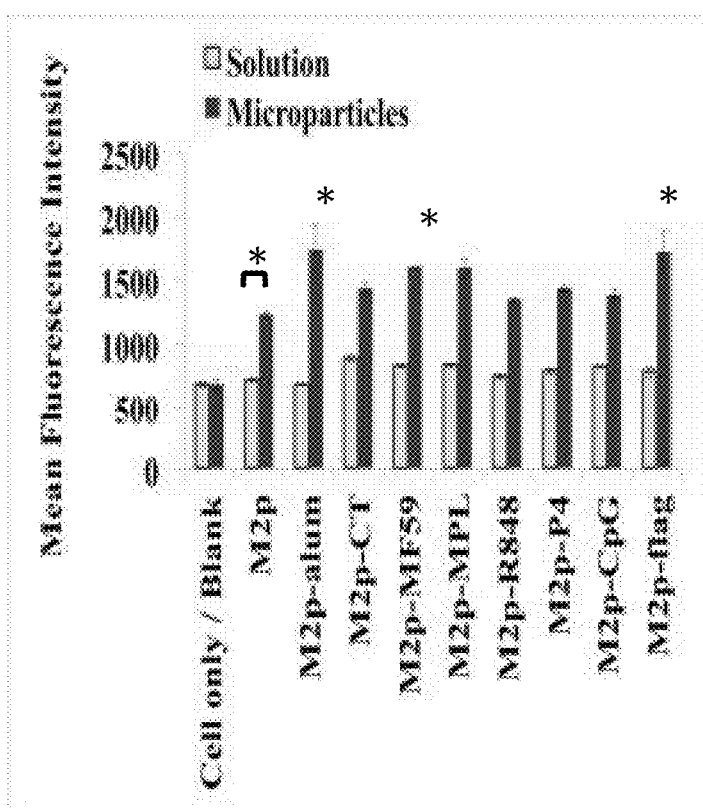
FIG. 14 illustrates a CD4+ T cell population following incubation of splenocytes with APCs for 5 days. M2p MP group showed statistically higher CD4+ T cell population compared to M2p solution group. Alum, MF59 and Flag elevated CD4+ T cell population (* $p<0.001$,  $p<0.01$, * $p<0.05$) compared to M2p MP treated group.

FIG. 14 shows CD4+ T cell population following incubation of splenocytes with APCs for 5 days. M2p MP group showed statistically higher CD4+ T cell population compared to M2p solution group. Alum, MF59 and Flag elevated CD4+ T cell population (* p<0.001,  p<0.01, * p<0.05) compared to M2p MP treated group.

Figure 15:
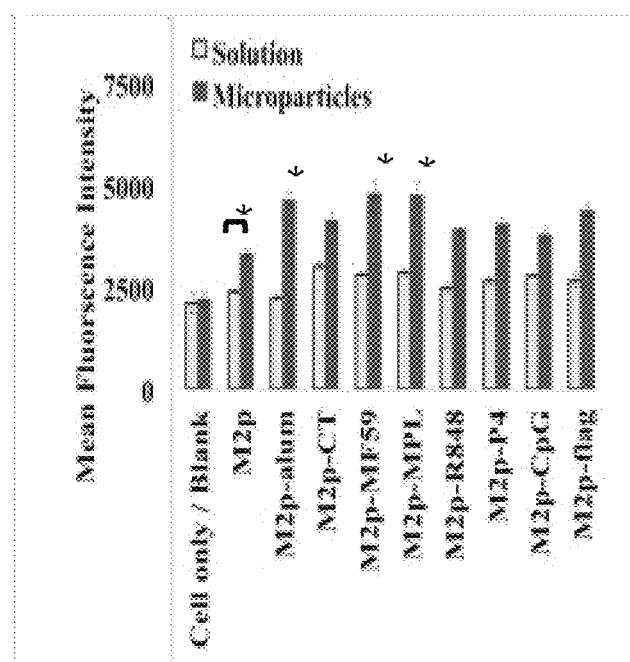
FIG. 15 illustrates a CD8+ T cell population following incubation of splenocytes with APCs for 5 days. M2p MP group showed statistically higher CD8+ T cell population compared to M2p solution group. CD8+ T cell population was elevated in alum, MF59 and MPL treated groups (* $p<0.001$,  $p<0.01$ and * $p<0.05$) compared to M2p MP treated group.

FIG. 15 Shows a CD8+ T cell population following incubation of splenocytes with APCs for 5 days. M2p MP group showed statistically higher CD8+ T cell population compared to M2p solution group. CD8+ T cell population was elevated in alum, MF59 and MPL treated groups (* p<0.001,  p<0.01 and * p<0.05) compared to M2p MP treated group.

REFERENCES FOR EXAMPLE 3

1. Centers for Disease Control and Prevention. Seasonal Influenza (Flu) [Internet]. 2014. Available from: cdc.gov/flu/about/disease/index.
2. Pregliasco F, Mensi C, Serpilli W, Speccher L, Masella P, Belloni A. Immunogenicity and safety of three commercial influenza vaccines in institutionalized elderly. Aging Milan Italy. 2001 February; 13(1):38-43.
3. Quan F S, Huang C, Compans R W, Kang S M. Virus-like particle vaccine induces protective immunity against homologous and heterologous strains of influenza virus. J Virol. 2007 April; 81(7):3514-24.
4. Kim M C, Song J M, O E, Kwon Y M, Lee Y J, Compans R W, et al. Virus-like particles containing multiple M2 extracellular domains confer improved cross-protection against various subtypes of influenza virus. Mol Ther J Am Soc Gene Ther. 2013 February; 21(2):485-92.
5. Andrew T. Kroger, Ciro V. Sumaya, Larry K. Pickering, William L. Atkinson. General Recommendations on Immunization: Recommendations of the Advisory Committee on Immunization Practices (ACIP) [Internet]. Morbidity and Mortality Weekly Report (MMWR). Available from: cdc.gov/mmwr/preview/mmwrhtmL/rr6002a1.
6. Bakhru S H, Furtado S, Morello A P, Mathiowitz E. Oral delivery of proteins by biodegradable nanoparticles. Adv Drug Deliv Rev. 2013 Jun. 15; 65(6):811-21.
7. Smith D M, Simon J K, Baker J R. Applications of nanotechnology for immunology. Nat Rev Immunol. 2013 August; 13(8):592-605.
8. Maisonneuve C, Bertholet S, Philpott D J, De Gregorio E. Unleashing the potential of NOD- and Toll-like agonists as vaccine adjuvants. Proc Natl Acad Sci USA. 2014 Aug. 26; 111(34):12294-9.
9. Derek T O'Hagan. New Generation Vaccine Adjuvants [Internet]. Novartis Vaccines and Diagnostics; Available from: roitt.com/elspdf/Newgen_Vaccines.
10. Mohan T, Verma P, Rao D N. Novel adjuvants & delivery vehicles for vaccines development: a road ahead. Indian J Med Res. 2013 November; 138(5):779-95.
11. Gupta R K, Siber G R. Adjuvants for human vaccines—current status, problems and future prospects. Vaccine. 1995 October; 13(14):1263-76.
12. Batista-Duharte A, Lindblad E B, Oviedo-Orta E. Progress in understanding adjuvant immunotoxicity mechanisms. Toxicol Lett. 2011 Jun. 10; 203(2):97-105.
13. Cohn Z A. Activation of mononuclear phagocytes: fact, fancy, and future. J Immunol Baltim Md. 1950. 1978 September; 121(3):813-6.
14. Lagasse E, Weissman I L. Flow cytometric identification of murine neutrophils and monocytes. J Immunol Methods. 1996 Oct. 16; 197(1-2):139-50.
15. Zughaier S M, Tzeng Y L, Zimmer S M, Datta A, Carlson R W, Stephens D S. Neisseria meningitidis lipooligosaccharide structure-dependent activation of the macrophage CD14/Toll-like receptor 4 pathway. Infect Immun. 2004 January; 72(1):371-80.
16. Roper R L. Antigen presentation assays to investigate uncharacterized immunoregulatory genes. Methods Mol Biol Clifton N.J. 2012; 890:259-71.
17. Kohchi C, Inagawa H, Nishizawa T, Soma G I. ROS and innate immunity. Anticancer Res. 2009 March; 29(3):817-21.
18. Janeway C. Immunobiology the immune system health & disease. New York: Garland; 2001.
19. Pinchuk L M, Polacino P S, Agy M B, Klaus S J, Clark E A. The role of CD40 and CD80 accessory cell molecules in dendritic cell-dependent HIV-1 infection. Immunity. 1994 July; 1(4):317-25.
20. Chandele A, Mukerjee P, Das G, Ahmed R, Chauhan V S. Phenotypic and functional profiling of malaria-induced CD8 and CD4 T cells during blood-stage infection with Plasmodium yoelii. Immunology. 2011 February; 132(2):273-86.
21. Anton N, Jakhmola A, Vandamme T F. Trojan microparticles for drug delivery. Pharmaceutics. 2012; 4(1):1-25.
22. Ferreira S A, Gama F M, Vilanova M. Polymeric nanogels as vaccine delivery systems. Nanomedicine Nanotechnol Biol Med. 2013 February; 9(2):159-73.
23. Steinman R M, Hemmi H. Dendritic cells: translating innate to adaptive immunity. Curr Top Microbiol Immunol. 2006; 311:17-58.

24. Holling T M, Schooten E, van Den Elsen P J. Function and regulation of MHC class II molecules in T-lymphocytes: of mice and men. Hum Immunol. 2004 April; 65(4):282-90.

25. McBride J M, Fathman C G. A complicated relationship: fulfilling the interactive needs of the T lymphocyte and the dendritic cell. Pharmacogenomics J. 2002; 2(6):367-76.

26. Schmid D, Pypaert M, Münz C. Antigen-loading compartments for major histocompatibility complex class II molecules continuously receive input from autophagosomes. Immunity. 2007 January; 26(1):79-92.

27. Cresswell P, Ackerman A L, Giodini A, Peaper D R, Wearsch P A. Mechanisms of MHC class I-restricted antigen processing and cross-presentation. Immunol Rev. 2005 October; 207:145-57.

28. American Chemical Society. Interactions of nanomaterials with emerging environmental contaminants. Doong R, Sharma V K, Kim H, editors. Washington D.C.: American Chemical Society; 2013.

29. Fox C B, Kramer R M, Barnes V L, Dowling Q M, Vedvick T S. Working together: interactions between vaccine antigens and adjuvants. Ther Adv Vaccines. 2013 May; 1(1):7-20.

30. Seubert A, Monaci E, Pizza M, O'Hagan D T, Wack A. The adjuvants aluminum hydroxide and MF59 induce monocyte and granulocyte chemoattractants and enhance monocyte differentiation toward dendritic cells. J Immunol Baltim Md. 1950. 2008 Apr. 15; 180(8):5402-12.

31. Seubert A, Calabro S, Santini L, Galli B, Genovese A, Valentini S, et al. Adjuvanticity of the oil-in-water emulsion MF59 is independent of Nlrp3 inflammasome but requires the adaptor protein MyD88. Proc Natl Acad Sci USA. 2011 Jul. 5; 108(27):11169-74.

32. Tetsutani K, Ishii K J. Adjuvants in influenza vaccines. Vaccine. 2012 Dec. 14; 30(52):7658-61.

33. Kool M, Soullié T, van Nimwegen M, Willart M A M, Muskens F, Jung S, et al. Alum adjuvant boosts adaptive immunity by inducing uric acid and activating inflammatory dendritic cells. J Exp Med. 2008 Apr. 14; 205(4):869-82.

34. Rajam G, Skinner J, Melnick N, Martinez J, Carlone G M, Sampson J S, et al. A 28-aa pneumococcal surface adhesin A-derived peptide, P4, augments passive immunotherapy and rescues mice from fatal pneumococcal infection. J Infect Dis. 2009 Apr. 15; 199(8):1233-8.

35. Rajam G, Phillips D J, White E, Anderton J, Hooper C W, Sampson J S, et al. A functional epitope of the pneumococcal surface adhesin A activates nasopharyngeal cells and increases bacterial internalization. Microb Pathog. 2008 March; 44(3):186-96.

36. Gowrisankar Rajam, Mathieu Bangert, Gabrielle M. Hammons, Nikkol Melnick, George M. Carlone, Jacquelyn S. Sampson, et al. P4 Peptide Therapy Rescues Aged Mice from Fatal Pneumococcal Sepsis. Clin Vaccine Immunol CVI. 2010 November; 17(11):1823-4.

37. Datta S K, Sabet M, Nguyen K P L, Valdez P A, Gonzalez-Navajas J M, Islam S, et al. Mucosal adjuvant activity of cholera toxin requires Th17 cells and protects against inhalation anthrax. Proc Natl Acad Sci USA. 2010 Jun. 8; 107(23):10638-43.

38. Lycke N, Holmgren J. Strong adjuvant properties of cholera toxin on gut mucosal immune responses to orally presented antigens. Immunology. 1986 October; 59(2):301-8.

39. Langridge W, Dénes B, Fodor I. Cholera toxin B subunit modulation of mucosal vaccines for infectious and autoimmune diseases. Curr Opin Investig Drugs Lond Engl 2000.2010 August; 11(8):919-28.

40. O'Neill L A J, Bryant C E, Doyle S L. Therapeutic targeting of Toll-like receptors for infectious and inflammatory diseases and cancer. Pharmacol Rev. 2009 June; 61(2):177-97.

41. Mogensen T H. Pathogen recognition and inflammatory signaling in innate immune defenses. Clin Microbiol Rev. 2009 April; 22(2):240-73, Table of Contents.

42. Casella C R, Mitchell T C. Putting endotoxin to work for us: monophosphoryl lipid A as a safe and effective vaccine adjuvant. Cell Mol Life Sci CMLS. 2008 October; 65(20):3231-40.

43. Sheng K C, Day S, Wright M D, Stojanovska L, Apostolopoulos V. Enhanced Dendritic Cell-Mediated Antigen-Specific CD4+ T Cell Responses: IFN-Gamma Aids TLR Stimulation. J Drug Deliv. 2013; 2013:516749.

44. Vasilevko V, Ghochikyan A, Holterman M J, Agadjanyan M G. CD80 (B7-1) and CD86 (B7-2) are functionally equivalent in the initiation and maintenance of CD4+ T-cell proliferation after activation with suboptimal doses of PHA. DNA Cell Biol. 2002 March; 21(3):137-49.

45. Cuadros C, Lopez-Hernandez F J, Dominguez A L, McClelland M, Lustgarten J. Flagellin fusion proteins as adjuvants or vaccines induce specific immune responses. Infect Immun. 2004 May; 72(5):2810-6.

46. Letran S E, Lee S J, Atif S M, Uematsu S, Akira S, McSorley S J. TLR5 functions as an endocytic receptor to enhance flagellin-specific adaptive immunity. Eur J Immunol. 2011 January; 41(1):29-38.

47. Mifsud E J, Tan A C L, Jackson D C. TLR Agonists as Modulators of the Innate Immune Response and Their Potential as Agents Against Infectious Disease. Front Immunol. 2014; 5:79.

48. Kuznik A, Bencina M, Svajger U, Jeras M, Rozman B, Jerala R. Mechanism of endosomal TLR inhibition by antimalarial drugs and imidazoquinolines. J Immunol Baltim Md. 1950.2011 Apr. 15; 186(8):4794-804.

49. Coffman R L, Sher A, Seder R A. Vaccine adjuvants: putting innate immunity to work. Immunity. 2010 Oct. 29; 33(4):492-503.

50. Fournié J J, Sicard H, Poupot M, Bezombes C, Blanc A, Romagné F, et al. What lessons can be learned from γδ T cell-based cancer immunotherapy trials? Cell Mol Immunol. 2013 January; 10(1):35-41.

51. Brazolot Millan C L, Weeratna R, Krieg A M, Siegrist C A, Davis H L. CpG DNA can induce strong Th1 humoral and cell-mediated immune responses against hepatitis B surface antigen in young mice. Proc Natl Acad Sci USA. 1998 Dec. 22; 95(26):15553-8.

52. Weeratna R D, Brazolot Millan C L, McCluskie M J, Davis H L. CpG ODN can re-direct the Th bias of established Th2 immune responses in adult and young mice. FEMS Immunol Med Microbiol. 2001 December; 32(1):65-71.

53. Schubert C. Boosting our best shot. Nat Med. 2009 September; 15(9):984-8.

Example 4

Vaccine for Respiratory Synovial Virus (RSV)

The Respiratory Syncytial Virus (RSV) has become the leading cause of lower respiratory tract illnesses, commonly seen in 70,000-120,000 hospitalized infants a year. RSV manifests itself in the form of bronchiolitis and pneumonia and since there is no currently licensed vaccine for the virus, its effects can be severe especially in infants and older adults that have undeveloped or compromised immune systems. The current antiviral therapies available for RSV are not sufficient due to the lack of clinical data to support its long-term efficacy and safety.

There are two major antigenic proteins found on surface of the virus, a fusion F protein and a glycoprotein G. The fusion protein F is seen in both A and B strains of the virus and is incorporated into a virus like particle (VLP) which is highly immunogenic.

The F-VLP was incorporated into an enteric-coated polymer matrix using the Buchi B-290 spray dryer in a single step yielding a micro particulate vaccine. The Malvern zetasizer was used to characterize the micro particulate formulation.

For in vitro analysis of immunogenicity of the F-VLP, dendritic cells (DC 2.4) were cultured and exposed to varying concentrations of the vaccine. The optimal concentration was then used to screen four different adjuvants (Poly I:C, Alum, MPL and MF59). Evaluation of innate and adaptive immunity was done using the nitric oxide assay and expression of cell surface markers using the C6 flow cytometer.

The size of the micro particulate vaccine ranged between 3.0-5.0 microns. Following immunogenicity studies with dendritic cells, amount of nitric oxide released from vaccine with adjuvants Poly I:C, Alum and MF59 were much higher compared to vaccine alone. Cell surface marker expression (CD80/CD86, CD40, MHC I, MHC II) was found to be significantly higher in the adjuvant groups in comparison to vaccine alone and vaccine solution groups.

Assess immunogenicity of a micro particulate vaccine using fusion (F) protein VLP.

In Vitro

1. Evaluation of innate immunity
    a. Following exposure to an antigen, dendritic cells (DC 2.4) are known to release nitric oxide and express cell surface markers that signal CD4+ Helper T cells and/or CD8+ Cytotoxic T cells.
    b. Upon recognition of antigen (VLP), fragments of the antigen may be presented on MHC Class I and/or MHC Class II.
    c. MHC Class I stimulates co-stimulatory molecules CD80 or CD86, further activating CD8+ T cells
    d. MHC Class II stimulates co-stimulatory molecule CD40, further activating CD4+ T cells
    e. Adjuvants are known to enhance the immune response and were therefore used along with the micro particulate vaccine to observe if there was a boost in the immune response produced by the fusion (F) protein VLP.

Figure 16:
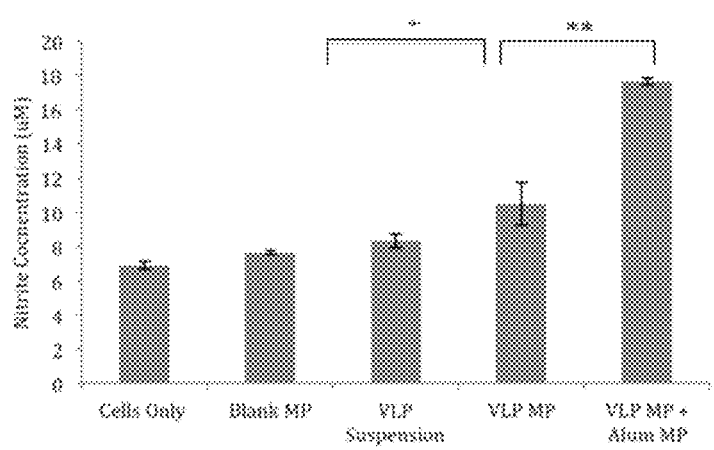
FIG. 16 illustrates an amount of Nitric Oxide released from DC 2.4 when exposed to blank MP, VLP Suspension, VLP MP and VLP MP+Alum MP. Nitric Oxide release in the VLP MP+Alum MP group was found to be significantly higher in comparison to all other groups (**$p<0.005$). In addition VLP MP showed higher levels of nitric oxide in comparison to VLP suspension (*$p<0.01$).

FIG. 16 shows the amount of Nitric Oxide released from DC 2.4 when exposed to blank MP, VLP Suspension, VLP MP and VLP MP+Alum MP. Nitric Oxide release in the VLP MP+Alum MP group was found to be significantly higher in comparison to all other groups (**$p<0.005$). In addition VLP MP showed higher levels of nitric oxide in comparison to VLP suspension (*$p<0.01$).

Figure 17:
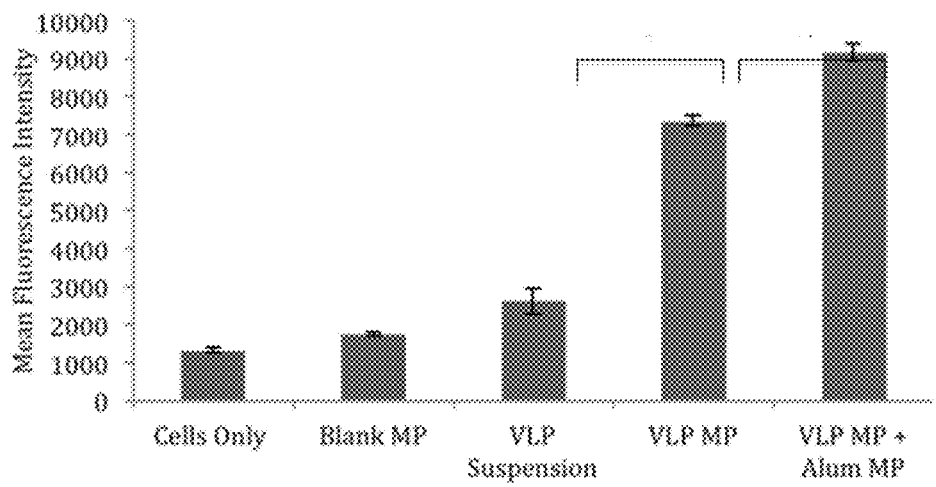
FIG. 17 illustrates a MHC Class I expression in DC 2.4 when exposed to blank MP, VLP Suspension, VLP MP and VLP MP+Alum MP. Higher expression of MHC Class I was found in the VLP MP+Alum MP group in comparison to all other groups (*p<0.005). In addition, VLP MP showed higher MHC Class I expression in comparison to VLP suspension (*p<0.005).

FIG. 17 shows MHC Class I expression in DC 2.4 when exposed to blank MP, VLP Suspension, VLP MP and VLP MP+Alum MP. Higher expression of MHC Class I was found in the VLP MP+Alum MP group in comparison to all other groups (*$p<0.005$). In addition VLP MP showed higher MHC Class I expression in comparison to VLP suspension (*$p<0.005$).

Figure 18:
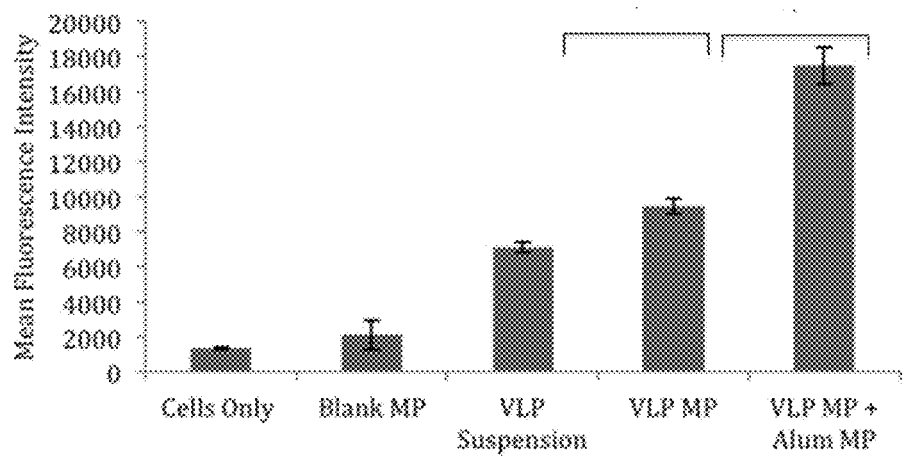
FIG. 18 illustrates a CD80 expression in DC 2.4 when exposed to blank MP, VLP Suspension, VLP MP and VLP MP+Alum MP. Higher expression of CD80 was found in the VLP MP+Alum MP group in comparison to all other groups (*p<0.001). In addition, VLP MP showed higher MHC Class I expression in comparison to VLP suspension (*p<0.001).

FIG. 18 shows CD80 expression in DC 2.4 when exposed to blank MP, VLP Suspension, VLP MP and VLP MP+Alum MP. Higher expression of CD80 was found in the VLP MP+Alum MP group in comparison to all other groups (*$p<0.001$). In addition VLP MP showed higher MHC Class I expression in comparison to VLP suspension (*$p<0.001$).

Figure 19:
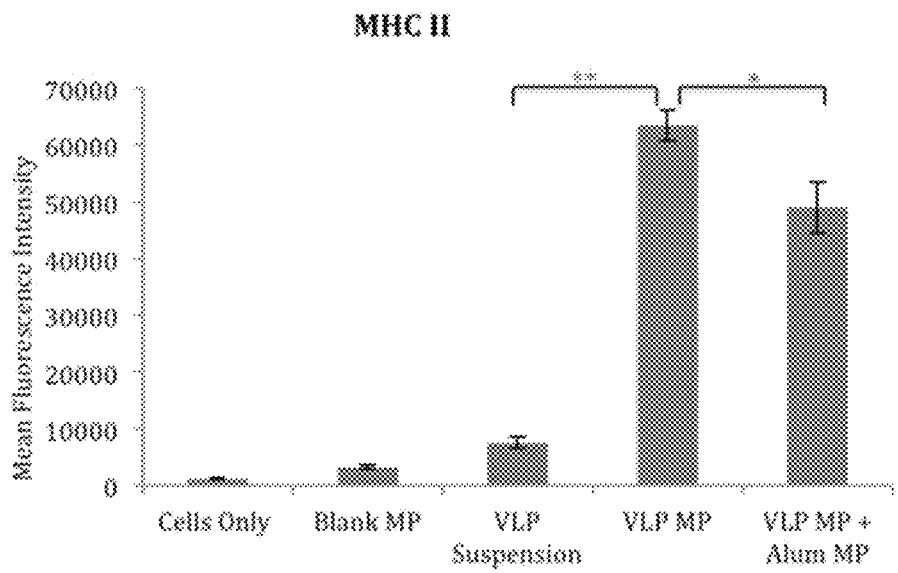
FIG. 19 illustrates a MHC Class II expression in DC 2.4 when exposed to blank MP, VLP Suspension, VLP MP and VLP MP+Alum MP. Higher expression of MHC II was found in the VLP MP in comparison to all other groups (**p<0.001). In addition, VLP MP showed higher MHC Class II expression in comparison to VLP suspension and VLP MP+Alum MP (*p<0.05).

FIG. 19 shows MHC Class II expression in DC 2.4 when exposed to blank MP, VLP Suspension, VLP MP and VLP MP+Alum MP. Higher expression of MHC II was found in the VLP MP in comparison to all other groups (**$p<0.001$). In addition VLP MP showed higher MHC Class II expression in comparison to VLP suspension and VLP MP+Alum MP (*$p<0.05$).

Figure 20:
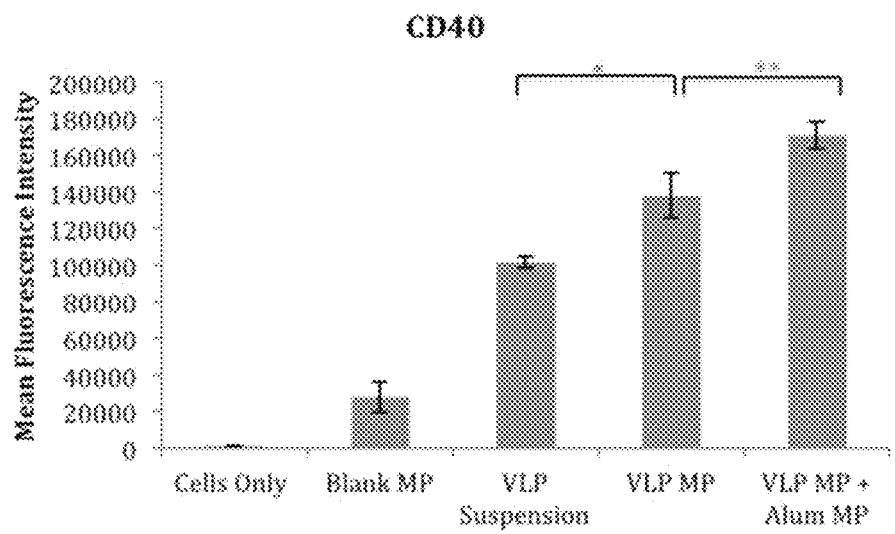
FIG. 20 illustrates a CD40 expression in DC 2.4 when exposed to blank MP, VLP Suspension, VLP MP and VLP MP+Alum MP. Higher expression of CD40 was found in the VLP MP in comparison to all other groups (*p<0.05). In addition, VLP MP+Alum MP showed higher CD40 expression in comparison to VLP suspension and VLP MP (**p<0.01).

FIG. 20 shows CD40 expression in DC 2.4 when exposed to blank MP, VLP Suspension, VLP MP and VLP MP+Alum MP. Higher expression of CD40 was found in the VLP MP in comparison to all other groups (*$p<0.05$). In addition VLP MP+Alum MP showed higher CD40 expression in comparison to VLP suspension and VLP MP (**$p<0.01$).

Buccal delivery of Microencapsulated Measles Vaccine Using Oral Dissolving Film

The main aim of this is study is to evaluate the potential of Oral disintegrating films (ODF) loaded with measles vaccine nanoparticles as a viable immunization strategy. In this preliminary study, 2 pigs were used as the in-vivo model to evaluate the immunogenicity of the measles vaccine formulation when administered via the buccal route.

Methods:

A 1% solution of sterile BSA in sterile water was prepared and kept for overnight crosslinking with glutaraldehyde. Excess glutaraldehyde was neutralized with sodium bisulphate the following day. Live attenuated measles virus is used as the antigen and Alum is used as adjuvant were added to the solution and spray dried using the Buchi Spray Dryer B-290. These nanoparticles were incorporated in the ODF. The film solution was prepared at room temperature by incorporating the film forming polymer (Lycoat RS720) in the aqueous plasticizer solution under continuous mixing for 10-15 minutes till the suspension is homogeneous and then combined with the measles vaccine nanoparticles powder. The film formulation was casted using a BYK-Gardner, mechanical drive Resource I equipment and dried (FIG. 1). The ODF formulation was tested in-vivo in 2 pigs via the buccal route. Blood serum samples were collected every 2 weeks and a specific ELISA was performed to quantify the amount of specific antibody present.

Results:

The size of the vaccine nanoparticles was in the range of 400 to 1200 nm. Using the pregelatinized hydroxypropyl pea starch, Lycoat RS720 we obtained the desired film strength and disintegration properties. There was a significant increase in the specific antibody against measles virus seen after 4 weeks of dosing. The levels continued to be high at 6 week also (FIG. 2).

Conclusion:

ODF loaded with the vaccine nanoparticles is a promising immunization delivery system using the buccal route. These encouraging preliminary results, will lead the way for further research in this area.

Figure 20A:
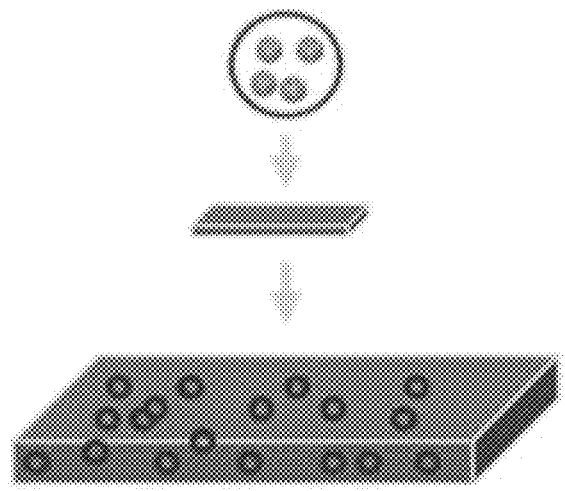
FIG. 20A illustrates a schematic diagram of measles antigen incorporated in the nanoparticles which is then loaded into an oral dissolving film.

FIG. 20A is a schematic illustration of measles antigen incorporated in the nanoparticles which is then loaded into an oral dissolving film.

Figure 21:
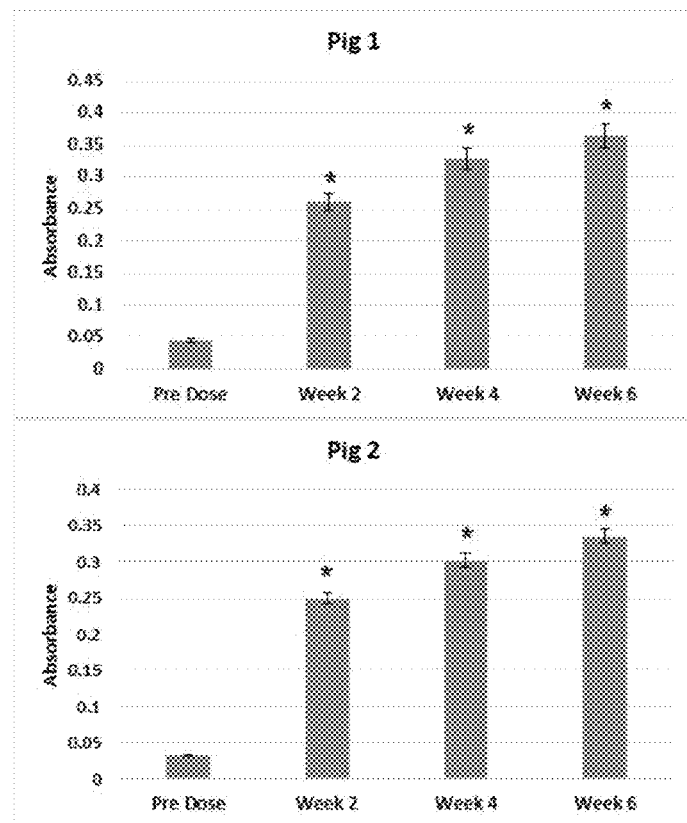
FIG. 21 illustrates there is significant higher level of antibody at week 2, 4 and 6 in comparison to pre-dose in the serum samples (n=4).

FIG. 21 shows that there is significant higher level of antibody at week 2, 4 and 6 in comparison to pre-dose in the serum samples (n=4).

Example 5

Immunomodulating Capacity and Intestinal Colonizing Potential of Lactobacilli Microspheres Leading to Vaccine Potentiation An expert panel commissioned by the Food and Agriculture Organization of the United Nations and the WHO in 2001 defined probiotics as 'live microorganisms which, when administered in adequate amounts, confer a health benefit on the host'. The probiotic bacteria most commonly studied include members of the genera *Lactobacillus* and *Bifidobacterium*.

Considerable research interest has been dedicated to the encapsulation of bacterial cells for the growing and promising potential in therapeutic applications such as in kidney failure uremia, cancer therapy, diarrhea, cholesteremia, and other diseases (2, 3, 4). Microorganisms used as probiotic adjuncts are commonly delivered in the food system. However, when these microorganisms are ingested, their activity and viability are reduced under highly acidic conditions (5). In addition, the usual starter organisms in yogurt are not bile-tolerant and do not colonize the intestines. Hence, there is a need for lactic acid bacteria products that are resistant to the stressful conditions of the stomach and the upper intestine, which both contain bile (6). Secondly for these bacteria to exert positive health effects, they have to reach their site of action alive and establish themselves in certain numbers (7). However, a major barrier to the survival of ingested microorganisms is the acidic environment (pH 2.0) of the stomach (8). Thus problems inherent with oral delivery have made the goal of oral delivery of live bacterial cells very challenging. Hence providing probiotic living cells with a physical barrier against adverse environmental conditions is therefore an approach currently receiving considerable interest (9).

Secondly the quality of probiotics has received very little attention; quality issues for probiotic supplement include the viability of microorganism in the product and the stability under different storage conditions. Analysis of products in several different countries has confirmed that probiotic strains exhibit poor survival in traditional probiotic foods such as yogurt and fermented milks (10).

Lactic acid bacteria used as starter cultures and adjuncts in fermented dairy products have been reported to have beneficial properties for health (11, 12, 31). (III). In particular, much interest has been focused recently on the immunological effects of the bacteria (6, 9, 13, 26, 27, 35).(III). Enhancement of the immune response has been suggested to be associated with the increased resistance to infection by pathogenic organisms (23, 24, 30, 32) (III) and anticarcinogenic properties that have been associated with lactic acid bacteria (9, 12, 29, 31)(III). There is extensive evidence that cytokines play a pivotal role in coordinating immune response (1) and the capacity to induce or enhance their production might be a major mechanism by which lactic acid bacteria exert their effect on the immune system.

Thus the objective of this study was to extract Lactobacilli species from capsules, formulate gastroresistant Lactobacilli microspheres and to evaluate the stability and suspendability of these Lactobacilli microparticles in vitro. After making Lactobacilli microspheres, blood was used to compare the ex-vivo effects of microencapsulated *Lactobacillus* spp. on cytokine production since effector cells of the innate immunity, such as macrophages, dendritic cells and neutrophils are present in blood.

Materials and Methods
Materials

Lactobacilli were extracted from iFlora capsules obtained from Sedona Labs (Providence Utah United States) by using MRS (deMan, Rogosa and Sharpe) broth and MRS Agar purchased from Fischer Scientific. 75 cm$^2$ vented cell culture flask, 25 cm$^2$ vented cell culture flask, Fisher Inoculating Turntables, culture plates and inoculating loops purchased from Fischer Scientific were used for cultivating these bacteria. The cell culture flasks were incubated in an incubator (Napco E series model 302 $CO_2$ incubator). Lactobacilli microparticles were prepared by using bovine serum albumin (BSA) (Fischer Scientific), ethylcellulose (EC) (FMC Biopolymer), Eudragit L 100-55 (Pharma Polymer-Degussa) and Sodium Hydroxide NaOH (F.W. 40.00) (Fischer Scientific). The formulation was spray dried using a mini spray dryer (Buchi 191) with a high efficiency cyclone. Stability studies of the formulation were carried out in a refrigerator (Kelvinator), room temperature and incubator (Type 37900 Culture Incubator). The suspendability of these microparticles was determined by using the Zeta Sizer (Malvern Instrument). Cytokine analysis was done by using Quantikine Immunoassay kit (Minneapolis, Minn.)

Method:
Extraction of Lactobacilli sp.:

Each Sedona capsule contains starch, Lactobacilli sp. and *bifidobacterium* sp. The method of culture of the bacterial organisms employed in each test is the most important factors in successful microbiological analysis. The bacterial cells can be expected to respond properly as test organisms only when they are in optimum nutrition. Hence the content from the capsule was first rehydrated in Man-Rogosa-Sharpe broth (MRS) to obtain a suspension. 500 µl of this suspension was then plated on an MRS agar plate, which was incubated at 37° C., in a 5% $CO_2$ atmosphere for 72 hours. The lactobacilli colonies thus obtained were gram stained and were checked under oil immersion lens. The purpose of this was to differentiate and isolate the lactobacilli from the rest of the capsule contents like starch and bifidobacteria. The colonies obtained were then gently emulsified in MRS broth, incubated at 37° C., in a 5% $CO_2$ atmosphere for 72 hours. MRS broth was used since it supports luxuriant growth of all lactobacilli. The MRS broth with the lactobacilli was then centrifuged at 2000 rpm (rotations per minute), for 30 minutes, at 4° C. The top supernatant was discarded and the bacteria which settle at the bottom of the tube were again subcultured in fresh MRS broth. Cells were then cultured in the same conditions for three successive transfers in MRS broth at 37° C. for 72 hours at the end of which, the bacteria were suspended in fresh broth and an equal amount of 20% (V/V) glycerol. This mixture containing lactobacilli sp. MRS broth and 20% glycerol were then aliquoted in separate cryogenic vials and stored at −80° C. until further use for making gastroresistant Lactobacilli microspheres.

After extracting Lactobacilli from the capsule contents the next step would be to formulate gastroresistant Lactobacilli microspheres. The two formulations that were tried are F1 and F2. For F1 formulation Eudragit L 100-55 was used as an enteric coating agent because of its resistance to gastric fluid. HPMCAS (Hydroxy Propyl Methyl Cellulose Acetate Succinate), Ethylcellulose (EC) and Bovine Serum Albumin were used as the polymer matrix for formulation F2.

Formulation 1 (F1):

Different concentrations of Eudragit L 100-55 were prepared in 0.02 M NaOH, 0.05 M NaOH and in 0.1 M NaOH as indicated in Table 2 below.

TABLE 2

| Concentration (w/v) | Eudragit (gm) | 0.02M NaOH (ml) |
|---|---|---|
| 0.50% | 0.05 | 10 |
| 1.00% | 0.1 | 10 |
| 2.00% | 0.2 | 10 |
| 3.00% | 0.3 | 10 |

TABLE 2-continued

| Concentration (w/v) | Eudragit (gm) | 0.02M NaOH (ml) |
|---|---|---|
| 4.00% | 0.4 | 10 |
| 5.00% | 0.5 | 10 |
| 2.00% | 0.2 | 10 |
| 7.50% | 0.75 | 10 |
| 15% | 1.5 | 10 |

In order to make micro spheres of Lactobacilli the dry weight of these bacilli was estimated by first doing the plate count and then by freeze drying 0.7 ml of bacteria in a Labconco Centrivap Concentrator. Thus of all the above concentrations, 2.0% (w/v) of Eudragit L 100-55 in 0.05 M NaOH formed a completely soluble and clear solution and hence was selected for microencapsulating lactobacilli, since this concentration of polymer matrix was higher and would be able to microencapsulate the entire lactobacilli content and thus provide gastric protection to these bacilli. For spray drying purposes, Lactobacilli Sp. Previously stored at −80° C. were first gradually thawed down to room temperature, after which the cells were harvested by centrifugation at 2000 rpm (rotations per minute), for 30 minutes, at 4° C. and resuspended in a small volume of sterile deionized water. 25% of Lactobacilli Sp. Was added to the 75% of 2.0% (w/v) Eudragit suspension in 0.05 M NaOH just prior to spray drying. The suspension was stirred using a magnet mixer until a homogenous mixture of Lactobacilli in Eudragit was obtained. Sample was then dried with a laboratory mini spray dryer (Buchi 191), at a Pump Flow Rate of 70 psi, a constant feed rate of 5 ml/min, at an aspiration rate of 55% and an air inlet temperature of 110° C. The resultant outlet air temperatures of 74° C. were recorded from the digital outlet temperature display on the spray dryer Formulation 2 (F2):

HPMCAS was dissolved in PBS pH 7.4 overnight to dissolve the polymer under stirring condition. In a separate beaker, BSA was dissolved in deionized water followed by addition of EC suspension under stirring. bacteria were then added before the solution was spray dried using a Mini Spray Dryer (Buchi 191).

In Vitro Characterization

The microspheres prepared were characterized using several instruments and techniques in order to determine the physical and chemical aspects of the microspheres.

Product Yield

The percentage yield of the microspheres obtained was determined using the following equation:

$$Y\% = (Ws \times 100)/Wpc$$

Where Ws is the weight of the microspheres obtained in the flask and Wpc corresponds to the dry weight of the cells and the polymer dispersion together Determination of Viability of *Lactobacillus* Sp. In Spray-Dried Microparticles 100 mg of lactobacilli-loaded microparticles were gently homogenized with a pestle and a mortar in 9.9 ml of MRS broth. The sample was aseptically diluted in MRS broth and the appropriate dilutions plated on MRS agar culture, and incubated at 37° C., in a 5% $CO_2$ atmosphere for 72 hours. The colony forming unit (cfus) were counted to assess survival. Average viability of lactobacilli was determined by plating more than three samples of lactobacilli microspheres after appropriate dilutions. Before spray drying the number of bacteria was determined as cfu $g^{-1}$ dry weight from cfu $ml^{-1}$ after completely freeze drying (Labconco Centrivap Concentrator) a known volume of the original sample used for plating and compared with the amount of viable bacteria per gram of spray-dried microparticles. The encapsulation efficiency was thus calculated by using the formula ((actual/theoretical)*100)

Particle Size Analysis

Particle size analysis was performed for all the microsphere formulations prepared using a Spectrex PC 2000 Laser particle counter. For the determination of the particle size, the microspheres were suspended in a vial containing 10 ml of deionized water filtered through 0.22 μm filter. The microsphere suspension was sonicated for 2 minutes before the particle size measurement.

Stability of Lactobacilli-Loaded Microparticles During Storage at 4° C., Room Temperature and 37° C.

A sample of free flowing lactobacilli-loaded HPMCAS—Ethylcellulose microparticles were aliquoted in three separate eppendorfs and each were stored for over 8 months at three different temperatures of 4° C., room temperature and 37° C. At predetermined time intervals, 100 mg of samples was collected and gently homogenized with a pestle and a mortar in distilled water. The suspension was plated on MRS agar plate, and incubated at 37° C., in a 5% $CO_2$ atmosphere for 72 hours. The colony forming unit (cfus) were counted to assess survival of bacteria when the microspheres were stored at different temperatures.

Determination of Zeta Potential

Zeta Potential is an indicator of suspendability of microspheres. If the Zeta Potential is 0 then there are aggregates. If the Zeta Potential is extreme − or + then the microspheres have good suspendability and are well separated. For the measurement of zeta potential, PBS buffers of pH 6.8, pH 7.4 and deionized water were filtered using 0.2 mm syringe filter. An optimized amount of microspheres was suspended in deionized water and transferred using a syringe into the zeta potential measurement cuvette which has integrated gold electrodes. The sample loaded cuvette was placed in the instrument for zeta potential measurement. The Zetasizer nano series used in this project uses a combination of Laser Doppler velocimetry and phase analysis light scattering (M3-PALS technique) to measure particle electrophoretic mobility.

Table 3: Illustrates different groups of study for ex-vivo evaluation of the effect of Lactobacilli microspheres on cytokine production.

TABLE 3

| Study Group | No. of Subjects | Dose of bacteria |
|---|---|---|
| Lactobacilli | 6 | 10^5 |
| Lactobacilli MS | 6 | 10^5 |
| Blank MS | 6 | — |
| +Control | 6 | LPS |
| −Control | 6 | — |

Results

Counting microorganisms from particulate or solid samples is often difficult. In such cases, it is important to separate cells from the particles. This can be achieved by using specific media for specific organisms. The type of media and nutrients for selective enumeration of Lactobacilli sp. can have an effect on growth characteristics (Rao et al 1989; Duby and Mistry, 1996^). The MRS broth and yeast extract may act as useful nutrients (Rao et al; Duby and Mistry, 1996) (b). Hence in this case MRS media was used for the isolation and cultivation of Lactobacilli sp. that are needed to make Lactobacilli microspheres.

The most conspicuous feature of gram stained Lactobacilli cells are that they are straight and uniform with rounded ends and may form chains as shown on FIG. 2.

The development of drug delivery micro particles, made of a combination of polymers, is receiving increasing attention in the field of microencapsulation. These systems offer significant advantages over the classical one-polymer based microcapsules: (1) by selecting the appropriate core/coating polymer combination it is possible to achieve the encapsulation of hydrophilic and hydrophobic drugs simultaneously; (2) the active ingredient can be conveniently isolated and protected in the microcores; and (3) the core material provides the coating polymer with an additional element for controlling the release. (a) Thus the aim of this study was to device a cost-effective method of producing microspheres containing viable Lactobacilli Sp. cells and to investigate whether the HPMCAS and ethylcellulose material used as the coating polymer afforded the probiotic strain protection during spray drying and during storage at different temperatures. Encapsulation, entrapment or immobilization are terms used almost interchangeably in the food industry to refer to the provision of an outer protective coat or layer to protect the material from damage. The application of these methodologies to improving probiotic survival in foods is relatively new. To date, most published reports have focused on the utilization of coacervation methods to coat probiotic strains with calcium alginate and have documented various degrees of success. However, the scale-up of coacervation-type processes for commercialization purposes can be problematic. Conversely the process of spray drying is economical and can be easily scaled-up (c).

Figure 22:
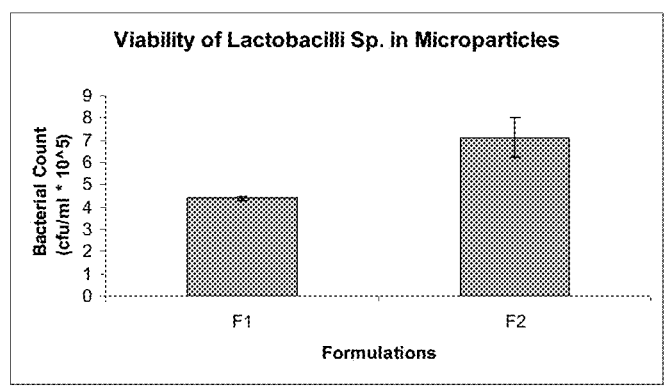
FIG. 22 illustrates a viability of Lactobacilli sp. in microparticles made by F1 and F2 formulations.

The process of spray drying is influenced by the operating parameters used. The latter includes air flow rate, inlet temperature, spray rate of feed, and atomization air pressure (33) (d). The no instrumental factors known to affect the production of microparticles include composition of feed and concentration and the nature of polymer and plasticizer being used in feed. The air flow rate controls the residence time of feed droplets in the drying chamber. A decrease in the air velocity increases the residence time of feed droplets in the drying chamber, which, in turn, causes a decrease in moisture content of the product. Reducing air velocity also assists product recovery from the drying chamber. The inlet temperature (or drying air temperature) at a constant air flow rate controls the drying rate of feed droplets as they are nebulized in the drying chamber. It must be set at a higher temperature than the boiling point of the dispersion medium or solvent used in the preparation of feed. Also, it must not degrade the materials to be dried. Hence the inlet temperature in this case was set at 110° C., which is higher than the boiling point of water which was used as a dispersion medium. Increasing inlet temperature typically results in a more porous or fragmented structure of the product. The spraying rate of the feed influences the efficacy of the drying process as well as the size and shape of the particles. In general, faster spray rate of feed produces larger volumes of nebulized solution/dispersion droplets. This causes the spray-dried particles to be coarser and larger in size and with high moisture levels, owing to the incomplete drying before leaving the drying chamber. Hence the feed rate was set at 5%. The atomization air pressure assists breaking of liquid feed into fine droplets. A decrease in air pressure causes an increase in the spray angle and as a result feed droplets (may) condense on the walls of the drying chamber. (d) Hence the aspiration rate was set at 55%.

Different concentrations of Eudragit L 100-55 showed varied solubilities in 0.02 M, 0.05 M and 0.1 M NaOH respectively as shown in Table 4.

TABLE 4

Solubilities of different concentrations of Eudragit L 100-55 in 0.02M, 0.05M and 0.1M NaOH

| | Approximate time taken to dissolve (hrs.) | Solubility | Clarity |
|---|---|---|---|
| Concentration (w/v) in 0.02M NaOH | | | |
| 0.50% | 8 | + | + |
| 1.00% | 8 | + | + |
| 2.00% | 24 | + | — |
| 3.00% | 30 | + | — |
| 4.00% | 43 | + | — |
| 5.00% | 43 | — | — |
| Concentration (w/v) in 0.05M NaOH | | | |
| 2.00% | 24 | + | + |
| 7.50% | 48 | + | — |
| Concentration (w/v) in 0.1M NaOH | | | |
| 15.00% | 48 | + | — |
| | 4 | — | — |

Key for Table
Solubility
+ indicates complete solubility and uniformity of solution
— indicates that it is not completely soluble and does not form an uniform solution
Clarity
+ indicates that the solution is clear and transparent
— indicates that the solution is turbid Thus of all the above concentrations, 2.0% (w/v) of Eudragit L 100-55 in 0.05 M NaOH formed a completely soluble and clear solution and hence was selected for microencapsulating lactobacilli, since this concentration of polymer matrix Eudragit L 100-55 was higher than 0.5% and 1.0% and would be able to microencapsulate the entire lactobacilli content and thus provide gastric protection to these bacilli. The above cultured Lactobacilli Sp. was added to this 2.0% (w/v) Eudragit suspension just prior to spray drying. Sample was then dried with a laboratory mini spray dryer (Buchi 191).

Previous reports indicated that survival of probiotics or lactic acid bacteria during spray drying decreased with increasing inlet temperatures (C) (Mauriello 1999). Thus in our case microspheres were prepared using the mini spray dryer (Buchi 191), 110° C. was chosen to be the optimal inlet temperature as it afforded good drying and the resultant outlet temperature (mean temperature of 55° C.) permitted good bacterial survival. The yield and the viability (%) after microencapsulation obtained are as indicated in Table 5.

TABLE 5

(Product yield and encapsulation efficiency of live bacteria after making spray dried microspheres.)

| Formulation | Product Yield | Encapsulation Efficiency of live bacteria |
|---|---|---|
| F1-Bacteria + 2% Eudragit in 0.05M NaOH | 38% | 75% |
| F2-Bacteria + 5% HPMCAS + 15% Ethylcellulose + BSA | 45.2% | 100% |

Table 5 indicates that F2 proved to be a better formulation than F1 based on product yield and encapsulation efficiency. The encapsulation efficiency of live bacteria was 100% in F2 formulation after the spray drying process. This is essential to attain any positive effects from these Lactobacilli microspheres FIG. 22 shows the viability of Lactobacilli sp. in microparticles made by F1 and F2 formulations.

100 mg of lactobacilli-loaded microparticles were gently homogenized with a pestle and a mortar in 9.9 ml of MRS broth. The sample was aseptically diluted in MRS broth and the appropriate dilutions plated on MRS agar culture, and incubated at 37° C., in a 5% $CO_2$ atmosphere for 72 hours. The colony forming unit (cfus) were counted to assess survival.

Figure 23:
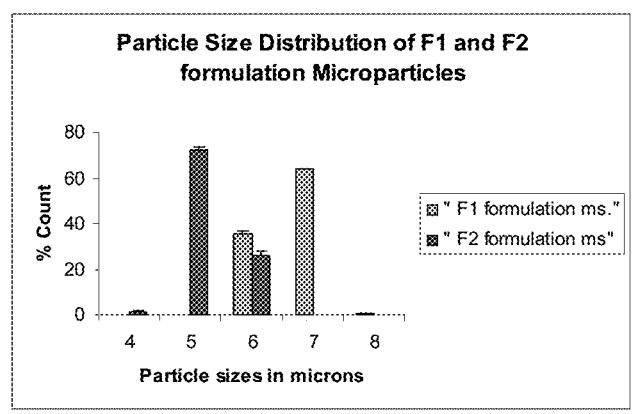
FIG. 23 illustrates a particle Size Distribution of F1 and F2 formulation microparticles.

Lactobacilli have shown to retain their viability in FIG. 23 after the spray drying process. This is essential to attain any positive effects from these Lactobacilli microspheres FIG. 23: Particle Size Distribution of F1 and F2 formulation microparticles.

The size distribution was measured using the Spectrex laser particle counter with a laser diode of wavelength of 670.8 nanometers as the source of light. The percent particle count per size category ranging from three to twenty microns was determined and analyzed for particle size distribution.

FIG. 4 shows that most of the microparticles of F1 formulation are 7µ in size and most of the microparticles of F2 formulation are 5µ in size. Particle sizes of microspheres also play an important role during uptake through the M-cells present in the Peyer's Patches on the intestines and by antigen presenting cells that mediate immune responses. Norris and Sinko, 1997 and Szentkuti, 1997 found that microspheres that have diameters smaller than 10 µm have the advantage of being more easily able to penetrate the mucus layer to reach the apical membrane of the epithelium cells. 3-5 micron size range microparticles have been found to be ideal for oral delivery. And since F2 formulation has most of its particles in the range of 5µ this formulation was selected to proceed on further studies.

Figure 24:
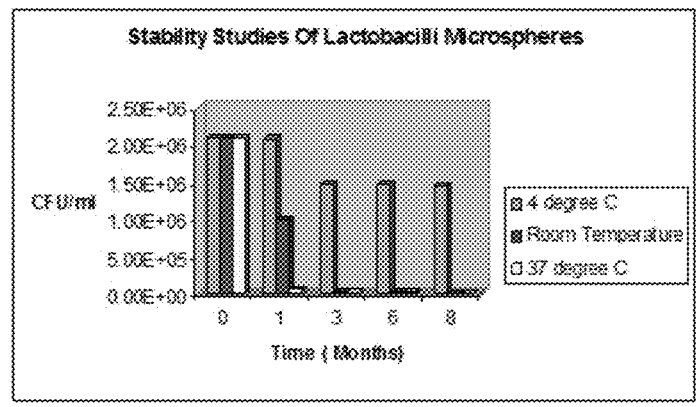
FIG. 24 illustrates a stability studies of lactobacilli microspheres when stored at 4° C., Room temperature and 37° C. At predetermined time intervals, 100 mg of samples was collected and gently homogenized with a pestle and a mortar in dist. water. The suspension was plated on MRS agar plate, and incubated at 37° C., in a 5% $CO_2$ atmosphere for 72 hours. The colony forming unit (cfus) were counted to assess survival of bacteria when the microspheres were stored at different temperatures.

FIG. 24 shows stability studies of lactobacilli microspheres when stored at 4° C., Room temperature and 37° C. At predetermined time intervals, 100 mg of samples was collected and gently homogenized with a pestle and a mortar in distilled water. The suspension was plated on MRS agar plate, and incubated at 37° C., in a 5% $CO_2$ atmosphere for 72 hours. The colony forming unit (cfus) were counted to assess survival of bacteria when the microspheres were stored at different temperatures.

Table 6 signifies that Lactobacilli microspheres are most stable when stored at 4° C. as compared to room temperature and 37° C. The viability of the bacteria decrease significantly in microspheres stored at room temperature and 37° C.

TABLE 6

(Zeta Potential of F2 formulation in PBS buffers of pH 6.8 and 7.4 and in distilled water was found using the Zetasizer nano series from Malvern instruments.)

| Buffer | PBS, pH 7.4 | PBS, pH 6.8 | Deionized water, pH 6.5 |
|---|---|---|---|
| Zeta Potential | −15.37 | −14.58 | −32.39 |

The general dividing line between stable and unstable suspensions is generally taken at either +30 mV or −30 mV are normally considered as stable. The Zeta Potential is as dependent on the composition of the disperse phase as it is on the nature of the particle surface. The most important factor that effects zeta potential is pH. A zeta potential value on its own without a quoted pH is a virtually meaningless number. The Zeta potentials of the microspheres as seen in table 3 indicate that these microspheres show a better suspendability in distilled water compared to the buffers, since buffers have charges that contribute to the charge on the polymer, distilled water on the other hand has no charges.

To evaluate the effect of Lactobacilli microspheres on intestinal colonization and to check the immunomodulating capacity of these Lactobacilli microspheres in-vivo using Sprague Dawley rats.

Lactobacilli microparticles were prepared by using a bovine serum albumin (BSA)-Hydroxy Propyl Methyl Cellulose Acetate Succinate (HPMCAS)-ethylcellulose (EC) matrix system. The formulation was spray dried using a mini spray dryer (Buchi 191). Various parameters for the spray dryer viz: inlet temperature, pump flow, aspiration rate and air pressure were optimized. Product yield and encapsulation efficiency of the microparticles were done after the spray drying process to quantify the amount of bacteria that has been encapsulated in spray-dried powder. Sprague-Dawley rats were used for in-vivo evaluation of effect of Lactobacilli microspheres on intestinal colonization and to check the immunomodulating capacity of these microspheres. Wherein rats were orally dosed with Lactobacilli loaded microspheres every second day for two weeks. Blood samples and fecal samples were collected before each dosing period. Blood samples were analyzed for TNF-alpha and IL-1-beta cytokine levels by ELISA since cytokines are known to be the coordinators of immune function. The blood samples, fecal samples, nasal and intestinal wash samples collected on sacrificing the rat were all analyzed for IgA levels by ELISA to check if these Lactobacilli microspheres can induce mucosal immunity. Fecal samples and intestinal wash samples were analyzed for bacterial count by culturing on MRS Agar to check if these microspheres can induce intestinal colonization which is prerequisite for any health benefits to be conferred.

Lactobacilli microspheres maintained intestinal colonization only during the dosing period and the colonization decreased significantly after stopping dosing. The serum IgG levels were higher in the Lactobacilli microsphere group compared to the blank microsphere and the lactobacilli solution group. Similarly there was a slight increase in serum IgA compared to the other two groups. The fecal, intestinal and nasal IgA levels and the serum IL-1-beta levels were higher in the Lactobacilli microsphere group compared to the blank microsphere and the lactobacilli solution group. The Lactobacilli microspheres did not have a significant effect on the TNF-alpha levels due to antagonistic effects of cytokines.

Lactobacilli microspheres have shown to maintain intestinal colonization only during the dosing period, since Lactobacilli do not permanently colonize the host, they need to be ingested regularly for any health promoting properties to persist. The results obtained from this investigation showed that Lactobacilli microspheres were successfully able to induce both systemic and mucosal immunity, which is suggestive of induction of nonspecific immune response. Lactobacilli microspheres also increased IL-1-beta levels in vivo which are the co-coordinators of immune function. Thus suggesting that these Lactobacilli microspheres successfully induced nonspecific immunity.

In this study we also wanted to see if Lactobacilli microspheres could induce the production of Immunoglobulin A (IgA) and Immunoglobulin G (IgG) since IgA is an antibody playing a critical role in mucosal immunity. More IgA is produced than all other types of antibody combined.[1] In its secretory form, IgA is the main immunoglobulin found in mucous secretions, such as, but not limited to, tears, saliva, colostrum, intestinal juice, vaginal fluid and secretions from the prostate and respiratory epithelium. It is also found in small amounts in blood. Because it is resistant to degradation by enzymes, secretory IgA can survive in harsh environments such as the digestive and respiratory tracts, to provide protection against microbes that multiply in body secretions.[2] The gut mucosa plays a central role in the exclusion and elimination of potentially harmful dietary antigens and microorganisms, while providing selective absorption of nutrients (Brandzaeg 1995). Antigen exclusion has been associated with factors such as the capacity of the gut mucosa to produce secretory IgA and mucus (Slomiany et al. 1987, Stokes et al. 1975). Secretory IgA prevents the adherence of enteral antigens to the mucosal surface, and mucus prevents microbial infestation.

Lactobacilli microspheres were evaluated for its ability to induce IgG levels since IgG antibodies are very important in fighting bacterial and viral infections. "The IgG class of antibodies is a critical part of the human immune system, guarding us against infection by an endless array of microorganisms," says Nohturfft, associate professor of molecular and cellular biology in Harvard's Faculty of Arts and Sciences.

Lactobacilli microspheres were evaluated for its ability to induce cytokine production since cytokines are a group of low-molecular-weight regulatory proteins that serve as messengers of the immune system. Cytokines regulate the intensity and duration of the immune response by stimulating or inhibiting the activation, proliferation, and/or differentiation of various cells and by regulating the secretion of antibodies or other cytokines. Thus cytokines are critical components of both humoral and cell-mediated immune responses. (Janis Kuby 1997)

Evaluation of the Efficacy of Lactobacilli loaded microspheres on Intestinal Colonization and on Inducing Immunity:

Sprague Dawley rats (200-225 gm) were used for this study. The rats were dosed with 100 mg/kg of vancomycin, before starting the study. This was done to clear the gastrointestinal system from the entire normal flora present. After 48 hours this was considered as the 0 time point and blood and fecal samples were collected and the rats were dosed with blank microspheres, Lactobacilli loaded microspheres and Lactobacilli without encapsulation via the oral route with the aid of a blunt feeding needle, such that each rat received $10^9$ cfu/ml as indicated on table 1. The microspheres were dosed in the form of suspension in PBS buffer of pH 6.8. The rats were dosed every second day for two weeks. Blood samples from tail vein and fecal samples were collected before each dosing period. These blood samples were analyzed for IgG to check for systemic immunity and IgA levels to check for mucosal immunity by ELISA. The fecal samples were analyzed for IgA levels by ELISA. Natural antibodies like secretory IgA antibodies are the main host defense against the initial step of infection. Fecal samples were also analyzed for bacterial count by culturing on MRS Agar. This was done to check the efficiency of Lactobacilli microspheres to promote intestinal colonization. Blood samples were analyzed for TNF-alpha and IL-1-beta levels by ELISA. TNF-alpha and IL-1-beta are cytokines, and cytokines are known to be the messengers of the immune system that co-ordinate the immune function. At the end of the study, rats were sacrificed; nasal and intestinal wash samples were collected for the determination of IgA levels. Intestinal wash samples were also analyzed for bacterial count by culturing on MRS agar plates. This was done to check the ability of these Lactobacilli microspheres to maintain intestinal colonization after stopping dosing.

TABLE 7

In vivo study design groups and the specific doses for each group

| Study Group | No. of Animals | Dose of Lactobacilli |
| --- | --- | --- |
| Blank ms. Group | 4 | Blank micro spheres without lactobacilli |
| Lactobacilli ms. group | 6 | microspheres loaded with $10^9$ cfu |
| Lactobacilli Solution | 6 | $10^9$ cfu without encapsulation |

Determination of Effect of Lactobacilli Microspheres on Serum IgG Levels:

Blood samples were collected from the tail vein, centrifuged at 6000 rpm for 20 minutes at 4° C. Serum separated into a separate Eppendorf and stored at −80° C. till further analysis for IgG by ELISA.

Determination of Effect of Lactobacilli Microspheres on Serum IgA Levels:

Blood samples were collected from the tail vein, centrifuged at 6000 rpm for 20 minutes at 4° C. Serum separated into a separate Eppendorf and stored at −80° C. till further analysis for IgA by ELISA.

Results and Discussion

Effect of Lactobacilli Microspheres on Intestinal Colonization:

The beneficial effects of lactobacilli in the intestinal tract (antibiotic production, competitive antagonism, bile deconjugation, source of enzymes) are well known (Gilliland et al. 1979, Klaenhammer et al. 1982, Sandine 1979). The most-often mentioned as beneficial dietary adjuncts are *Lactobacillus acidophilus, L. casei*, and *L. bifidus (Bifidobacterium bifidum)*. Thus this study Lactobacilli microspheres containing a mixture of 10 different Lactobacilli sp. were used. The effects of Lactobacilli microsphere administration on intestinal colonization is shown on FIG. 1. Sprague-Dawley rats were used for in-vivo evaluation of effects of Lactobacilli microsphere administration on intestinal colonization. The rats were dosed from day 0 to day 10. Fecal samples were collected at the time points indicated on the x-axis. Samples collected from day 0 to day 14 were during the administration of Lactobacilli microspheres. Samples from day 17 to day 31 were collected after stopping Lactobacilli microsphere administration. There was increased intestinal colonization in the lactobacilli microsphere group from day 0 to day 14, which is one day after stopping administration compared to the blank microsphere and Lactobacilli solution group. The Lactobacilli count decreased significantly from day 17 to day 31 which is after stopping Lactobacilli microsphere administration. Thus indicating that Lactobacilli microspheres can maintain intestinal colonization only during the administration period.

Figure 25:
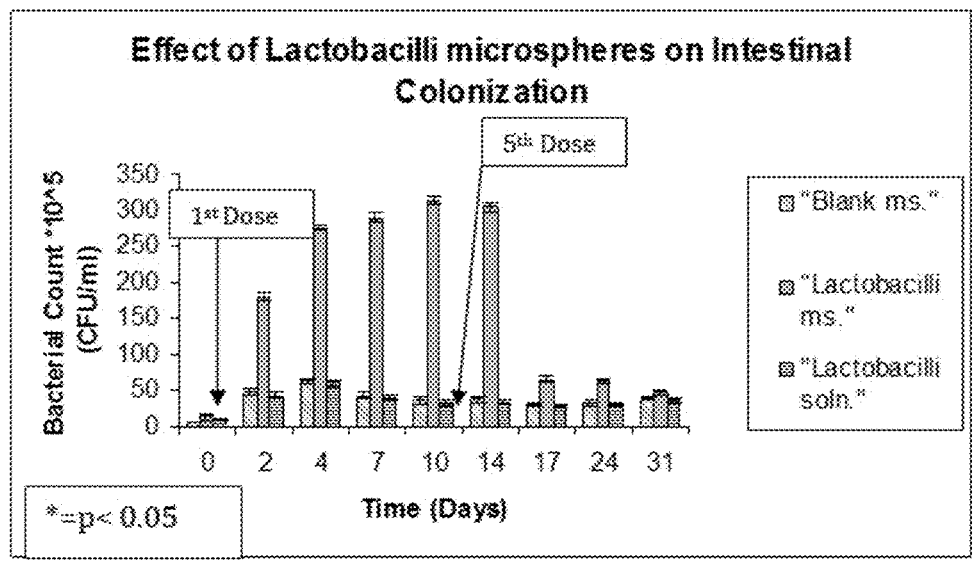
FIG. 25 illustrates a In vivo evaluation of the effect of Lactobacilli microspheres on intestinal colonization.

FIG. 25 shows an in vivo evaluation of the effect of Lactobacilli microspheres on intestinal colonization.

The rats were dosed with blank microspheres, lactobacilli microspheres ($10^9$ cfu/ml) and Lactobacilli solution ($10^9$ cfu/ml) from day 0 to day 10. Fecal samples were collected at the time points indicated on the x-axis. One pellet of fecal matter was collected from each rat in each Eppendorf to which PBS buffer was added. The eppendorfs were then vortexed till the feces were broken down into a suspension in PBS buffer and was plated on MRS agar. The agar plates were then incubated in an incubator at 37° C. under 5% $CO_2$ for 72 hours and after 72 hours the plate count done in colony forming unit (cfu/ml). Values are means for six rats per group, with their standard errors represented by vertical bars.

Samples collected from day 0 to day 14 were during the administration of Lactobacilli microspheres. Samples from day 17 to day 31 were collected after stopping Lactobacilli microsphere administration. There was increased intestinal colonization in the lactobacilli microsphere group from day 0 to day 14, which is one day after stopping administration compared to the blank microsphere and Lactobacilli solution group. The intestinal count decreased significantly from day 17 to day 31. Thus indicating that Lactobacilli microspheres can maintain intestinal colonization only during the administration period.

Figure 26:
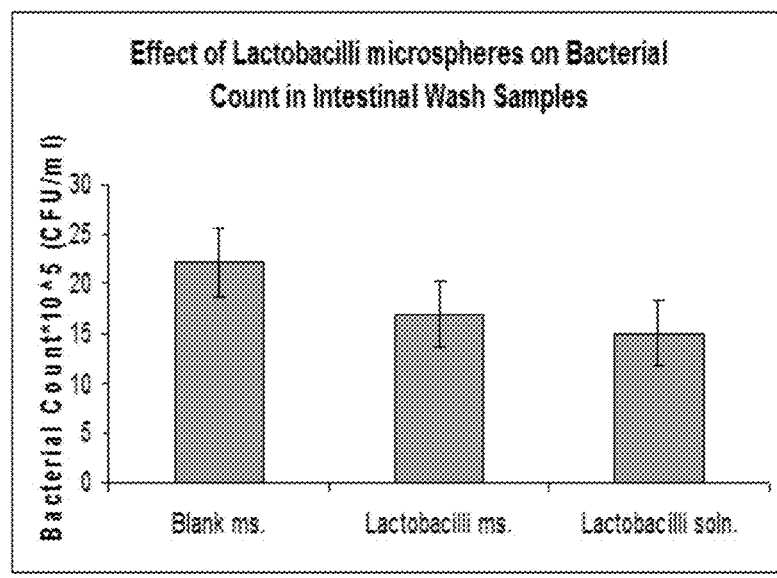
FIG. 26 illustrates a intestinal wash bacterial count indicating effect of Lactobacilli microspheres on intestinal colonization.

Effect of Lactobacilli Microspheres on Intestinal Wash Samples:

FIG. 26 shows the effect of Lactobacilli microspheres on bacterial count in intestinal wash samples. The intestinal wash samples were collected at the end of the study after stopping dosing. The lactobacilli microsphere group in FIG. 2 didn't show a significant increase in bacterial count thus indicating that once you stop dosing the intestinal colonization goes down which is in-line with the previous graph where intestinal colonization decreases significantly from day 17 to day 31 after stopping administration.

Intestinal wash samples were collected at the end of the study after sacrificing the rats on day 31. After sacrificing the rats, the intestine was separated from the rest of the parts of the gastrointestinal tract. The intestine was inverted and rinsed with protease inhibitor PBS buffer (pH 7.4). These intestinal wash samples obtained were plated on MRS agar to check for bacterial count.

Serum Immunoglobulin G (IgG)

Lactobacilli microspheres were evaluated for its ability to induce IgG levels since IgG antibodies are very important in fighting bacterial and viral infections. "The IgG class of antibodies is a critical part of the human immune system, guarding us against infection by an endless array of microorganisms," says Nohturfft, associate professor of molecular and cellular biology in Harvard's Faculty of Arts and Sciences. For in vivo testing of IgG antibody titer, five standard curves were obtained from five separate ELISA assays performed at different times and days from 08-14-07 to 09-13-07. The standard curve obtained from the correlation of the absorbance of the standards to their concentration (FIG. 3) showed a high $R^2$ of around 0.9977 (FIG. 3). This indicates that the enzyme-linked immunosorbent assay was highly sensitive for the detection of IgG. The linear IgG std concentration range was from 0.031 to 3.91 ng/ml on an average. The IgG std absorbances ranged from 0.1345 to 1.009 on an average. The five consistent, linear IgG standard curves generated indicate that the ELISA assay for the quantification of IgG was well optimized.

Determination of Effect of Lactobacilli Microspheres on Serum IgG Levels:

Sprague-Dawley rats were used for in-vivo evaluation of effect of Lactobacilli microspheres on serum IgG levels. Oral administration with lactobacilli microspheres was compared with oral administration of blank microspheres and lactobacilli solution. Blood samples were collected by tail vein puncture and the serum samples were analyzed by sandwich ELISA for serum IgG levels. FIG. 4 illustrates the serum IgG levels obtained at different time points of the Lactobacilli microsphere evaluation study.

The levels of IgG antibodies produced were significantly higher in the group dosed with Lactobacilli microsphere compared to the groups dosed with blank microsphere and the Lactobacilli solution respectively. The Lactobacilli microspheres gradually induced IgG antibody levels from day 7 to day 24 where the increase in IgG levels was the highest and then decreased on day 31 this could have been due to the fact that we stopped dosing with Lactobacilli microspheres from day 11. Thus indicating that these Lactobacilli microspheres have the ability to induce systemic immunity.

Figure 27:
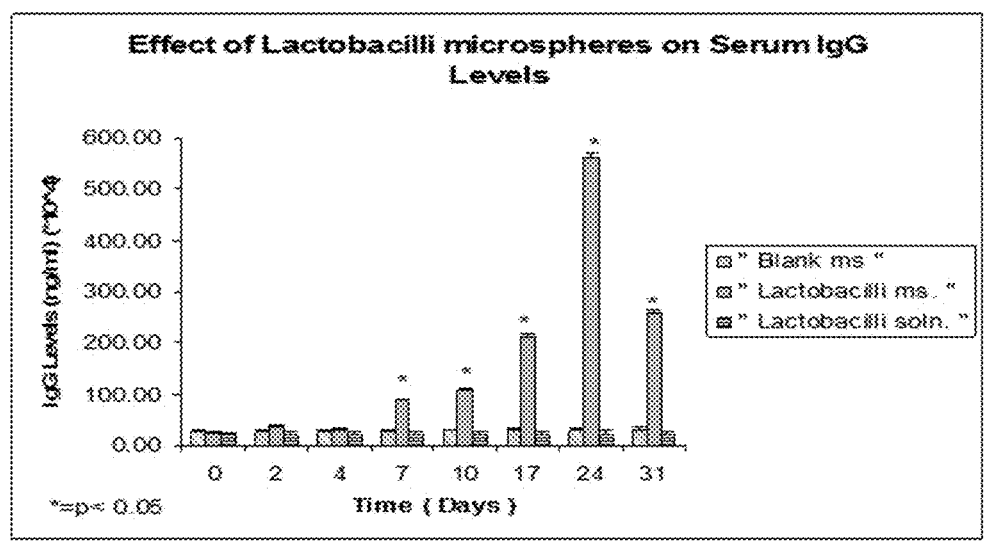
FIG. 27 illustrates an effect of Lactobacilli microspheres on serum IgG levels.

FIG. 27 shows the effect of Lactobacilli microspheres on serum IgG levels

The rats were dosed every second day from day 0 to day 10. Blood samples were collected from the tail vein on the time points indicated on the x-axis and the serum samples were analyzed for IgG levels by ELISA. Values are means for six rats per group, with their standard errors represented by vertical bars.

Serum Immunoglobulin A (IgA)

Lactobacilli microspheres were evaluated for its ability to induce mucosal immune response through the induction of IgA levels. Natural antibodies like secretory IgA antibodies can block bacterial attachment to mucosal epithelium cells, and are hence the main host defense against the initial step of infection. These natural antibodies are important for defense against pathogens. The intestinal mucosa constitutes a major host barrier against foreign antigens encountered by the enteral route. IgA is responsible for immune exclusion of luminal antigens and may dampen local inflammatory reactions (Brandtzaeg P, (1989)). For in vivo testing of IgA antibody titer, six standard curves were obtained from six separate ELISA assays performed at different times and days from 05-04-07 to 07-17-07. The standard curve obtained from the correlation of the absorbance of the standards to their concentration (FIG. 5) showed a high $R^2$ of around 0.9998 (FIG. 5). This indicates that the enzyme-linked immunosorbent assay was highly sensitive for the detection of IgA antibodies. The linear IgA standard concentration range was from 0.1225 to 15.6 ng/ml on an average. The IgA standard absorbances ranged from 0.2835 to 1.6695 on an average. The six consistent, linear IgA standard curves generated indicate that the ELISA assay for the quantification of IgA was well optimized.

Serum IgA

The main objective of the study was to evaluate the effect of Lactobacilli microspheres on inducing mucosal immune response. In this study the rats were dosed every second day for two weeks. Blood and fecal samples were collected at the time points indicated on the x-axis. Thus the sample collection went on for 31 days. The samples were analyzed for IgA levels by ELISA. FIG. 6. shows the effect of Lactobacilli microspheres on serum IgA levels. Lactobacilli microspheres did not show a significant increase in IgA levels initially but showed an increase from day 17. This is because when an animal is injected with an antigen, it produces a primary serum antibody response of low magnitude and relatively short duration, peaking at about 10-17 days. (Janis Kuby—1997). There is no increase in serum IgA levels in the first 10 days, since IgA constitutes only 10%-15% of the total immunoglobulin in serum, it is predominant immunoglobulin class in external secretions such as breast milk, saliva, tears, and mucus of the bronchial, genitourinary, and digestive tracts.

Figure 28:
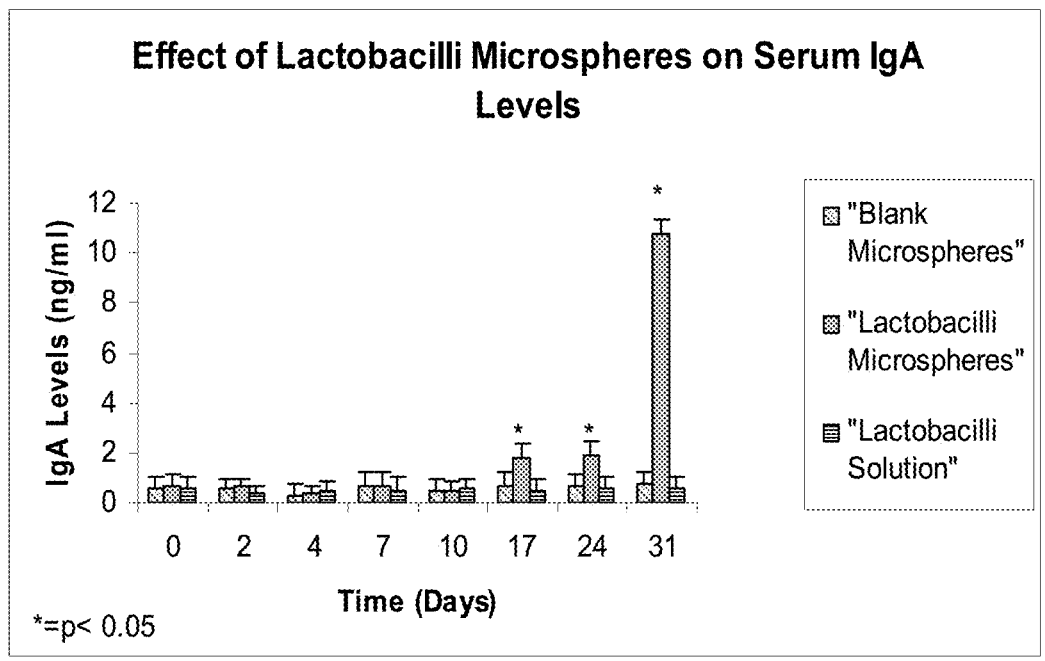
FIG. 28 illustrates an effect of Lactobacilli microspheres on serum IgA levels.

(Janis Kuby—1997) Hence it is observed that Lactobacilli microspheres increased serum IgA only from day 17 but increased fecal IgA on day 7 onwards. Secondly Lactobacilli microsphere administration showed an increased IgA titer on day 31. This is because a second immunization with the same antigen results in secondary response that is greater in magnitude, peaks in less time (2-7 days) and lasts longer (months to years) than the primary response (Janis Kuby—1997). However, titres of the serum IgA were relatively lower than the serum IgG in the study. This is not surprising since systemic IgA production is relatively limited as compared to other antibody types. Also, the level of IgA antibody produced was significantly higher in the Lactobacilli microsphere group animals compared to the blank microsphere group and the Lactobacilli solution group animals FIG. 28 shows the effect of Lactobacilli microspheres on serum IgA levels.

The rats were dosed every second day from day 0 to day 10. Blood samples were collected from the tail vein on the time points indicated on the x-axis and the serum samples were analyzed for IgA levels by ELISA. Values are means for six rats per group, with their standard errors represented by vertical bars.

Example 6

Development of Microparticulate Gonorrhea Vaccine

We examined the uptake of gonococci NPs in murine macrophages as well as in DC.2 dendritic cells. We also looked at autophagy induction in murine macrophages using these Gc-NP in presence and absence of adjuvants NPs. Figure shows that gonococci whole cell NPs are recognized by macrophages (RAW264) and elicited immune response represented by nitric oxide release. The data suggest that these gonococci NPs are biologically active, taken up by macrophages, which is a prerequisite to antigen presentation, therefore could elicit a protective antibody response.

Figure 29:
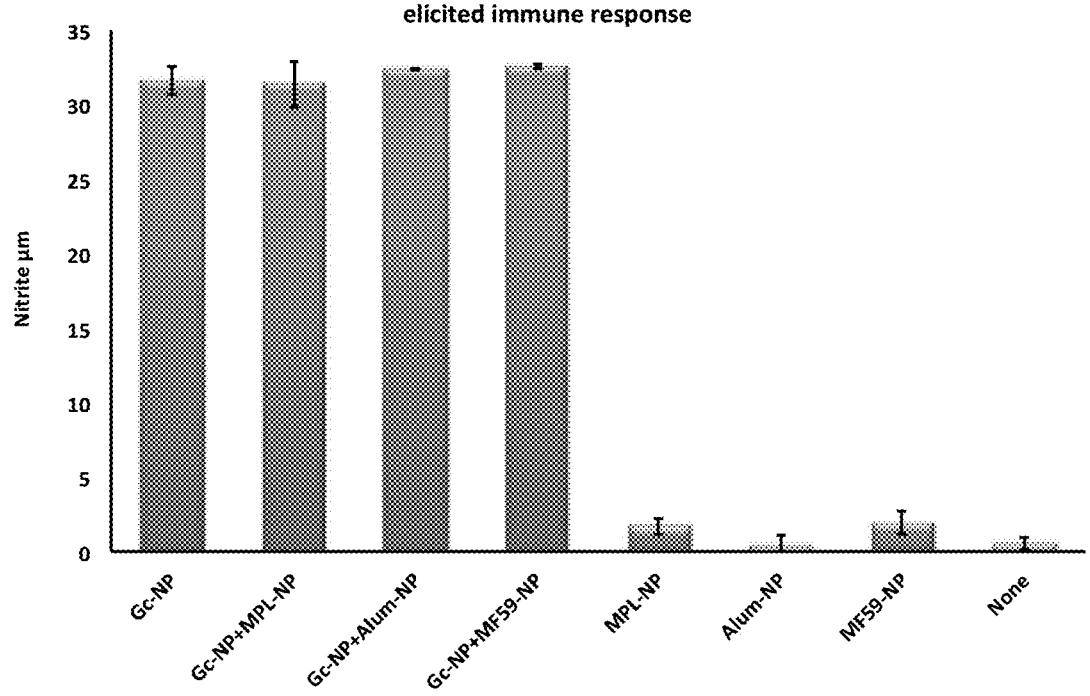
FIG. 29 illustrates nitric oxide release from RAW264 macrophages stimulated with Gonococcal whole cell NP with or without adjuvant NP.

FIG. 29 shows nitric oxide release from RAW264 macrophages stimulated with Gonococcal whole cell NP with or without adjuvant NP. The data suggest that Gc-NPs are biologically active in macrophages and elicited immune response.

Microencapsulation of Pancreatic Islet Beta Cells for Treatment of Insulin Dependent Diabetes This research evaluates the fabrication of microtissue encapsulating pancreatic islet beta cells (Beta-TC-6) in alginate microcapsules coated with chitosan, as therapy for type I diabetes mellitus. The biocompatibility and semipermeable nature of these alginate polymers, in addition to their ability to provide immune protection and their high mechanical properties appears to be a promising strategy for cell encapsulation. In this study, encapsulated cells were evaluated for cell viability, secretion of insulin in the presence of glucose.

Introduction

Diabetes mellitus is a chronic metabolic disease and is one of the primary causes of mortality in well developed countries. The causative factor responsible for none or underproduction of insulin is due to destruction of pancreatic beta cells in type I diabetic patients. The first line therapy is to inject insulin directly to patients or either organ transplant. Our strategy is to enclose (encapsulate) pancreatic beta cells in polymeric microcapsules. This technology works by encapsulating the cells in a semipermeable membrane that allows the entry and exit of small molecules like oxygen and proteins like insulin (Mol wt—6 KDa These cells can produce the protein of interest de novo and deliver the biotherapeutic molecules in the body. The advantage of our proposed strategy over existing therapy would limit the dosing frequency and circumvent the need for organ transplantation Method Microcapsules were prepared by spraying a sucrose-alginate-beta cell suspension mixture into calcium chloride solution using a specialized spray nozzle. Calcium alginate microcapsules containing cells were coated with chitosan glutamate to form a semipermeable membrane at the surface. Various concentrations of sodium alginate, chitosan glutamate and calcium chloride were varied for optimal size and sphericity. Cell viability was measured using fluorescent staining.

Figure 30:
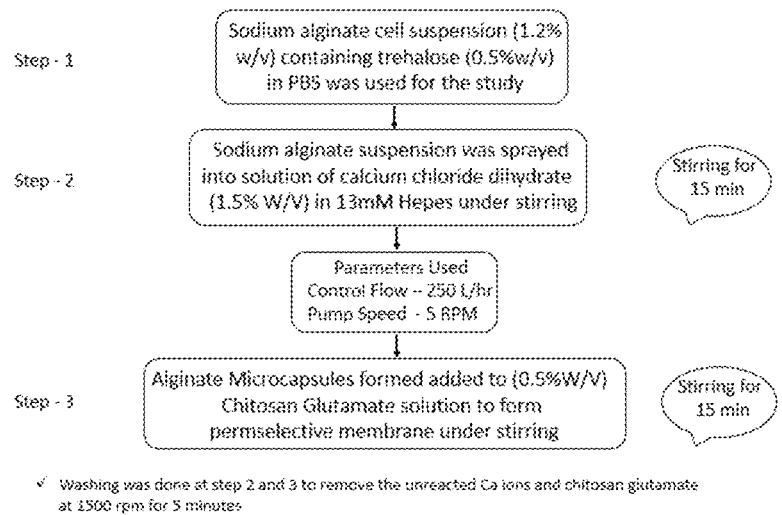
FIG. 30 is a schematic illustration of one exemplary method used for the preparation of microcapsules encapsulating live pancreatic beta cells using biocompatible polymer.

FIG. 30 shows a schematic method used for the preparation of microcapsules encapsulating live pancreatic beta cells using biocompatible polymer.

Figure 31:
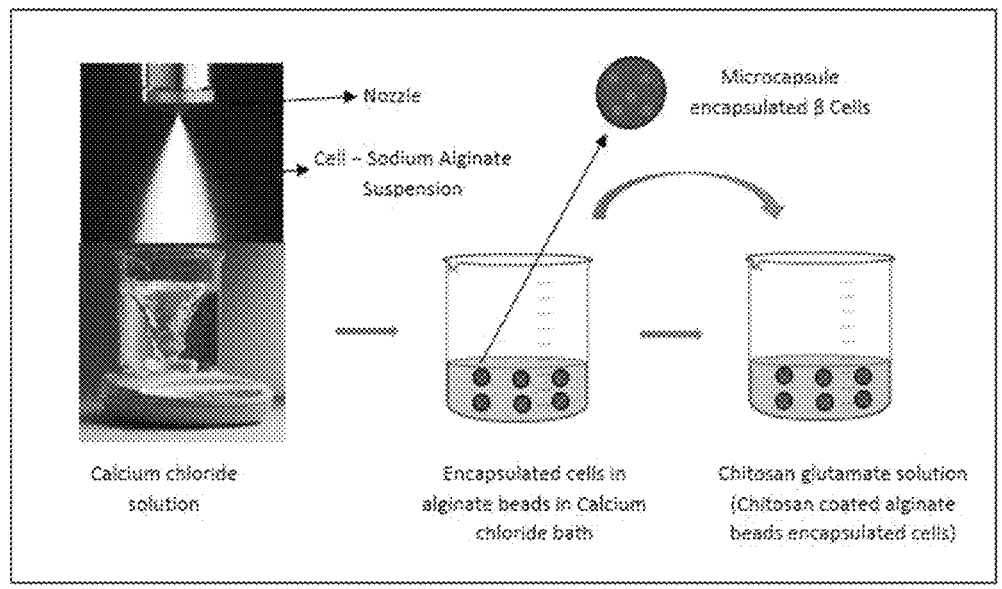
FIG. 31 is a diagrammatic representation of microcapsule preparation.

FIG. 31 is a diagrammatic representation of microcapsule preparation according to one exemplary embodiment.

Figure 32:
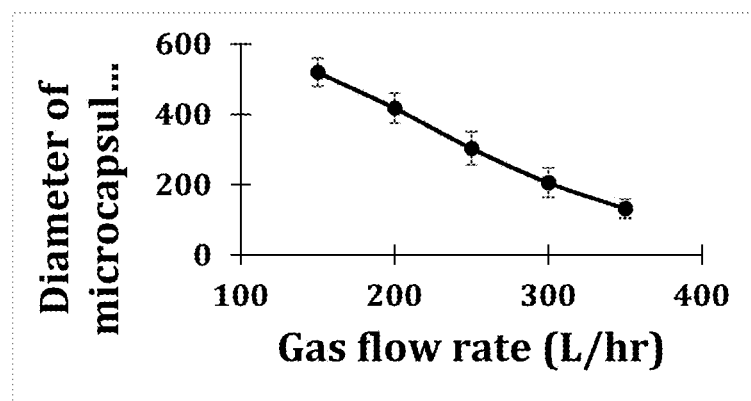
FIG. 32 shows the relation between gas flow rate and size of microcapsules.

FIG. 32 shows the relation between gas flow rate and size of microcapsules

Figure 33A:
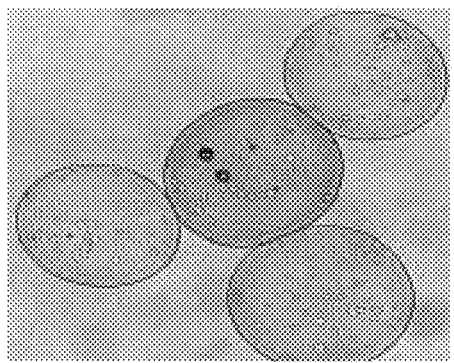
FIG. 33A is a first light microscopic image of microcapsules encapsulating pancreatic beta cells at 10×.
Figure 33B:
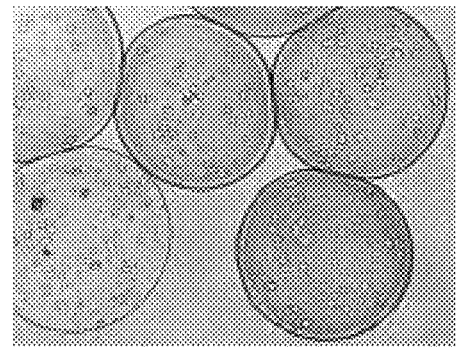
FIG. 33B is a second light microscopic image of microcapsules encapsulating pancreatic beta cells at 10×.

FIGS. 33A and 33B are light microscopic images of microcapsules encapsulating pancreatic beta cells at 10×.

Figure 34:
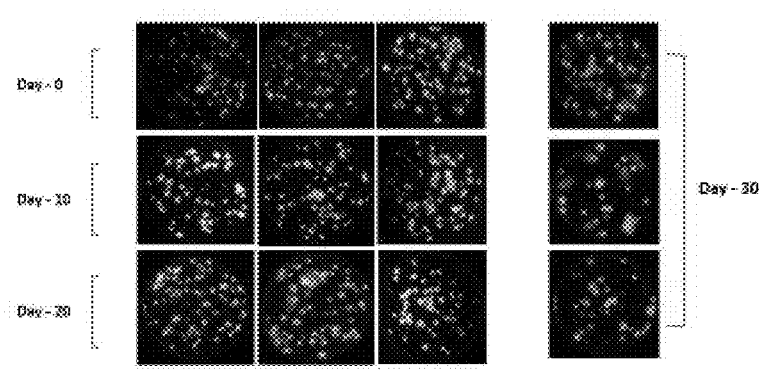
FIG. 34 shows fluorescent microscopic images of microcapsules encapsulating pancreatic beta cells at 10× showing live cells (green) and dead cells (red).

FIG. 34 shows fluorescent microscopic images of microcapsules encapsulating pancreatic beta cells at 10× showing live cells (green) and dead cells (red).

Figure 35:
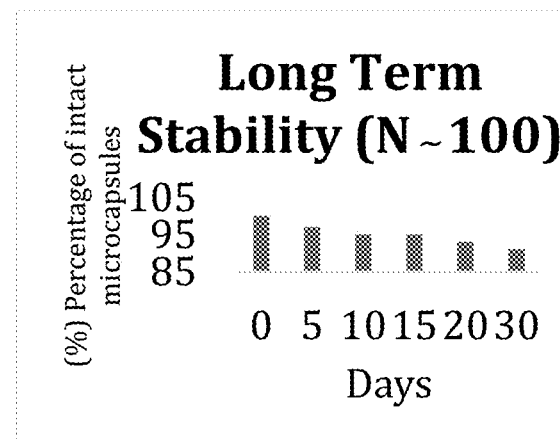
FIG. 35 shows stability of microcapsules in DMEM media at 37 degree Celsius carried out for 30 days.

FIG. 35 shows stability of microcapsules in DMEM media at 37 degree Celsius carried out for 30 days.

Figure 36:
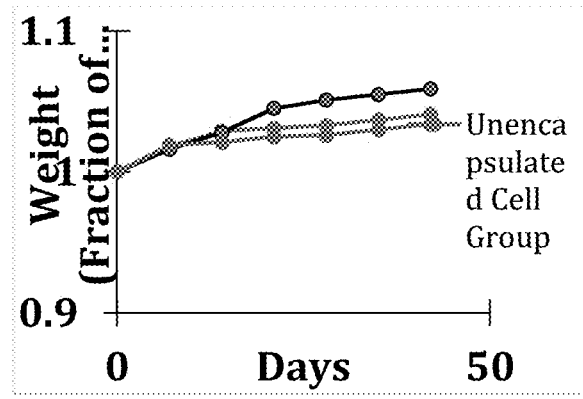
FIG. 36 shows the fractional weight of mice in different groups measured for 40 days.

FIG. 36 shows the fractional weight of mice in different groups measured for 40 days.

Figure 37:
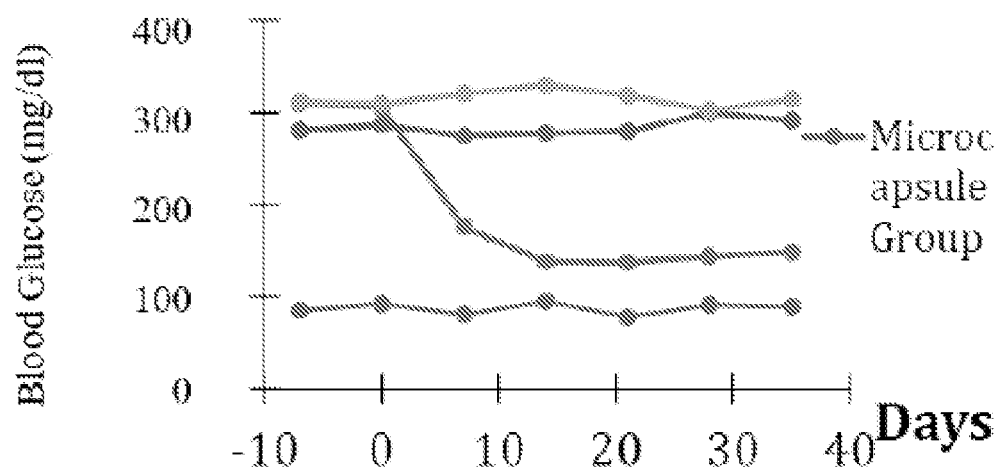
FIG. 37 shows blood glucose levels of different groups in mice measure for 35 days.

FIG. 37 shows blood glucose levels of different groups in mice measure for 35 days.

Figure 38:
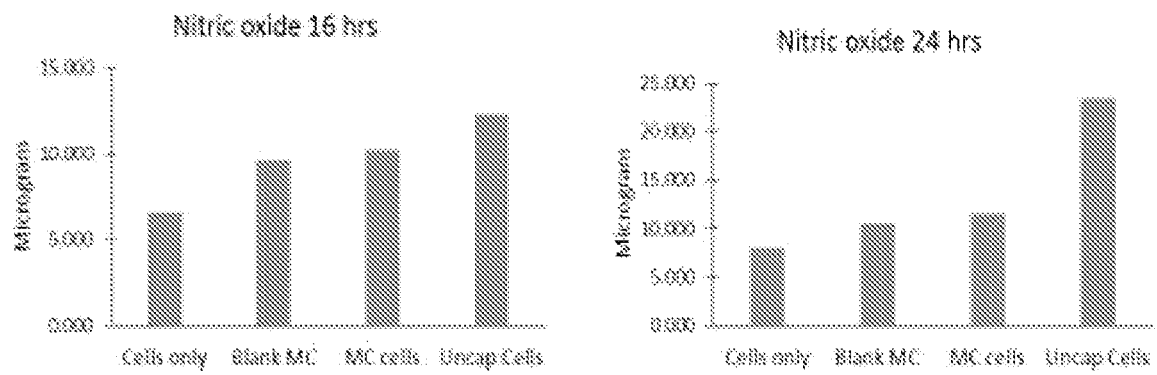
FIG. 38 shows nitric oxide levels of different groups in mice measure at 16 hrs and 24 hrs.

FIG. 38 shows nitric oxide levels of different groups in mice measure at 16 hrs and 24 hrs.

Figure 39:
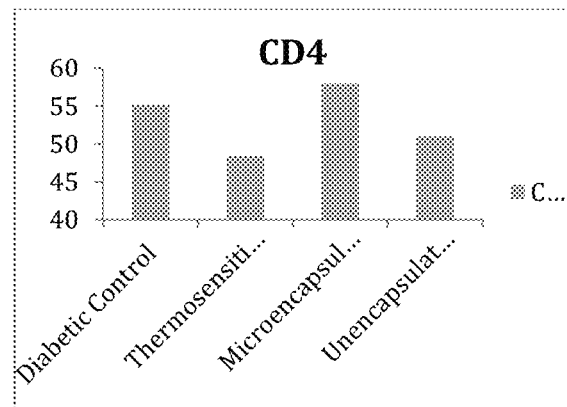
FIG. 39 shows a flow cytometric analysis showing CD4 cell counts in different groups of mice.

FIG. 39 shows a flow cytometric analysis showing CD4 cell counts in different groups of mice.

Figure 40:
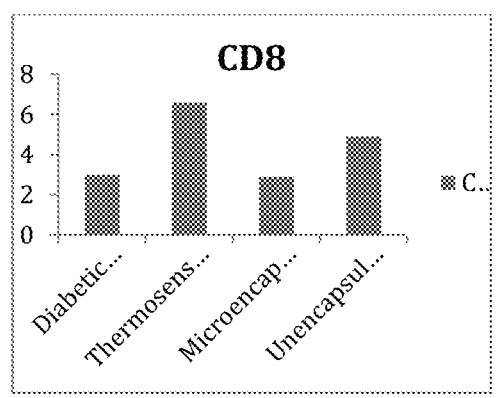
FIG. 40 shows a flow cytometric analysis showing CD8 cell counts in different groups of mice.

FIG. 40 shows a flow cytometric analysis showing CD8 cell counts in different groups of mice.

Example 7

Microneedle Delivery of Microencapsulated Vaccine and Bioactive Proteins and use of 3D Bioprinter for Microneedle Formation Described below are methods for printing microneedles containing microencapsulated vaccines, drugs, or other bioactive materials using an automated 3D printer.

Introduction

State-of-the-art Delivery of Particulate Vaccines via a Microneedle Patch

The skin provides a unique site for the vaccination purposes as it is easily accessible, has an ample blood supply, and houses various immune cells for an efficient immune response against a range of antigens. Skin serves as a barrier against various pathogens and is equipped with the skin associated lymphoid tissues (SALT) to combat any insult from invading pathogens. Various skin cells assist in generation of effective immune response. Keratinocytes are the most predominant (95%) epidermal cells in the skin. They can be activated by pathogens and result in production of cytokines, which in turn recruits dendritic cells/antigen-presenting cells to the site of action leading to initiation of the immune response. Skin hosts special kind of dendritic cells, the Langerhans cells. Langerhans cells comprise of only 2% of the total cell population in the epidermis but due to their extended dendrites spread in the epidermal layer they cover over 25% of the skin surface. These are professional phagocytic cells efficient in immune surveillance and further signaling to the T-cells present in their vicinity. Activated macrophages and T-cells drain into draining lymph nodes leading to an enhanced immune response.

Current conventional vaccines involve administering the vaccine using needles by intramuscular, intra dermal or subcutaneously by trained personnel. These have been highly effective in generating protective immunity, but are painful, require cold chain storage, and require a skilled professional for vaccination. Also, vaccination with hypodermic needle injections are associated with logistical disadvantages, such as, but not limited to, needle injuries and opportunistic infections, increasing the risk of hepatitis, HIV and other serious diseases that are transmitted by syringes and needles. Some side effects, including facial paralysis, were reported to be associated with intranasal influenza vaccination with an inactivated virosomal vaccine formulated bacterial toxin or even in the absence of adjuvant. In an attempt to overcome these limitations, we have explored the potential of delivering vaccine antigens into the skin using microneedles.

Microneedles are micron-sized needles, which when inserted into the skin, result in the formation of aqueous conduits that form a passage for the vaccine antigens to enter into the immune-competent layers of the skin. Due to their micron length (600 μm), contact with the nerve endings in the dermis is prevented and thus it offers a painless mode for immunization. Transdermal delivery using microneedles as proposed, is an attractive mode of immunization because of its ease of administration, and acceptability. Further, since the proposed vaccine exists in a dry powder, it is well protected from moisture. Thus, the shelf lives of these vaccines are expected to be significantly higher than the conventional vaccines, without preservatives and/or refrigerating storage systems. This is especially relevant in developing countries where the cold-chain cannot be easily maintained. Here, we propose improved vaccine formulations that stabilize vaccines with encapsulating biopolymers that can be administered much like a "Band-Aid patch".

Novel Particulate Vaccine Formulation

Figure 41:
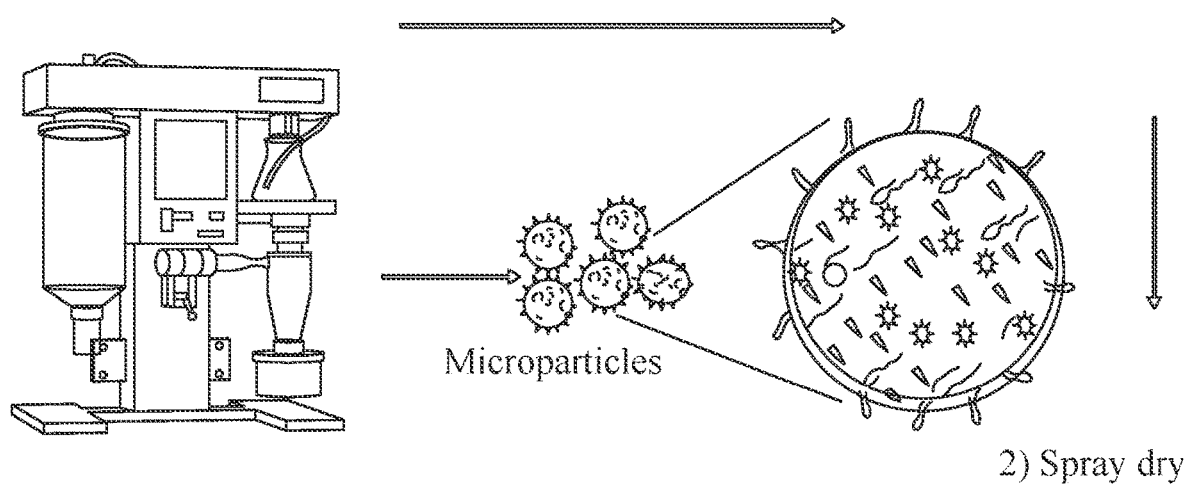
FIG. 41 shows the preparation of microparticulate vaccines using a spray dryer.

Encapsulating vaccines into nanoparticles and microparticles is attractive for presenting antigens to the immune system. The vaccine formulation in nanoparticles and microparticles will serve as a sustained release system. Here, we generate improved vaccine formulations that stabilize vaccines with encapsulating biopolymers, and target formulated vaccines to Langerhan cells in the skin. We have developed biodegradable and biocompatible polymer matrix systems for making particles loaded with vaccine antigens using the spray drying method. The process of encapsulation and formulation of the vaccine particles, is a one-step reproducible, aseptic & continuous process. The general vaccine formulation procedure involves the use of biodegradable, biocompatible, non-antigenic and sustained release polymer components containing cross-linked albumin matrix or poly lactic acid co glycolic acid, the vaccine antigen, and single or combination of adjuvants, that we have described in previously issued patents. The vaccine antigen in solution (spike S-1 protein) or the virus suspension is added to the biopolymer formulating solution. This vaccine polymer solution is sprayed through a Buchi Spray Dryer (Buchi Corporation) to form solid dry particulate vaccines (FIG. 41). Surface denaturation of albumin results in insoluble biodegradable microparticles when exposed to transient heat in the spray dryer.

Application of the Microneedle Patch and Novel Particulate Vaccine Formulation: Spike S-1 Protein or SARS CoV-2 Inactivated Virus Vaccine The novel corona virus 'SARS-CoV-2' (Severe Acute Respiratory Syndrome Coronavirus-2), is associated with the disease 'COVID-19'. On the $11^{th}$ of March 2020, COVID-19 was declared as a 'Pandemic'. The virus poses a serious public health risk. Currently, there are no approved vaccines or reliable treatments for COVID-19. This has led to a dire need for treatment measures and vaccine development. The SARS-CoV-2 belongs to the subclass of beta coronaviruses that consist of four proteins—Spike Protein (S), Envelope Protein (E), Membrane Protein (M), and Nucleocapsid Protein (N).

We have been developing a microparticulate vaccine containing the spike S-1 proteins from the SARS-CoV-2 virus and also a heat inactivated SARS CoV-2 virus along with adjuvants. In our quest to advance to the next generation of vaccines, we propose to formulate and deliver these vaccine microparticles via a microneedle delivery system, to be applied much like a "band-aid" like patch. More importantly, we have now developed novel encapsulating formulations that produce microsphere particles containing vaccine antigens, which significantly stabilize susceptible antigens with biodegradable materials and can target these vaccines to the skin associated lymphatic tissue (SALT).

The Spike protein is a large type 1 transmembrane protein which assembles itself in a trimeric structure to form a crown like appearance. The ectodomain of the spike protein of all coronaviruses are similar in organization, containing a N terminal (amino acid terminal) subunit (S-1) and a C terminal (carboxy terminal) subunit (S-2). The subunit S-1 infects human respiratory epithelial cell through interaction with human ACE 2 receptor and the S-2 subunit fuses with the host cell membrane. The spike S-1 protein has been established as a key target for potential vaccine development as it has been determined to be highly immunogenic and thus will be evaluated as one of the potential vaccine candidates in our studies. We will also examine the potential of intact heat inactivated virus as a vaccine candidate. By using the entire virus as the antigen, we preserve and present all the possible antigenic proteins and their immunogenic epitopes in their native form to antigen presenting cells (APCs), and could help in inducing a robust immune response.

Furthermore, we use a sustained release micro particulate-based delivery systems, which is believed to interact distinctively with the immune system by slowly releasing antigens, which has shown significant enhancement in immune activation.

The micro-particulate nature of the vaccine described herein allows for better antigen uptake by APCs, due to their universal receptor-mediated endocytosis, leading to improved antigen presentation and subsequent activation of T cells. The Langerhans cells (LCs) in the epidermis and the dermal dendritic cells in the dermis, which form part of the skin associated lymphatic system (SALT), can activate T and B lymphocytes. Therefore, this is an excellent route of delivery for vaccines as shown by previous studies conducted in our laboratory. The COVID-19 vaccine formulation described herein consists of heat inactivated SARS-CoV-2 virus and the spike S-1 protein, in separate vaccine formulations, encapsulated in an albumin-based particulate system that mimics the chemical conjugation process to a protein carrier, enhancing antigen uptake via albumin receptors, and eliciting a T-cell-dependent immune response and also poly lactic co-glycolic acid polymers.

As described herein, the novel vaccine is encapsulated with SARS Spike S-1 protein or the heat inactivated SARS-CoV-2 virus or other bioactive drugs or compounds. It is incorporated into an albumin-based particulate matrix or combined with poly(lactic-acid-co-glycolic-acid) or biopolymers that can be crosslinked using the UV light in a 3-D bioprinter. Such vaccine may provide one or more of the following advantages:

1—A whole-virus based vaccine that encompasses all immunogenic epitopes;
2—Highly antigenic Spike subunit S-1 protein;
3—Self-adjuvanting vaccine formulations that enhance immunogenicity using adjuvants that are TLR ligands such as Alum, MF59, MPL-A, Resiquimod, Imiquimod, CpG;
4—Improved uptake by immune cells and slow antigen release, i.e., an "intracellular antigen depot effect" that can result in prolonged cross-presentation in the lymph nodes and spleen, which is important for T-cell stimulation;
5—Induction of robust autophagy formation that enhances antigen presentation; and
6—A heat-stable formulation that does not require cold chain conditions.

As described herein, the microneedles contain a microparticulate vaccine or bioactive drug and are printed from biopolymers using a 3-D Bioprinter, followed by drying in a vacuum desiccator. The microneedles and microneedle patches described herein may provide one or more of the following advantages:

1—The microneedles do not need to maintained in cold chain conditions;
2—Administration of the microparticulate vaccine or bioactive drug by a microneedle skin patch is non-invasive and pain-free; and
4—Reduced cost with the elimination of expenditures relating to identification of a single immunogenic antigen/epitope (for the virus), and individual packaging and refrigeration of ampoules.

Summary of Methods

Determination of the optimal formulation of antigen encapsulation into microparticles for further loading into biodegradable microneedles and characterization:

We developed novel particulate of containing the a) SARS-CoV-2 Spike protein as the antigen and b) heat inactivated SARS-CoV-2 virus. These vaccine antigens, along with adjuvants such as Alum; MF-59, MPL-A, Resiquimod, Imiquimod, CpG, or their combinations were encapsulated into biodegradable polymer matrices. The stability and release properties of the encapsulated vaccine antigens was determined. Characterization studies such as vaccine microparticle size, charge, encapsulation efficiency, release of the antigen and stability studies were carried out.

Assessment of antigen presentation in antigen presenting cells (APCs) pulsed with vaccine particles enhanced with adjuvants for determination of co-stimulatory molecule expression and T cell proliferation:

We evaluated antigen presentation in APCs (dendritic cells) in vitro and on inducing spike protein or virus specific systemic and mucosal immune responses of humoral and cellular immunity after transdermal microneedle vaccination. Specifically, we determined the MHC-I/CD 80 and MHC-II/CD 40 expression.

Determination the antibody titers in mice and the correlates of protection in mice of the SARS-CoV-2 virus or spike S-1 protein vaccine formulations loaded into a microneedle skin patch:

Measurement of the induction of antibody titers, antigen-specific CD4/CD8 T cells, and long-term memory responses in vaccinated mice:

Using a mouse model, we screened the efficacy of theses formulations on inducing a robust antibody response after vaccination. We evaluated the formulations of Corona virus (Spike S-1 protein antigen and Corona virus SARS-CoV-2 heat inactivated virus) by evaluating the breadth of antibodies to the Virus and Spike protein antigen, and the breadth of neutralizing titers.

Materials, Methods, and Results
Microencapsulated Vaccines

Figure 42A:
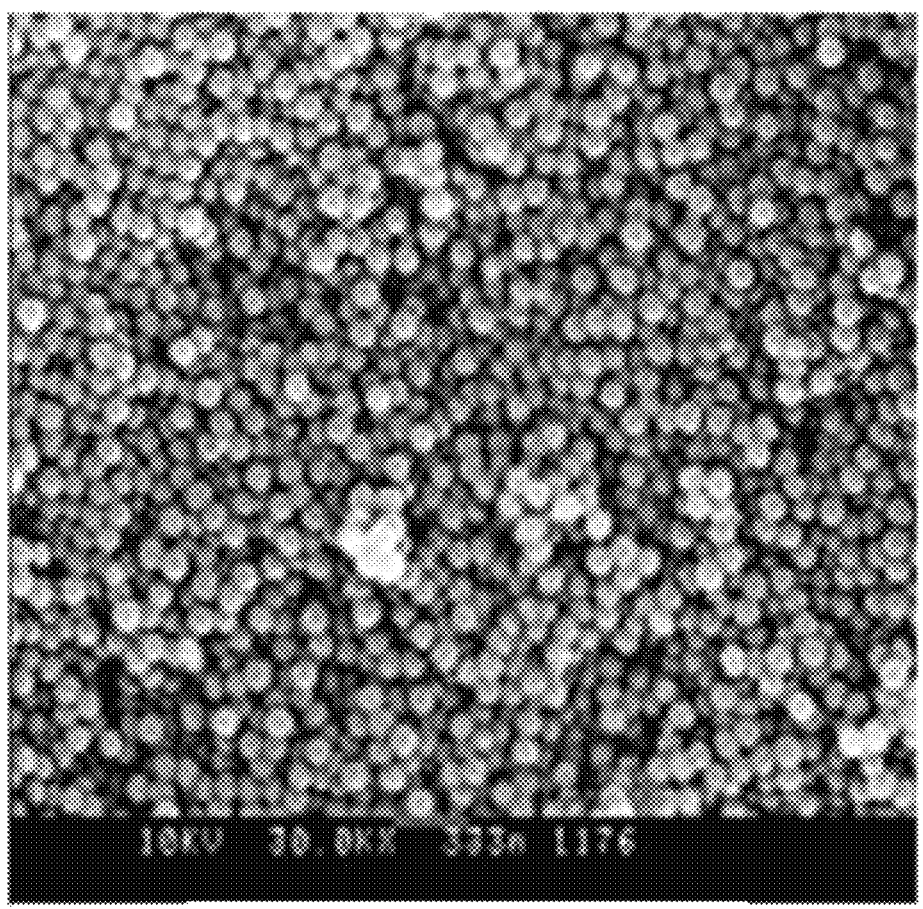
FIG. 42A is a SEM image of spray dried particles containing the Spike S-1 vaccine antigen.

We prepared preliminary batches of intact heat inactivated SARS-CoV-2 virus (ATCC, VA), and Spike S-1 protein, (Genscript, NJ), encapsulated into biodegradable particles using the Buchi Mini Spray Dryer. Briefly, mouse albumin (for human vaccines, recombinant human albumin will be used) was pre-cross-linked for 1 hour with glutaraldehyde and the excess glutaraldehyde was then neutralized with sodium bi-sulfite. The vaccine antigen (2.5%) and adjuvants (Alum, MF-59, MPL-A, or their combinations, 2.5%) were then added just before spray drying. The dry particles were characterized for their surface morphology, size, toxicity, charge and yield. Scanning electron microscopy (SEM) was performed to evaluate the surface morphology of the particles. FIG. 42A is a SEM image of the spray dried particles containing the Spike S-1 vaccine antigen. The average size of the particles ranged from 1.25 µm±0.6 µm. The average percent yield was 92.5% and the encapsulation efficiency, was 89.2% after spray drying. The surface charge was found to be 8.2 mV±1.2 mV (Malvern Zeta Sizer, UK).

Figure 42B:
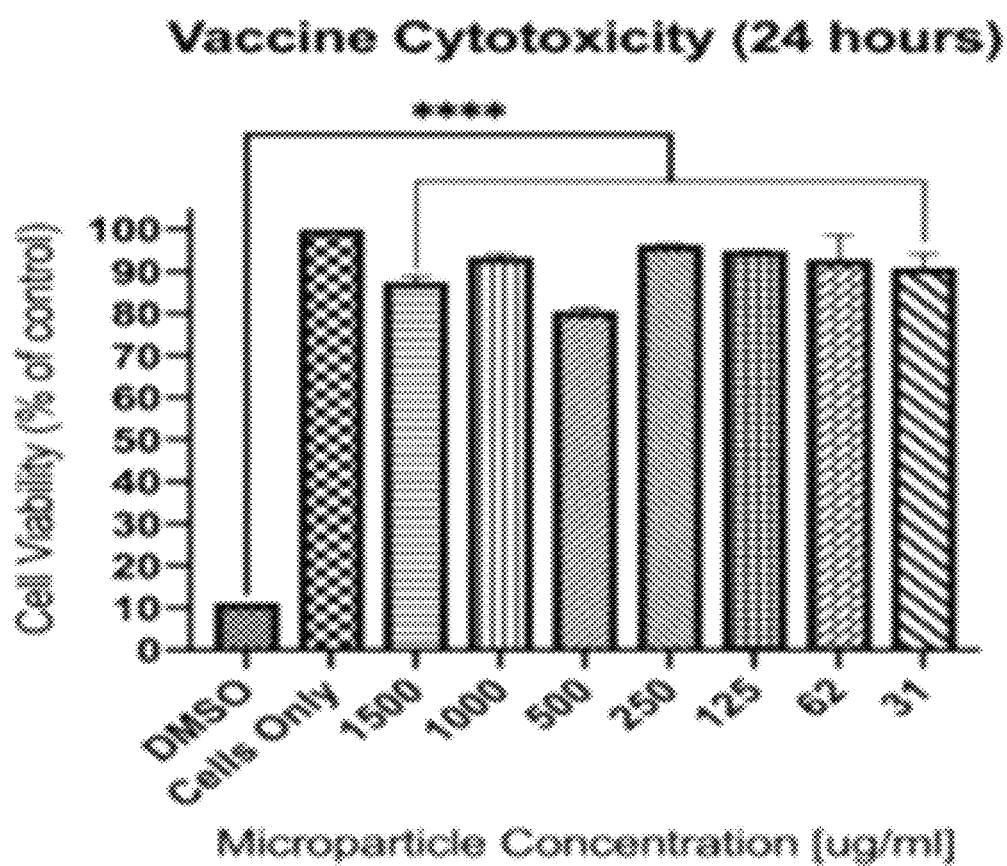
FIG. 42B shows vaccine particle cytotoxicity to dendritic cells across different microparticle concentrations at 24 hrs.

The vaccine particles were tested for toxicity by exposing them to dendritic cells (DC) in culture: all studies demonstrated greater than 95% cell viability (N=6 batches). FIG. 42B shows the vaccine particle cytotoxicity to dendritic cells across different microparticle concentrations at 24 hrs. Our studies in non-human primates of blank microparticles with similar biodegradable matrices in the past, demonstrated no in-vivo liver or kidney toxicity as demonstrated by serum creatinine, BUN, and SGOT levels.

Figure 42C:
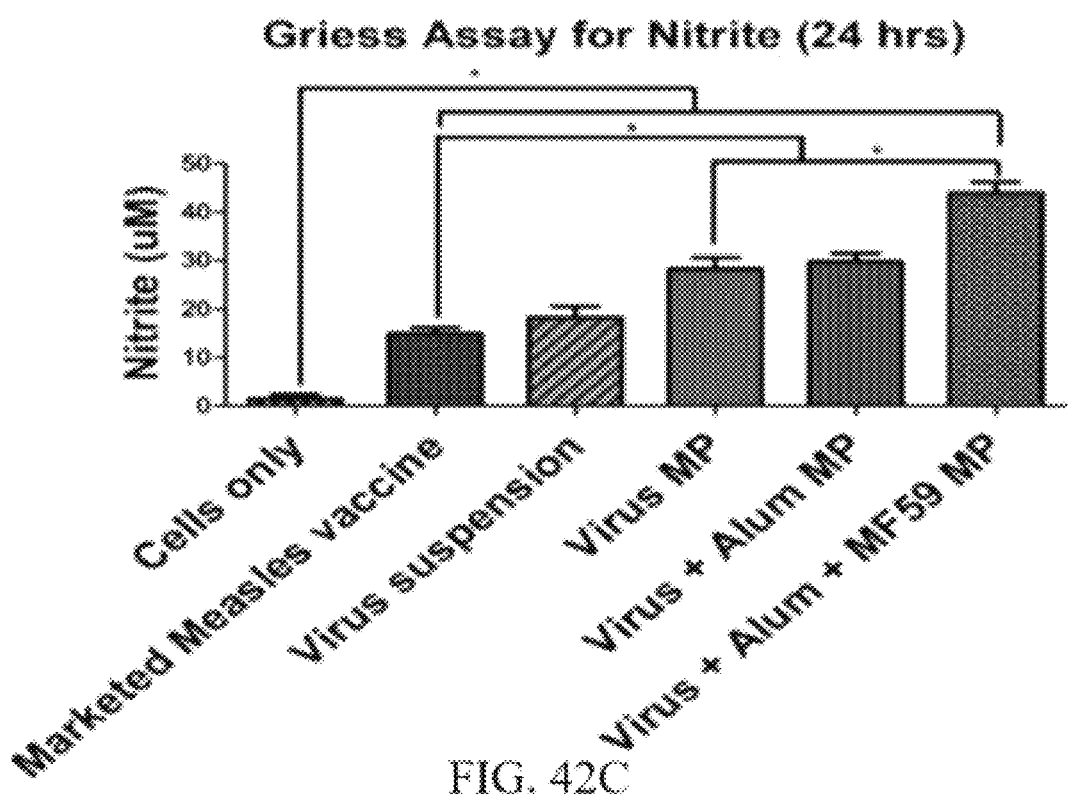
FIG. 42C shows enhanced nitrite release by dendritic cells at 24 hrs after exposure of the Spike S-1 protein particles or SARS-CoV-2 virus.

The enhanced nitrite release after exposure of the Spike S-1 particulate vaccines (with adjuvants such as Alum or MF59) to dendritic cells, was determined to be significantly higher than nitrite release associated with a marketed measles vaccine at equivalent doses. FIG. 42C shows this enhanced nitrite release by dendritic cells at 24 hrs after exposure of the Spike S-1 protein particles or SARS-CoV-2 virus, demonstrating strong innate immunogenicity ($*p<0.05$).

Figure 42D:
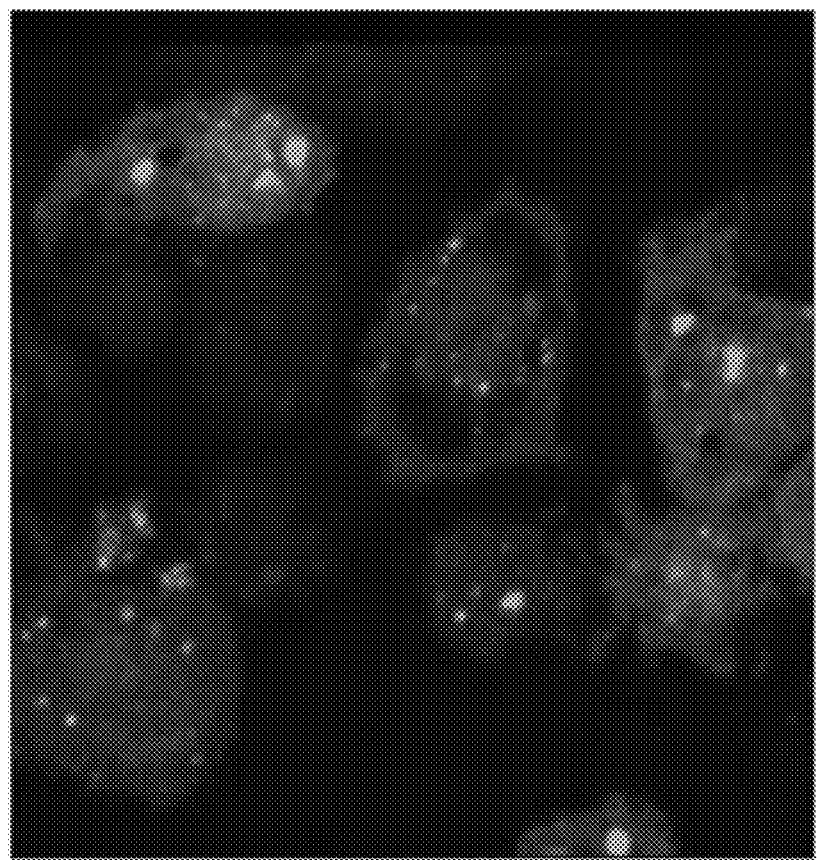
FIG. 42D is a fluorescent microscopic image showing that SARS-CoV-2 virus vaccine particle uptake by macrophages induced autophagic vacuoles.

FIG. 42D is a fluorescent microscopic image showing that SARS-CoV-2 virus vaccine particle uptake by macrophages induced autophagic vacuoles. That is, the uptake of spike S-1 vaccine particles or SAS-CoV-2 virus particulate vaccines to macrophages resulted in autophagic vacuoles as visualized using fluorescence microscopy, but empty particles did not, indicating biological activity. Further, as a measure of innate immune responses, levels of cytokines such as TNF-alpha, IL-1 beta and IFN-gamma levels were higher in DC exposed to vaccine particles, demonstrating significantly higher immunogenicity when compared to non-encapsulated vaccine virus or spike S-1 proteins or controls.

Figure 43A:
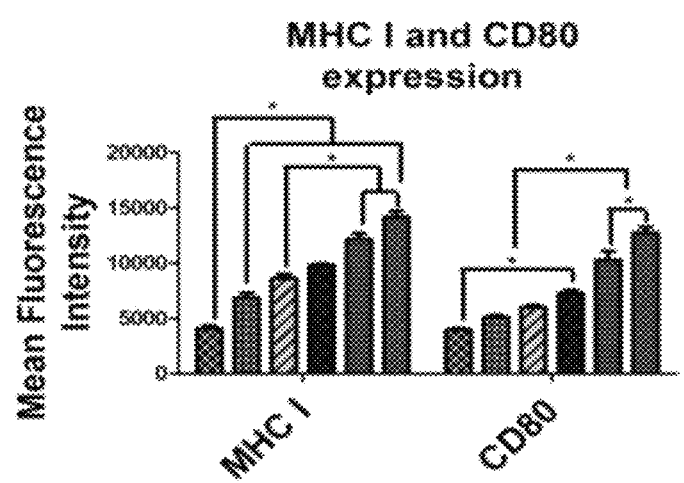
FIG. 43A shows MHC I and CD80 expression on dendritic cells post exposure to Spike S-1 protein vaccine.
Figure 43B:
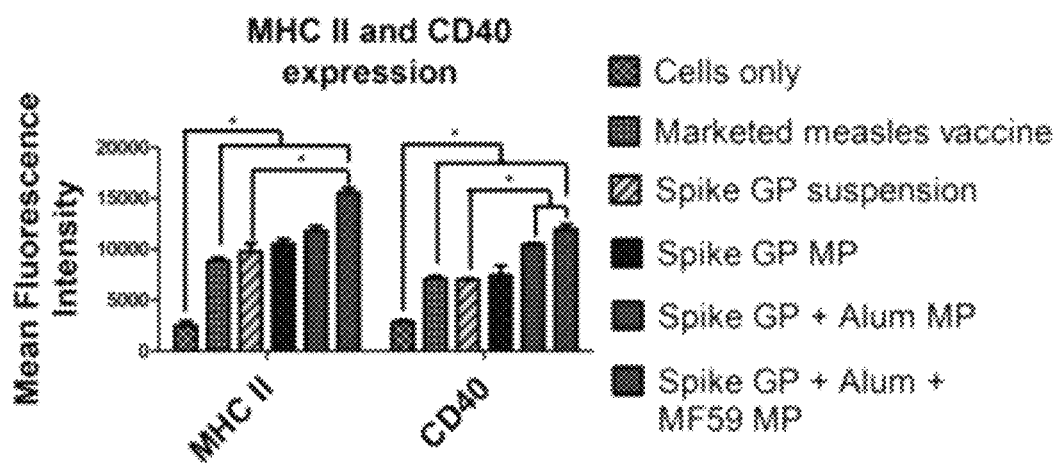
FIG. 43B shows MHC II and CD40 expression on dendritic cells post exposure to Spike S-1 protein vaccine.
Figure 43C:
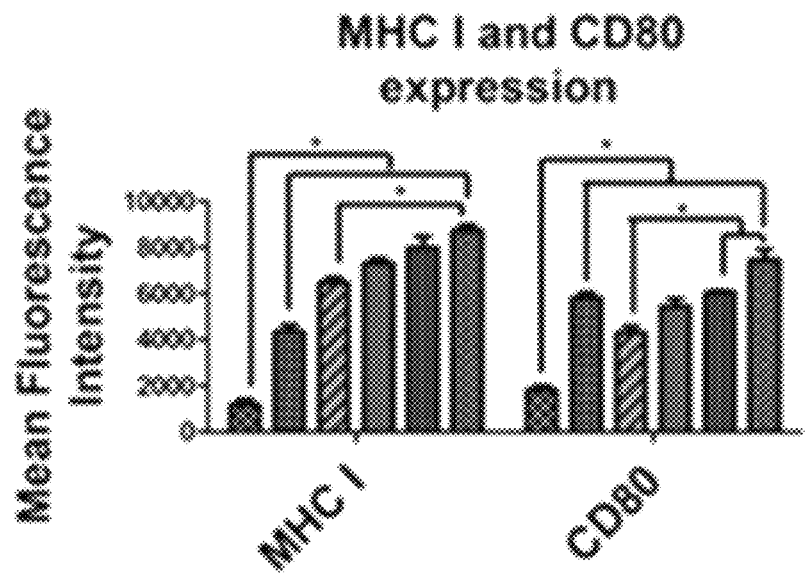
FIG. 43C shows MHC I and CD80 expression on dendritic cells post exposure to SARS-CoV-2 virus.
Figure 43D:
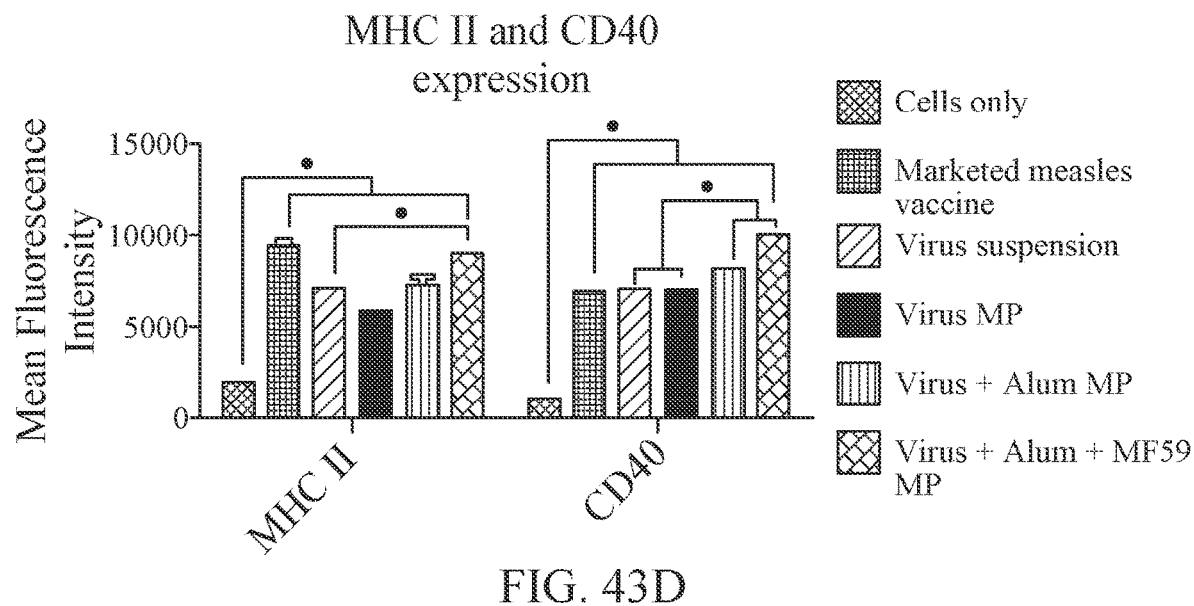
FIG. 43D shows MHC II and CD40 expression on dendritic cells post exposure to SARS-CoV-2 virus.

Both the encapsulated vaccines (heat inactivated virus and spike S-1 protein) enhanced both MHC-I and MHC-II and their corresponding CD-80 and CD-40 co stimulatory molecules in studies carried out using dendritic cells (DC2.4) as determined by FACS analysis and shown in FIGS. 43A-43D. Interestingly, the MHC-I and MHC-II and their corresponding CD-80 and CD-40 co stimulatory molecules were also significantly higher than equivalent does of the marketed measles vaccine (p<0.01) with Spike S-1 protein vaccine. FIG. 43A shows MHC I and CD80 expression on dendritic cells post exposure to by Spike S-1 protein vaccine while FIG. 43B shows MHC II and CD40 expression on dendritic cells post exposure to Spike S-1 protein vaccine. FIG. 43C shows MHC I and CD80 expression on dendritic cells post exposure to SARS-CoV-2 virus while FIG. 43D shows MHC II and CD40 expression on dendritic cells post exposure to SARS-CoV-2 virus. The adjuvanted particulate vaccines in most cases resulted in significantly higher responses than non-encapsulated vaccine particles.

Formulation of Microneedles Containing the Microencapsulated Vaccines

Formulation of microneedles containing a micro particulate vaccine or bioactive drug, using a 3-D Bioprinter (CELLINK INKREDIBLE plus 3D printer) using UV crosslinking biopolymers in situ (crosslinking reaction of poly(ethylene glycol)diacrylate (PEGDA) under UV light—an automated and reproducible process. By taking advantage of the in-built UV lamp within the 3D printer, we were successful in crosslinking the microneedle using the UV in as little as 45 seconds, with no degradation to the protein and thus the formulation of the microneedle from start to end could be accomplished completely automatically within a timeframe of 3-5 minutes for each batch of 24 microneedle patches. The in-built design of the laminar flow air system within the 3D printer was taken advantage of to formulate the ODF films aseptically.

A solution was first made of polyvinylpyrrolidone (i.e., KOLLIDON™ 90F, KOLLIDON™ VA64), PEG2000 using Absolute ethanol in a beaker. This constituted the film composition. To this was added the drug or vaccines in a nano or microparticulate suspension (solutions of the drugs or vaccine material can also be used alternatively). This suspension/solution was then added to one of the dispensers in the CELLINK INCREDIBLE Plus 3D printer (Cellink, Sweden). The 3D printer was then programmed to dispense into a 24-well format to conform to the 24-format mold to hold the microneedle molds. In this example we used the COVD-19 Spike S-1 protein as the vaccine antigen that was encapsulated into polylactic co-glycolic acid nanoparticles. We used the commercially available CELLINK INKREDIBLE plus 3D printer for the formulation of the film. This 3D printer has 2 different intensities of UV light: 365 nm and 405 nm; and a HEPA filter for sterile manufacturing. After the film was dispensed, the polymers were cured or crosslinked using the in-built UV lamp in the 3D printer at 405 nm UV wavelength for 45 seconds. Poly(ethylene glycol) diacrylate (PEGDA) is a pre-polymer solution that can be used in the formation of a cross-linked polymeric system as it readily crosslinks under UV light in presence of free radicals. We thus used PEGDA as the crosslinking polymer in the film formulation using the 3D printing technique. This allowed for very quick curing of the polymers to form the film using the 3D printing technique to completely automate the process. Variations of the microneedle formulation with 5 different components, as illustrated in Table 8, were also tested. The lead formulation of ODF is shown in Table 9.

TABLE 8

| Formulation | Component 1 | Component 2 | Component 3 | Component 4 | Component 5 |
| --- | --- | --- | --- | --- | --- |
| Formulation 1 | KOLLIDON 90F 138 mg KOLLIDON VA64 9 mg PEG2000 5 mg Absolute ethanol 850 microliters | PEGDA | Lactose DI water | Diphenyl phosphine oxide (photo-initiator) | Tween 20 (surfactant) |
| Formulation 2 | KOLLIDON 90F KOLLIDON VA64 PEG2000 Absolute ethanol | PEGDA | Gelatin DI water | Diphenyl phosphine oxide (photo-initiator) | Tween 20 (surfactant) |
| Formulation 3 | KOLLIDON 90F KOLLIDON VA64 PEG2000 Absolute ethanol | PEGDA | Sodium bicarbonate DI water | Diphenyl phosphine oxide (photo-initiator) | Tween 20 (surfactant) |
| Formulation 4 | KOLLIDON 90F KOLLIDON VA64 PEG2000 Absolute ethanol | PEGDA | Trehalose DI water | Diphenyl phosphine oxide (photo-initiator) | Tween 20 (surfactant) |
| Formulation 5 | KOLLIDON 90F KOLLIDON VA64 PEG2000 Absolute ethanol | PEGDA | Sucrose DI water | Diphenyl phosphine oxide (photo-initiator) | Tween 20 (surfactant) |
| Formulation 6 | KOLLIDON 90F KOLLIDON VA64 PEG2000 Absolute ethanol | PEGDA | Sucrose Chitosan glutamate DI water | Diphenyl phosphine oxide (photo-initiator) | Tween 20 (surfactant) |

The lead formulation of ODF is shown in Table 9 below:

TABLE 9

| Component 1 | Component 2 | Component 3 | Component 4 |
|---|---|---|---|
| KOLLIDON 90F 16.24% w/v | PEGDA Mn 575 | Chitosan glutamate 1.5% w/v | Diphenyl phosphine oxide 0.02% w/v |
| KOLLIDON VA64 1.06% PEG2000 0.6% w/v | | Sucrose 40% w/v Deionized water | Tween 20 |
| Absolute ethanol | | | |

Figure 44A:
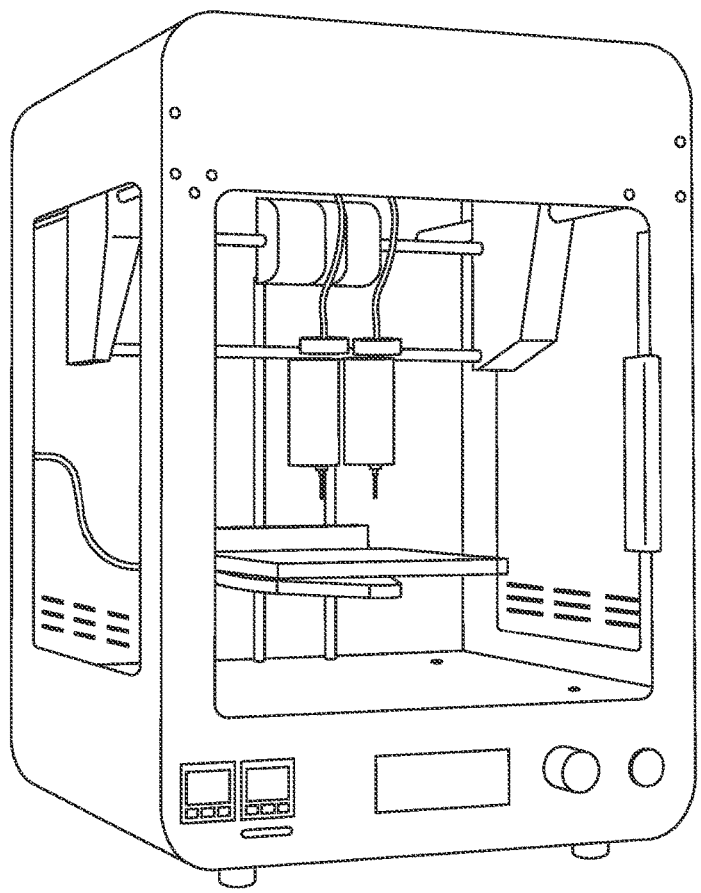
FIG. 44A shows an example 3D Bioprinter (CellInk Inkcredible Plus™) usable with the methods and systems described herein.
Figure 44B:
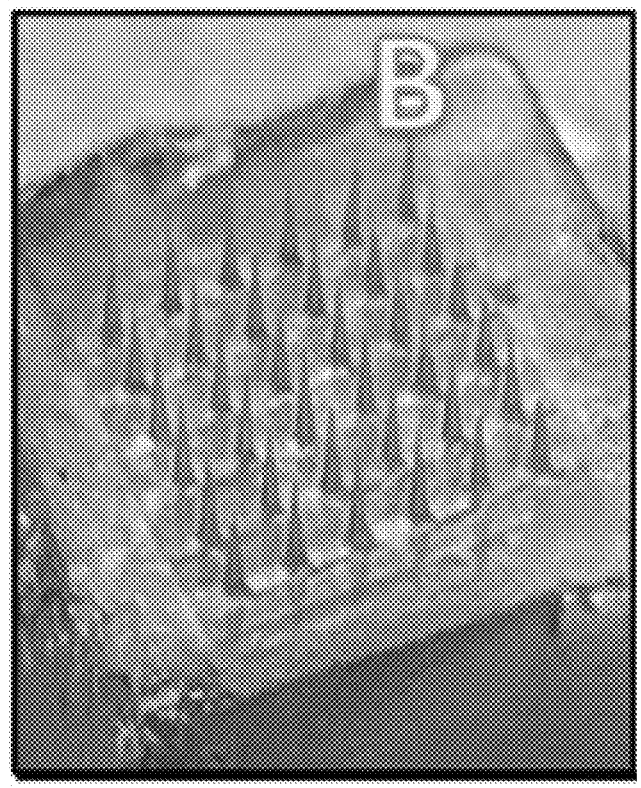
FIG. 44B shows an example microneedle array in accordance with the methods and systems described herein.
Figure 44C:
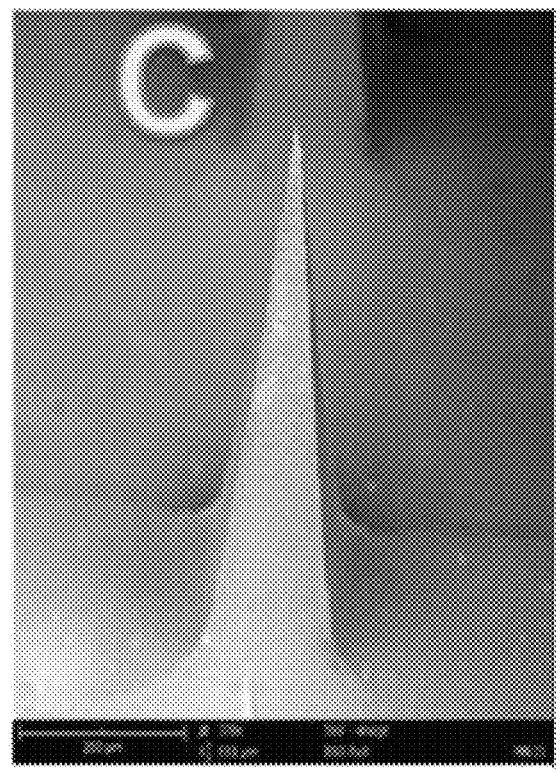
FIG. 44C shows a single microneedle of the microneedle array of FIG. 44B.

In another example, dissolvable microneedles encompass the use of polydimethylsiloxane (PDMS) micro molds, (Micropoint Technologies, Singapore). In one example, particulate vaccine microneedles were made using the following formula: vaccine particles (2% w/w-0.5 mg); maltose (25% w/w); hyaluronic acid (HA, 73% w/w). The calculated quantities were used for making 2 microneedle patches. First, maltose and HA were added to a 1.7 mL microcentrifuge tube containing 550 μl of water and vortexed. The weighed amount of SARS-CoV-2 vaccine particles (0.5 mg, using either the virus or the spike S-1 protein) was then added into the mixture. The molds were then placed in a 12 well plate into the 3D Bioprinter (Cellink Inkredible Plus, Sweden), shown in FIG. 44A. Approximately 250 μl of the formulation was added to the microneedle molds using the automated 3D Bioprinter and allowed to dry in a vacuum desiccator at room temperature for 4 hours. After drying, 200 μl of a backing layer composed of the same polymer matrix, but without the vaccine antigen was added to the molds, again using the 3D Bioprinter, and dried as before for 4 hours. The microneedle patch measured 1×1 cm in size comprising of an array of 64 microneedles (8×8). The microneedles were 600 μm in length FIG. 44B shows the microneedle array. The microneedle array (8×8) was then placed on a 2×2 cm adhesive patch much like a "band-aid" patch, ready for application to the skin. Scanning electron microscopy was carried out to observe the surface morphology and formation of microneedles. FIG. 44C shows a single microneedle of the microneedle array.

Figure 44D:
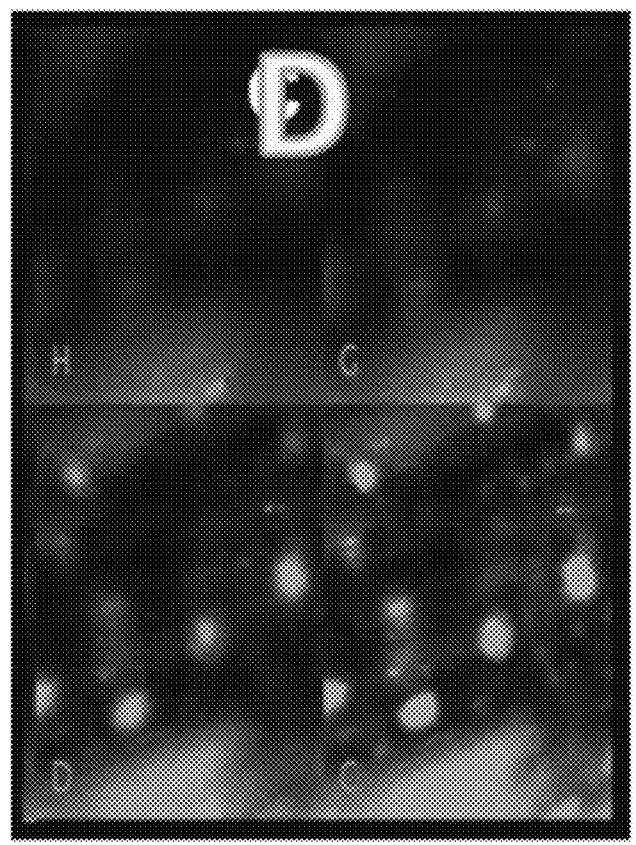
FIG. 44D shows a confocal microscopic image of a Z-stack of Calcein-stained microchannels as seen on mouse skin, with Calcein observed in microchannels to up to 600±60 μm depth.
Figure 44E:
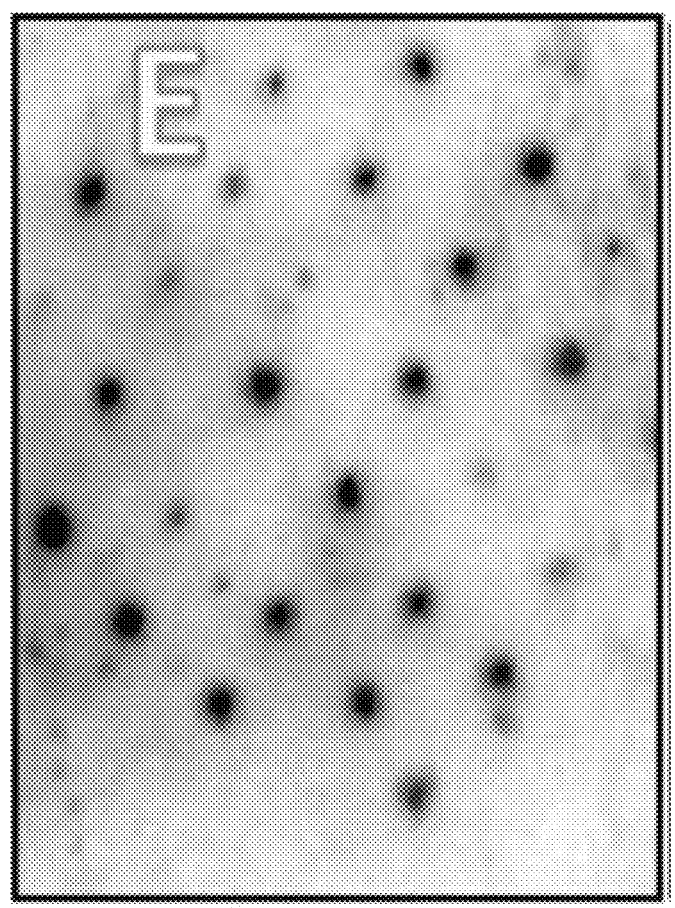
FIG. 44E shows microchannels (using methylene blue dye) created by the microneedles patch of FIG. 44B on the mouse skin of FIG. 44D.
Figure 44F:
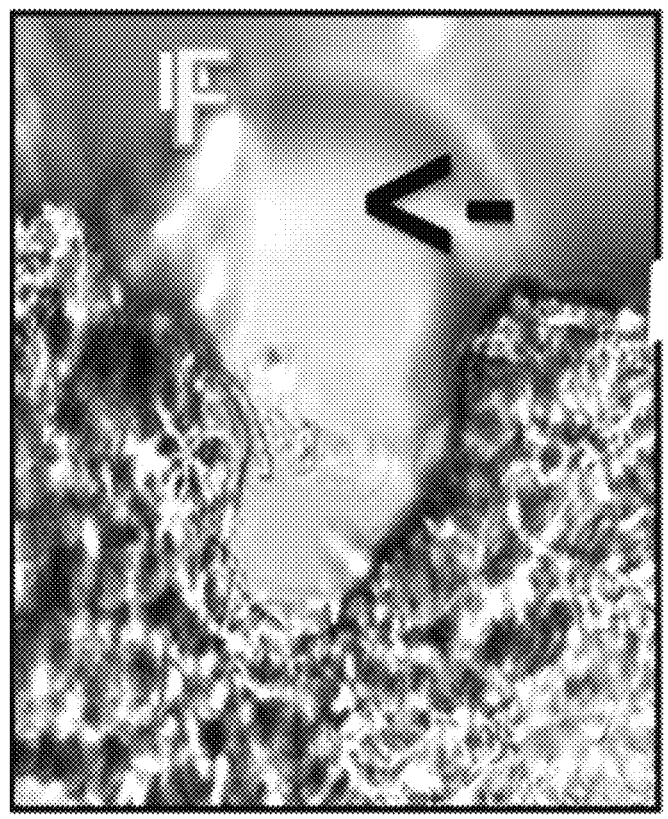
FIG. 44F shows a light microscopic image of transverse skin sections of microchannels (stained with methylene blue dye, 10× magnification).

For transdermal vaccination, it was important to visualize the microchannels in-order to understand their depth within the skin layers. In order to visualize the microchannels, they were stained with Calcein dye (FluoSpheres® 0.2 μm) and observed by confocal microscope (FIG. 44D, a confocal microscopic image of a Z-stack of Calcein-stained microchannels as seen on mouse skin, with Calcein observed in microchannels to up to 600±60 μm depth) or with methylene blue and observed by light microscope (FIG. 44E, showing created by the microneedles patch of FIG. 44B on the mouse skin of FIG. 44C). For methylene blue staining, full thickness murine skin was freshly excised from the animal and treated with microneedle patch. Skin samples were embedded in OCT medium in embedding molds, frozen at −80° C. and cryo-microtomed transversally (Thermo Scientific, IL) with a thickness of 50 μm. For confocal microscopy, full thickness skin was freshly excised and treated with microneedles. The channels were then stained with FluoSpheres® 0.2 μm for 2 minutes. Full thickness skin sections were mounted on microscope slides and viewed under a Zeiss LSM510 confocal microscope with 10× air objective. An argon laser of 488 nm wavelength was used to excite the fluorophore and a band pass filter of 500-550 nm was used (FIG. 4D). Image J software from NIH, was used to analyze the images. FIG. 44F shows a light microscopic image of a transverse skin section of microchannel (<-) created by a microneedle (stained with methylene blue dye, 10× magnification).

Figure 45A:
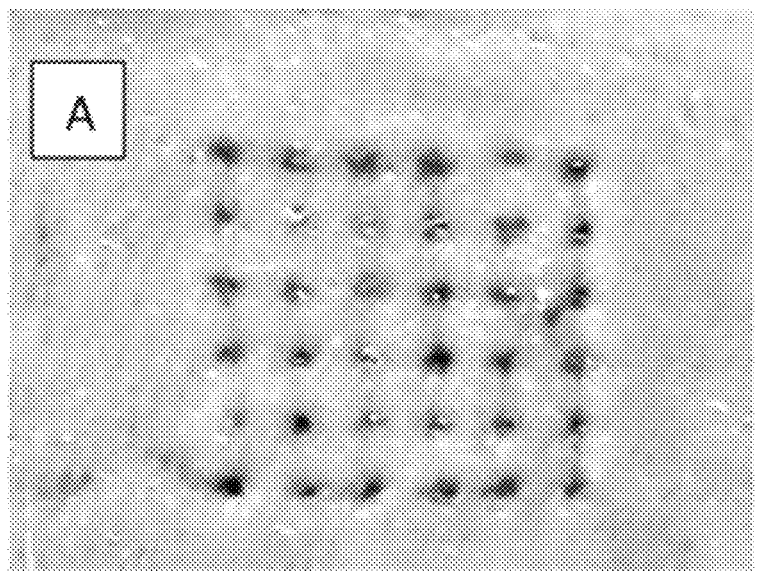
FIG. 45A shows skin immediately after application of a microneedle patch.
Figure 45B:
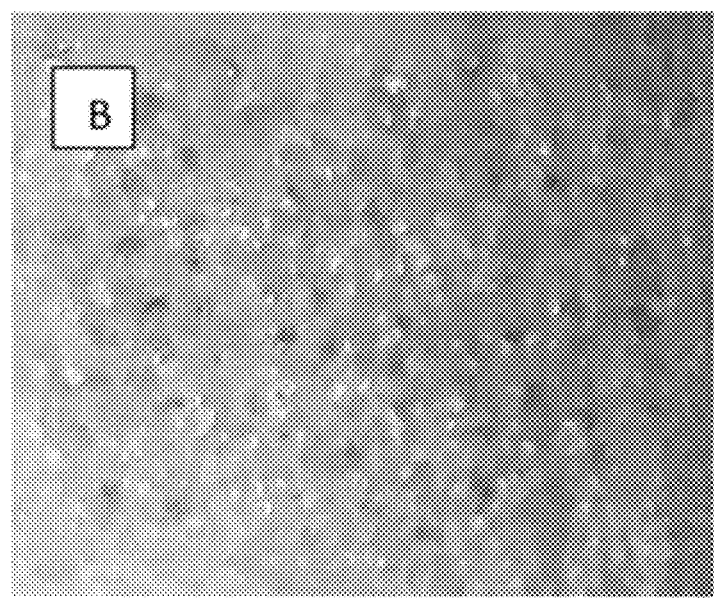
FIG. 45B shows an image taken 30 minutes after the image of FIG. 45A, showing closure of the pores on the skin.
Figure 45C:
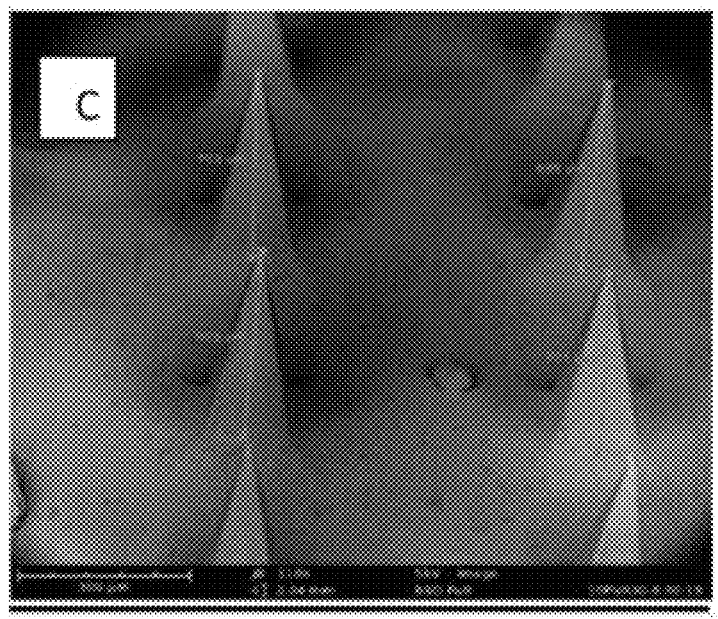
FIG. 45C shows a scanning electron microscopic (SEM) of a vaccine microneedle array (Spike S-1 protein).
Figure 45D:
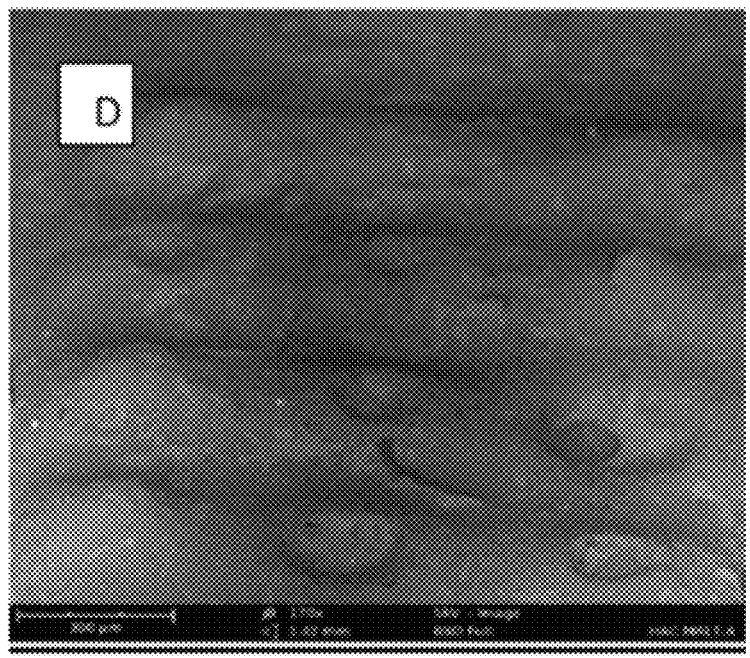
FIG. 45D shows a SEM image of the array of microneedles of FIG. 45C taken after application of the vaccine microneedle patch on the skin of a mouse for 5 minutes, showing that the microneedles were dissolved completely delivering the vaccine particles into the skin.
Figures 45E, 45F:
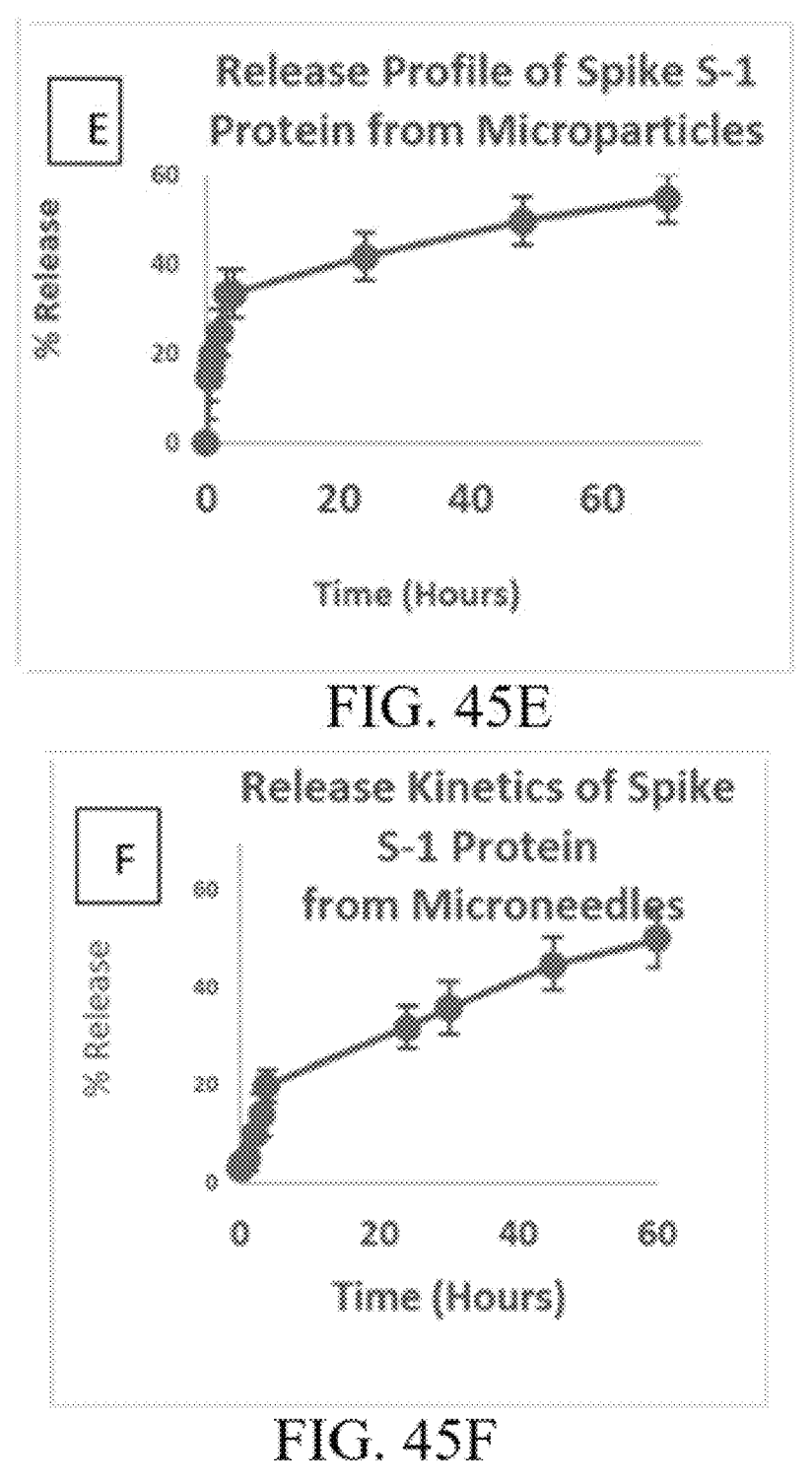

We further evaluated the time taken for the microneedles to dissolve and release the vaccine particles once administered transdermally. FIG. 45A is an image of the skin immediately after application of the microneedle patch. FIG. 45B shows the image of the same array of microneedles taken 10 minutes later showing closure of the pores on the skin after application of the microneedles. FIG. 45C is a SEM image of the microneedle patch. FIG. 45D is an SEM image taken after application of the vaccine microneedle patch on the skin of a mouse for 5 minutes, showing that the microneedles have dissolved and delivered the vaccine into the skin. In this study we noted that 92-95% if the vaccine particles were delivered into the skin. FIG. 45E represents the release kinetics of the Spike protein from the microparticle matrix, showing about 50% release in about 60 hours, demonstrating excellent sustained release of the vaccine antigen. FIG. 45F represents the release profile of the Spike protein from the microparticles within the microneedles, showing that about 50% was released within about 62 hours, indicating that the release of the vaccine antigen was controlled mostly by the release from the microparticle matrix and that the microneedles themselves did not further delay the antigen release.

Preliminary pre-clinical studies in mice targeting microneedle based microparticle delivery to immunologically active Langerhan cells in the skin induces protective immunity.

We have successfully formulated and tested several microneedle based microparticulate vaccines after transdermal administration for several other indications. We are currently working on a NIH funded microneedle based microparticulate Gonorrhea vaccine that demonstrated excellent efficacy.

Figure 46:
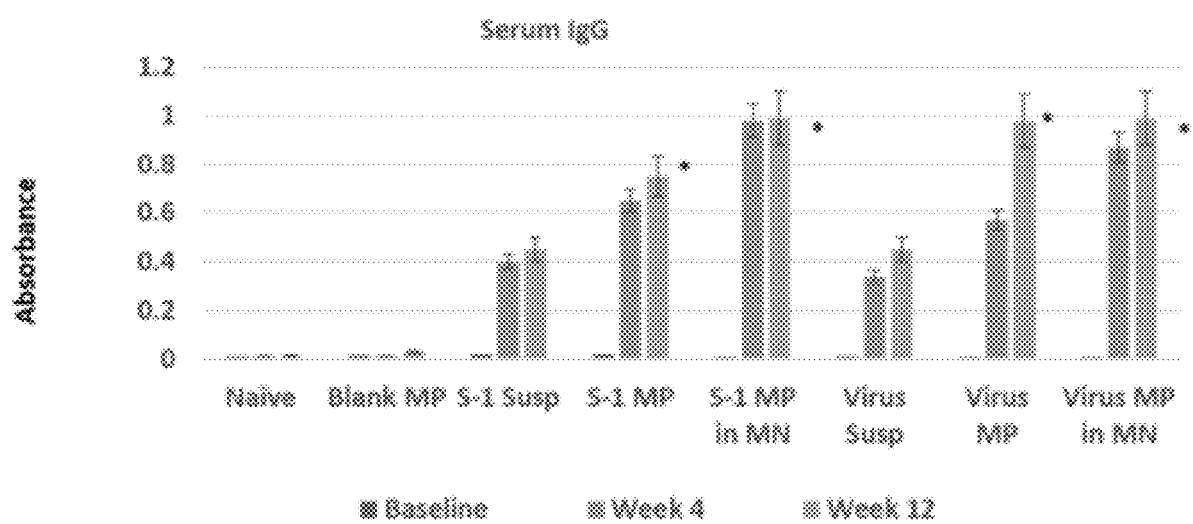
FIG. 46 shows Spike S-1 and SARS-CoV-2 Heat Inactivated Virus induced lose, hydroxyl-propyl methylcellulose acetate succinate (HPMCAS) and targeting agent AAL dissolved in de-ionized water. Briefly, 50 mg of β-cyclodextrin was dissolved in 5 mL of de-ionized water under stirring (Ref. No. (56)). 10 μL of 1N NaOH was added to the solution to aid the process. Once β-cyclodextrin was solubilized, 20 mg of HPMCAS was added to the solution and stirred overnight to solubilize it. Further 30% w/v ethyl cellulose suspension equivalent to 20 mg ethyl cellulose was added. The formulation also contained 5 mg trehalose and 0.01% tween-20. The pH of the resulting solution was neutralized and then 5 mg WCL of 4T07 cells was added. AAL was added to target the particles to M cells in the intestinal lumen. The aqueous formulation matrix was spray dried by one step process using the Buchi B-191 mini spray dryer (Buchi Corporation, New Castle, Del.) at inlet temperature 125° C., outlet temperature 80° C., 500 Nl/h, and 2% feed rate (20 mL/h) of peristaltic pump, and nozzle diameter 0.7 mm (Ref. No(s). (15)). The resulting microparticles were stored at −20° C. in a desiccant chamber till further use.

In summary, the studies in mice described above, targeting microneedle based microparticle delivery of either the Spike S-1 protein or the inactivated SARS-CoV-2 virus as the vaccine antigens to immunologically active Langerhan cells in the skin induces protective immunity. We obtained significantly higher IgG titers in the mice that received the microparticles of Spike protein or the inactivated virus when administered using microneedles as compared to i.m. administered vaccine suspension or microparticles at week 12 after a single microneedle vaccine patch administration. FIG. 46 shows Spike S-1-induced serum IgG levels and SARS-CoV-2 Heat Inactivated Virus-induced serum IgG levels. The mice received one vaccine dose at week 0, either as the antigen in suspension/solution or in microparticles or microparticles in microneedles. Serum IgG was determined at week 4 and 12. The microneedle group receiving particulate vaccines showed IgG levels significantly higher than the corresponding suspension vaccinated mice (*p<0.01 from suspension group). [S-1=Spike protein; Susp.=Suspension; MP=Microparticles, MN=Microneedles]

We also determined whether the vaccine the long-term memory responses after a single vaccine patch administration. The CD27 (memory B cell), CD45R (memory T cell) and CD62L (central T cell) responses in the spleen and lymph nodes of mice sacrificed at the end of the study, which were significantly higher in all the vaccine groups. This data indicates that a single dose of the microneedle vaccine patch may be clinically sufficient.

Recently, we have made major advances in formulation technology, allowing us to produce the vaccine microparticles using a patented, automated spray drying methodology. Likewise, we have produced the microneedles using an automated 3D Bioprinter. This is advantageous from the standpoint of advancing the vaccine formulation from the bench to clinic, as the scale-up process can be achieved with no further modifications.

We successfully formulated Alum, MF59®, MPL-A and other adjuvants that elicit toll like receptor responses, such as Resiquimod (R-848, a TLR 7/8 agonist, with potent antiviral activity), Imiquimod (R-837, a TLR 7 agonist, an immune response modifier with potent indirect antiviral activity that induces the production of cytokines such as IFN-α); and CpG (a TLR-9 agonist, which induces IFN-α). The formulation is then spray dried to obtain stable vaccine microparticles with excellent sustained release properties. Antigen presentation demonstrated excellent immunogenicity in cells culture studies with dendritic cells.

The in-vivo studies in mice demonstrated excellent antibody titers after administration of the vaccine antigens in both the Spike S-1 protein and using the inactivated SARS CoV-2 virus after encapsulation into microparticles and administration using microneedles. The responses after microneedle administration were significantly better that when the vaccine antigens were administered without the use of the microneedles (either as particles administered intramuscularly using the conventional needles technique of vaccine administration).

The present disclosure also contemplates the use of a plurality of different bioactive materials, such as, but not limited to, a plurality of different antigens used as a vaccine.

Although only a number of exemplary embodiments have been described in detail above, those skilled in the art will readily appreciate that many modifications are possible in the exemplary embodiments without materially departing from the novel teachings and advantages. Accordingly, all such modifications are intended to be included within the scope of this disclosure as defined in the following claims.

While the methods, equipment and systems have been described in connection with specific embodiments, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. It should further be noted that any patents, applications and publications referred to herein are incorporated by reference in their entirety.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods, equipment and systems. These and other components are disclosed herein, and it is understood that when combinations, subsets, interactions, groups, etc., of these components are disclosed that while specific reference of each various individual and collective combinations and permutation of these may not be explicitly disclosed, each is specifically contemplated and described herein, for all methods, equipment and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

What is claimed is:

1. A method of producing at least one microneedle comprising a vaccine for transdermal delivery of the vaccine to a patient, comprising:
   (a) preparing microparticles or nanoparticles of encapsulated vaccine by:
      (i) preparing a solution comprising a vaccine antigen and a biocompatible polymer matrix; and
      (ii) spray drying the solution to form the microparticles or nanoparticles;
   (b) preparing a film composition comprising at least one pre-polymer solution, wherein the at least one pre-polymer solution comprises poly(ethylene glycol)diacrylate (PEGDA);
   (c) preparing a suspension comprising the microparticles or nanoparticles and the film composition;
   (d) loading the suspension into a 3D printer;
   (e) printing, via the 3D printer, at least one microneedle comprising the suspension; and,
   (f) converting the pre-polymer solution into a cross-linked biopolymer by exposing the at least one microneedle to UV light.

2. The method of claim 1, wherein the film composition further comprises polyvinylpyrrolidone, a photo-initiator, and a surfactant.

3. The method of claim 2, wherein the film composition further comprises a sugar or sodium bicarbonate.

4. The method of claim 1, wherein the microparticles or nanoparticles comprise an adjuvant.

5. The method of claim 1, wherein the biocompatible polymer matrix comprises albumin cross-linked with glutaraldehyde.

6. The method of claim 1, wherein the at least one microneedle comprises an array comprising a plurality of microneedles.

7. The method of claim 1, wherein printing the array of microneedles via the 3D printer comprises dispensing, via the 3D printer, the suspension into a mold configured to form the microneedles.

8. The method of claim 1, wherein exposing the at least one microneedle to UV light comprises exposing the at least one microneedle to UV light having a wavelength in the range of about 365 nm to about 405 nm.

9. The method of claim 1, wherein the vaccine antigen comprises the S-1 spike protein of SARS-CoV-2 virus or heat-inactivated SARS-CoV-2 virus.

10. A method of transdermal delivery of a vaccine, comprising:
  providing the at least one microneedle of claim 1; and
    (b) injecting the encapsulated microparticles or nanoparticles transdermally through the at least one microneedle by applying the microneedle to the skin of a patient and allowing the film composition to biodegrade, thereby releasing the encapsulated microparticles or nanoparticles into the skin, whereby the encapsulated vaccine retains bioactivity after cellular uptake.

11. A microneedle for transdermal delivery of a bioactive material, comprising:
  a plurality of microneedles comprising:
    (a) a film composition comprising a cross-linked biopolymer; and
    (b) encapsulated microparticles or nanoparticles comprising a bioactive material and a biocompatible polymer matrix suspended within the film composition,
  wherein the film composition is configured to biodegrade and transdermally inject the vaccine when applied to the skin of a patient, whereby the encapsulated vaccine retains bioactivity after cellular uptake,
  wherein printing the plurality of microneedles via the 3D printer comprises dispensing, via the 3D printer, the suspension into a mold configured to form the microneedles.

12. The microneedle of claim 11, wherein pre-polymer solution comprises poly(ethylene glycol)diacrylate (PEGDA).

13. The microneedle of claim 11, wherein the film composition further comprises polyvinylpyrrolidone, a photoinitiator, and a surfactant.

14. The microneedle of claim 13, wherein the film composition further comprises a sugar or sodium bicarbonate.

15. The microneedle of claim 11, wherein the microparticles or nanoparticles comprise an adjuvant.

16. The microneedle of claim 11, wherein the biocompatible polymer matrix comprises albumin cross-linked with glutaraldehyde.

17. The microneedle of claim 11, wherein the at least one microneedle comprises an array comprising a plurality of microneedles.

18. The microneedle of claim 11, wherein the microneedles are configured to be exposed to UV light having a wavelength in the range of about 365 nm to about 405 nm.

19. The system of claim 11, wherein the bioactive material comprises at least one vaccine antigen.

20. The system of claim 11, wherein the at least one vaccine antigen comprises the S-1 spike protein of SARS-CoV-2 virus or heat-inactivated SARS-CoV-2 virus.

21. A microneedle for transdermal delivery of a bioactive material, comprising:
  a plurality of microneedles comprising:
    (a) a film composition comprising a cross-linked biopolymer; and
    (b) encapsulated microparticles or nanoparticles comprising a bioactive material and a biocompatible polymer matrix suspended within the film composition,
  wherein the film composition is configured to biodegrade and transdermally inject the vaccine when applied to the skin of a patient, whereby the encapsulated vaccine retains bioactivity after cellular uptake, and
  wherein the at least one vaccine antigen comprises the S-1 spike protein of SARS-CoV-2 virus or heat-inactivated SARS-CoV-2 virus.

* * * * *